US008216590B2

(12) United States Patent
Houghton et al.

(10) Patent No.: US 8,216,590 B2
(45) Date of Patent: Jul. 10, 2012

(54) HCV FUSION POLYPEPTIDES

(75) Inventors: Michael Houghton, Danville, CA (US);
Yin-Ling Lin, Emeryville, CA (US);
Angelica Medina-Selby, San Francisco, CA (US); Doris Coit, Petaluma, CA (US)

(73) Assignee: Novartis AG, Basel (CH)

( * ) Notice: Subject to any disclaimer, the term of this patent is extended or adjusted under 35 U.S.C. 154(b) by 293 days.

(21) Appl. No.: 12/310,406

(22) PCT Filed: Aug. 27, 2007

(86) PCT No.: PCT/US2007/018940
§ 371 (c)(1),
(2), (4) Date: Dec. 7, 2009

(87) PCT Pub. No.: WO2008/024518
PCT Pub. Date: Feb. 28, 2008

(65) Prior Publication Data
US 2010/0092503 A1  Apr. 15, 2010

Related U.S. Application Data

(60) Provisional application No. 60/840,162, filed on Aug. 25, 2006.

(51) Int. Cl.
*A61K 39/29* (2006.01)
*A61K 48/00* (2006.01)
(52) U.S. Cl. .................. 424/227.1; 424/192.1
(58) Field of Classification Search .............. None
See application file for complete search history.

(56) References Cited

U.S. PATENT DOCUMENTS

| 5,350,671 | A | 9/1994 | Houghton et al. |
| 5,683,864 | A | 11/1997 | Houghton et al. |
| 6,150,087 | A | 11/2000 | Chien |
| 6,482,792 | B2 | 11/2002 | Ip |
| 6,514,731 | B1 | 2/2003 | Valenzuela et al. |
| 6,562,346 | B1 | 5/2003 | Paliard et al. |
| 2006/0088819 | A1 | 4/2006 | Houghton et al. |

FOREIGN PATENT DOCUMENTS

| WO | WO 93/00365 | | 1/1993 |
| WO | WO 94/01778 | | 1/1994 |
| WO | WO 99/63941 | | 12/1999 |
| WO | WO 01/38360 | | 5/2001 |
| WO | WO2004/005473 | * | 1/2004 |
| WO | WO 2004/005473 A | | 1/2004 |
| WO | WO 2004/039950 A2 | | 5/2004 |
| WO | WO 2005/113837 A | | 12/2005 |
| WO | WO 2006/024020 A | | 3/2006 |
| WO | WO 2006/033768 A | | 3/2006 |

OTHER PUBLICATIONS

Tomei et al. J Virol. 1993, vol. 67, No. 7, p. 4017-4026.*
Shira et al. J. Virol. 1994, vol. 68, No. 5, pp. 3334-3342.*
Balan et al. Yeast 2005, vol. 22, pp. 203-212.*
Al, et al., "Expression of Recombinant Hepatitis C Virus Non-Structural Protein 5B in *Escherichia coli,*" *Virus Res* 53(2):141-149 (1998).
Cheney, et al., "Mutations of NS5B Polymerase of Hepatitis C Virus: Impacts on in Vitro Enzymatic Activity and Viral RNA Replication in the Subgenomic Replicon Cell Structure," *Virology* 297:298-306 (2002).
Chien, et al., "Diagnosis of Hepatitis C Virus (HCV) Infection Using an Immunodominant Chimeric Polyprotein to Capture Circulating Antibodies: Reevaluation of the Role of HCV in Liver Disease," *PNAS USA* 89:1011-10015 (1992).
Chien, et al., "Use of Recombinant HCV Antigen in the Serodiagnosis of Hepatitis C Virus Infection: Significant Improvement in HCV Antibody Detection As Compared With the First Generation HCV C100-3 ELISA and the Synthetic Peptide EIA Tests.," *J Gastroent Hepatol* 8:s33-s39 (1993).
Forns, et al., "Characterization of Modified Hepatitis C Virus E2 Proteins Expressed on the Cell Surface," *Virology* 274(1):75-85 (2000).
Hou, et al., "Identification of B Cell Isotopes of Hepatitis C Virus RNA Dependant RNA Polymerase," *J Virol Meth* 104:1-8 (2002).
Oh, et al., "A Recombinant Hepatitis C Virus RNA-Dependant RNA Polymerase Capable of Copying the Full-Length Viral RNA," *J Virol* 73(9):7694-7702 (1999).
Yamashita, et al., "RNA-Dependent RNA Polymerase Activity of the Soluable Recombinant Hepatitis C Virus NS5B Protein Truncated at the C-Terminal Region," *J Biol Chem* 273(25):15479-15486 (1998).
Qin, et al., "Mutational Analysis of the Structure and Functions of Hepatitis C Virus RNA-Dependant Polymerase," *Hepatology* 33(3):728-737 (2001).
Vajdy, et al., "Hepatitis C Virus Polyprotein Vaccine Formulations Capable of Inducing Broad Antibody and Cellular Immune Rersponses," *J Gen Virol* 87(8):2253-2262 (2006).

* cited by examiner

*Primary Examiner* — Bao Li
(74) *Attorney, Agent, or Firm* — Roberta L. Robins; Kenneth M. Goldman; Robert Gorman

(57) ABSTRACT

The invention provides HCV fusion polypeptides including truncated or full-length HCV NS5 polypeptides, and a portion of the HCV NS2 polypeptide, fused to at least one other HCV epitope derived from another region of the HCV polyprotein. The fusions can be used in methods of stimulating an immune response to HCV, for example a cellular immune response to HCV, such as activating hepatitis C virus (HCV)-specific T cells, including CD4+ and CD8+ T cells. The method can be used in model systems to develop HCV-specific immunogenic compositions, as well as to immunize against HCV.

7 Claims, 32 Drawing Sheets

```
       1                                              10
       M   A   P   I   T   A   Y   A   Q   Q
       ATG GCG CCC ATC ACG GCG TAC GCC CAG CAG

20
   T   R   G   L   L   G   C   I   I   T   S   L   T   G   R
   ACA AGG GGC CTC CTA GGG TGC ATA ATC ACC AGC CTA ACT GGC CGG 30                                          40
   D   K   N   Q   V   E   G   E   V   Q   I   V   S   T   A
   GAC AAA AAC CAA GTG GAG GGT GAG GTC CAG ATT GTG TCA ACT GCT

50
   A   Q   T   F   L   A   T   C   I   N   G   V   C   W   T
   GCC CAA ACC TTC CTG GCA ACG TGC ATC AAT GGG GTG TGC TGG ACT 60                                      70
   V   Y   H   G   A   G   T   R   T   I   A   S   P   K   G
   GTC TAC CAC GGG GCC GGA ACG AGG ACC ATC GCG TCA CCC AAG GGT

80
   P   V   I   Q   M   Y   T   N   V   D   Q   D   L   V   G
   CCT GTC ATC CAG ATG TAT ACC AAT GTA GAC CAA GAC CTT GTG GGC 90                                  100
   W   P   A   P   Q   G   S   R   S   L   T   P   C   T   C
   TGG CCC GCT CCG CAA GGT AGC CGA TCA TTG ACA CCC TGC ACT TGC

110
   G   S   S   D   L   Y   L   V   T   R   H   A   D   V   I
   GGC TCC TCG GAC CTT TAC CTG GTC ACG AGG CAC GCC GAT GTC ATT 120                                 130
   P   V   R   R   R   G   D   S   R   G   S   L   L   S   P
   CCC GTG CGC CGG CGG GGT GAT AGC AGG GGC AGC CTG CTG TCG CCC

140
   R   P   I   S   Y   L   K   G   S   S   G   G   P   L   L
   CGG CCC ATT TCC TAC TTG AAA GGC TCC TCG GGG GGT CCG CTG TTG 150                                     160
   C   P   A   G   H   A   V   G   I   F   R   A   A   V   C
   TGC CCC GCG GGG CAC GCC GTG GGC ATA TTT AGG GCC GCG GTG TGC

170
   T   R   G   V   A   K   A   V   D   F   I   P   V   E   N
   ACC CGT GGA GTG GCT AAG GCG GTG GAC TTT ATC CCT GTG GAG AAC

180
   L   E   T   T   M   R   S
   CTA GAG ACA ACC ATG AGG TCC
```

FIG. 2

```
            1
            M   A   A   Y   A   A   Q   G   Y  10
                                               K
           ATG GCT GCA TAT GCA GCT CAG GGC TAT AAG

20
 V   L   V   L   N   P   S   V   A   A   T   L   G   F   G
GTG CTA GTA CTC AAC CCC TCT GTT GCT GCA ACA CTG GGC TTT GGT 30                                        40
 A   Y   M   S   K   A   H   G   I   D   P   N   I   R   T
GCT TAC ATG TCC AAG GCT CAT GGG ATC GAT CCT AAC ATC AGG ACC

50
 G   V   R   T   I   T   T   G   S   P   I   T   Y   S   T
GGG GTG AGA ACA ATT ACC ACT GGC AGC CCC ATC ACG TAC TCC ACC 60                                70
 Y   G   K   F   L   A   D   G   G   C   S   G   G   A   Y
TAC GGC AAG TTC CTT GCC GAC GGC GGG TGC TCG GGG GCT TAT

80
 D   I   I   I   C   D   E   C   H   S   T   D   A   T   S
GAC ATA ATA ATT TGT GAC GAG TGC CAC TCC ACG GAT GCC ACA TCC 90                           100
 I   L   G   I   G   T   V   L   D   Q   A   E   T   A   G
ATC TTG GGC ATT GGC ACT GTC CTT GAC CAA GCA GAG ACT GCG GGG

110
 A   R   L   V   V   L   A   T   A   T   P   P   G   S   V
GCG AGA CTG GTT GTG CTC GCC ACC GCC ACC CCT CCG GGC TCC GTC 120                              130
 T   V   P   H   P   N   I   E   E   V   A   L   S   T   T
ACT GTG CCC CAT CCC AAC ATC GAG GAG GTT GCT CTG TCC ACC ACC

140
 G   E   I   P   F   Y   G   K   A   I   P   L   E   V   I
GGA GAG ATC CCT TTT TAC GGC AAG GCT ATC CCC CTC GAA GTA ATC 150                                  160
 K   G   G   R   H   L   I   F   C   H   S   K   K   K   C
AAG GGG GGG AGA CAT CTC ATC TTC TGT CAT TCA AAG AAG AAG TGC

170
 D   E   L   A   A   K   L   V   A   L   G   I   N   A   V
GAC GAA CTC GCC GCA AAG CTG GTC GCA TTG GGC ATC AAT GCC GTG 180                                      190
 A   Y   Y   R   G   L   D   V   S   V   I   P   T   S   G
GCC TAC TAC CGC GGT CTT GAC GTG TCC GTC ATC CCG ACC AGC GGC

200
 D   V   V   V   V   A   T   D   A   L   M   T   G   Y   T
GAT GTT GTC GTC GTG GCA ACC GAT GCC CTC ATG ACC GGC TAT ACC

FIG. 3A
```

```
  G    D    F    D   ²¹⁰S   V    I    D    C    N    T    C    V    T   ²²⁰Q
 GGC  GAC  TTC  GAC  TCG  GTG  ATA  GAC  TGC  AAT  ACG  TGT  GTC  ACC  CAG

T    V    D    F    S    L    D    P    T   ²³⁰F   T    I    E    T    I
 ACA  GTC  GAT  TTC  AGC  CTT  GAC  CCT  ACC  TTC  ACC  ATT  GAG  ACA  ATC

T    L    P    Q   ²⁴⁰D   A    V    S    R    T    Q    R    R    G   ²⁵⁰R
 ACG  CTC  CCC  CAA  GAT  GCT  GTC  TCC  CGC  ACT  CAA  CGT  CGG  GGC  AGG

T    G    R    G    K    P    G    I    Y   ²⁶⁰R   F    V    A    P    G
 ACT  GGC  AGG  GGG  AAG  CCA  GGC  ATC  TAC  AGA  TTT  GTG  GCA  CCG  GGG

E    R    P    S   ²⁷⁰G   M    F    D    S    S    V    L    C    E   ²⁸⁰C
 GAG  CGC  CCC  TCC  GGC  ATG  TTC  GAC  TCG  TCC  GTC  CTC  TGT  GAG  TGC

Y    D    A    G    C    A    W    Y    E   ²⁹⁰L   T    P    A    E    T
 TAT  GAC  GCA  GGC  TGT  GCT  TGG  TAT  GAG  CTC  ACG  CCC  GCC  GAG  ACT

T    V    R    L   ³⁰⁰R   A    Y    M    N    T    P    G    L    P   ³¹⁰V
 ACA  GTT  AGG  CTA  CGA  GCG  TAC  ATG  AAC  ACC  CCG  GGG  CTT  CCC  GTG

C    Q    D    H    L    E    F    W    E   ³²⁰G   V    F    T    G    L
 TGC  CAG  GAC  CAT  CTT  GAA  TTT  TGG  GAG  GGC  GTC  TTT  ACA  GGC  CTC

T    H    I    D   ³³⁰A   H    F    L    S    Q    T    K    Q    S   ³⁴⁰G
 ACT  CAT  ATA  GAT  GCC  CAC  TTT  CTA  TCC  CAG  ACA  AAG  CAG  AGT  GGG

E    N    L    P    Y    L    V    A    Y   ³⁵⁰Q   A    T    V    C    A
 GAG  AAC  CTT  CCT  TAC  CTG  GTA  GCG  TAC  CAA  GCC  ACC  GTG  TGC  GCT

R    A    Q    A   ³⁶⁰P   P    P    S    W    D    Q    M    W    K   ³⁷⁰C
 AGG  GCT  CAA  GCC  CCT  CCC  CCA  TCG  TGG  GAC  CAG  ATG  TGG  AAG  TGT

L    I    R    L    K    P    T    L    H   ³⁸⁰G   P    T    P    L    L
 TTG  ATT  CGC  CTC  AAG  CCC  ACC  CTC  CAT  GGG  CCA  ACA  CCC  CTG  CTA

Y    R    L    G   ³⁹⁰A   V    Q    N    E    I    T    L    T    H   ⁴⁰⁰P
 TAC  AGA  CTG  GGC  GCT  GTT  CAG  AAT  GAA  ATC  ACC  CTG  ACG  CAC  CCA

V    T    K    Y    I    M    T    C    M   ⁴¹⁰S   A    D    L    E    V
 GTC  ACC  AAA  TAC  ATC  ATG  ACA  TGC  ATG  TCG  GCC  GAC  CTG  GAG  GTC
```

FIG. 3B

```
  V   T   S   T   420
                  W   V   L   V   G   G   V   L   A   A   430
                                                          L
 GTC ACG AGC ACC TGG GTG CTC GTT GGC GGC GTC CTG GCT GCT TTG

A   A   Y   C   L   S   T   G   C   440
                                      V   V   I   V   G   R
 GCC GCG TAT TGC CTG TCA ACA GGC TGC GTG GTC ATA GTG GGC AGG

V   V   L   S   450
                  G   K   P   A   I   I   P   D   R   E   460
                                                          V
 GTC GTC TTG TCC GGG AAG CCG GCA ATC ATA CCT GAC AGG GAA GTC

L   Y   R   E   F   D   E   M   E   470
                                      E   C   S   Q   H   L
 CTC TAC CGA GAG TTC GAT GAG ATG GAA GAG TGC TCT CAG CAC TTA

P   Y   I   E   480
                  Q   G   M   M   L   A   E   Q   F   K   490
                                                          Q
 CCG TAC ATC GAG CAA GGG ATG ATG CTC GCC GAG CAG TTC AAG CAG

K   A   L   G   L   L   Q   T   A   500
                                      S   R   Q   A   E   V
 AAG GCC CTC GGC CTC CTG CAG ACC GCG TCC CGT CAG GCA GAG GTT

I   A   P   A   510
                  V   Q   T   N   W   Q   K   L   E   T   520
                                                          F
 ATC GCC CCT GCT GTC CAG ACC AAC TGG CAA AAA CTC GAG ACC TTC

W   A   K   H   M   W   N   F   I   530
                                      S   G   I   Q   Y   L
 TGG GCG AAG CAT ATG TGG AAC TTC ATC AGT GGG ATA CAA TAC TTG

A   G   L   S   540
                  T   L   P   G   N   P   A   I   A   S   550
                                                          L
 GCG GGC TTG TCA ACG CTG CCT GGT AAC CCC GCC ATT GCT TCA TTG

M   A   F   T   A   A   V   T   S   560
                                      P   L   T   T   S   Q
 ATG GCT TTT ACA GCT GCT GTC ACC AGC CCA CTA ACC ACT AGC CAA

T   L   L   F   570
                  N   I   L   G   G   W   V   A   A   Q   580
                                                          L
 ACC CTC CTC TTC AAC ATA TTG GGG GGG TGG GTG GCT GCC CAG CTC

A   A   P   G   A   A   T   A   F   590
                                      V   G   A   G   L   A
 GCC GCC CCC GGT GCC GCT ACT GCC TTT GTG GGC GCT GGC TTA GCT

G   A   A   I   600
                  G   S   V   G   L   G   K   V   L   I   610
                                                          D
 GGC GCC GCC ATC GGC AGT GTT GGA CTG GGG AAG GTC CTC ATA GAC

I   L   A   G   Y   G   A   G   V   620
                                      A   G   A   L   V   A
 ATC CTT GCA GGG TAT GGC GCG GGC GTG GCG GGA GCT CTT GTG GCA
```

FIG. 3C

```
                            630                                                    640
 F   K   I   M   S   G   E   V   P   S   T   E   D   L   V
TTC AAG ATC ATG AGC GGT GAG GTC CCC TCC ACG GAG GAC CTG GTC

650
 N   L   L   P   A   I   L   S   P   G   A   L   V   V   G
AAT CTA CTG CCC GCC ATC CTC TCG CCC GGA GCC CTC GTA GTC GGC 660                                                    670
 V   V   C   A   A   I   L   R   R   H   V   G   P   G   E
GTG GTC TGT GCA GCA ATA CTG CGC CGG CAC GTT GGC CCG GGC GAG

680
 G   A   V   Q   W   M   N   R   L   I   A   F   A   S   R
GGG GCA GTG CAG TGG ATG AAC CGG CTG ATA GCC TTC GCC TTC CGG 690                                            700
 G   N   H   V   S   P   T   H   Y   V   P   E   S   D   A
GGG AAC CAT GTT TCC CCC ACG CAC TAC GTG CCG GAG AGC GAT GCA

710
 A   A   R   V   T   A   I   L   S   S   L   T   V   T   Q
GCT GCC CGC GTC ACT GCC ATA CTC AGC AGC CTC ACT GTA ACC CAG 720                                    730
 L   L   R   R   L   H   Q   W   I   S   S   E   C   T   T
CTC CTG AGG CGA CTG CAC CAG TGG ATA AGC TCG GAG TGT ACC ACT

740
 P   C   S   G   S   W   L   R   D   I   W   D   W   I   C
CCA TGC TCC GGT TCC TGG CTA AGG GAC ATC TGG GAC TGG ATA TGC 750                                            760
 E   V   L   S   D   F   K   T   W   L   K   A   K   L   M
GAG GTG TTG AGC GAC TTT AAG ACC TGG CTA AAA GCT AAG CTC ATG

770
 P   Q   L   P   G   I   P   F   V   S   C   Q   R   G   Y
CCA CAG CTG CCT GGG ATC CCC TTT GTG TCC TGC CAG CGC GGG TAT 780                                            790
 K   G   V   W   R   G   D   G   I   M   H   T   R   C   H
AAG GGG GTC TGG CGA GGG GAC GGC ATC ATG CAC ACT CGC TGC CAC

800
 C   G   A   E   I   T   G   H   V   K   N   G   T   M   R
TGT GGA GCT GAG ATC ACT GGA CAT GTC AAA AAC GGG ACG ATG AGG 810                                            820
 I   V   G   P   R   T   C   R   N   M   W   S   G   T   F
ATC GTC GGT CCT AGG ACC TGC AGG AAC ATG TGG AGT GGG ACC TTC

830
 P   I   N   A   Y   T   T   G   P   C   T   P   L   P   A
CCC ATT AAT GCC TAC ACC ACG GGC CCC TGT ACC CCC CTT CCT GCG
```

FIG. 3D

```
      P   N   Y   T   F⁸⁴⁰ A   L   W   R   V   S   A   E   E   Y⁸⁵⁰
      CCG AAC TAC ACG TTC GCG CTA TGG AGG GTG TCT GCA GAG GAA TAC

V   E   I   R   Q   V   G   D   F   H⁸⁶⁰ Y   V   T   G   M
      GTG GAG ATA AGG CAG GTG GGG GAC TTC CAC TAC GTG ACG GGT ATG

T   T   D   N   L⁸⁷⁰ K   C   P   C   Q   V   P   S   P   E⁸⁸⁰
      ACT ACT GAC AAT CTT AAA TGC CCG TGC CAG GTC CCA TCG CCC GAA

F   F   T   E   L   D   G   V   R   L⁸⁹⁰ H   R   F   A   P
      TTT TTC ACA GAA TTG GAC GGG GTG CGC CTA CAT AGG TTT GCG CCC

P   C   K   P   L⁹⁰⁰ L   R   E   E   V   S   F   R   V   G⁹¹⁰
      CCC TGC AAG CCC TTG CTG CGG GAG GAG GTA TCA TTC AGA GTA GGA

L   H   E   Y   P   V   G   S   Q   L⁹²⁰ P   C   E   P   E
      CTC CAC GAA TAC CCG GTA GGG TCG CAA TTA CCT TGC GAG CCC GAA

P   D   V   A   V⁹³⁰ L   T   S   M   L   T   D   P   S   H⁹⁴⁰
      CCG GAC GTG GCC GTG TTG ACG TCC ATG CTC ACT GAT CCC TCC CAT

I   T   A   E   A   A   G   R   R   L⁹⁵⁰ A   R   G   S   P
      ATA ACA GCA GAG GCG GCC GGG CGA AGG TTG GCG AGG GGA TCA CCC

P   S   V   A   S⁹⁶⁰ S   S   A   S   Q   L   S   A   P   S⁹⁷⁰
      CCC TCT GTG GCC AGC TCC TCG GCT AGC CAG CTA TCC GCT CCA TCT

L   K   A   T   C   T   A   N   H   D⁹⁸⁰ S   P   D   A   E
      CTC AAG GCA ACT TGC ACC GCT AAC CAT GAC TCC CCT GAT GCT GAG

L   I   E   A   N⁹⁹⁰ L   L   W   R   Q   E   M   G   G   N¹⁰⁰⁰
      CTC ATA GAG GCC AAC CTC CTA TGG AGG CAG GAG ATG GGC GGC AAC

I   T   R   V   E   S   E   N   K   V¹⁰¹⁰ V   I   L   D   S
      ATC ACC AGG GTT GAG TCA GAA AAC AAA GTG GTG ATT CTG GAC TCC

F   D   P   L   V¹⁰²⁰ A   E   E   D   E   R   E   I   S   V¹⁰³⁰
      TTC GAT CCG CTT GTG GCG GAG GAG GAC GAG CGG GAG ATC TCC GTA

P   A   E   I   L   R   K   S   R   R¹⁰⁴⁰ F   A   Q   A   L
      CCC GCA GAA ATC CTG CGG AAG TCT CGG AGA TTC GCC CAG GCC CTG
```

FIG. 3E

```
         P   V   W   A   R   P   D   Y   N   P   P   L   V   E   T
                         1050                                  1060
        CCC GTT TGG GCG CGG CCG GAC TAT AAC CCC CCG CTA GTG GAG ACG

W   K   K   P   D   Y   E   P   P   V   V   H   G   C   P
                                             1070
        TGG AAA AAG CCC GAC TAC GAA CCA CCT GTG GTC CAT GGC TGC CCG

L   P   P   P   K   S   P   P   V   P   P   P   R   K   K
                         1080                                  1090
        CTT CCA CCT CCA AAG TCC CCT CCT GTG CCT CCG CCT CGG AAG AAG

R   T   V   V   L   T   E   S   T   L   S   T   A   L   A
                                                 1100
        CGG ACG GTG GTC CTC ACT GAA TCA ACC CTA TCT ACT GCC TTG GCC

E   L   A   T   R   S   F   G   S   S   S   T   S   G   I
                         1110                                  1120
        GAG CTC GCC ACC AGA AGC TTT GGC AGC TCC TCA ACT TCC GGC ATT

T   G   D   N   T   T   T   S   S   E   P   A   P   S   G
                                                 1130
        ACG GGC GAC AAT ACG ACA ACA TCC TCT GAG CCC GCC CCT TCT GGC

C   P   P   D   S   D   A   E   S   Y   S   S   M   P   P
                         1140                                  1150
        TGC CCC CCC GAC TCC GAC GCT GAG TCC TAT TCC TCC ATG CCC CCC

L   E   G   E   P   G   D   P   D   L   S   D   G   S   W
                                             1160
        CTG GAG GGG GAG CCT GGG GAT CCG GAT CTT AGC GAC GGG TCA TGG

S   T   V   S   S   E   A   N   A   E   D   V   V   C   C
                         1170                                  1180
        TCA ACG GTC AGT AGT GAG GCC AAC GCG GAG GAT GTC GTG TGC TGC

S   M   S   Y   S   W   T   G   A   L   V   T   P   C   A
                                             1190
        TCA ATG TCT TAC TCT TGG ACA GGC GCA CTC GTC ACC CCG TGC GCC

A   E   E   Q   K   L   P   I   N   A   L   S   N   S   L
                         1200                                  1210
        GCG GAA GAA CAG AAA CTG CCC ATC AAT GCA CTA AGC AAC TCG TTG

L   R   H   H   N   L   V   Y   S   T   T   S   R   S   A
                                             1220
        CTA CGT CAC CAC AAT TTG GTG TAT TCC ACC ACC TCA CGC AGT GCT

C   Q   R   Q   K   K   V   T   F   D   R   L   Q   V   L
                         1230                                  1240
        TGC CAA AGG CAG AAG AAA GTC ACA TTT GAC AGA CTG CAA GTT CTG

D   S   H   Y   Q   D   V   L   K   E   V   K   A   A   A
                                             1250
        GAC AGC CAT TAC CAG GAC GTA CTC AAG GAG GTT AAA GCA GCG GCG
```

FIG. 3F

```
                    1260
 S   K   V   K   A   N   L   L   S   V   E   E   A   C   S1270
TCA AAA GTG AAG GCT AAC TTG CTA TCC GTA GAG GAA GCT TGC AGC

1280
 L   T   P   P   H   S   A   K   S   K   F   G   Y   G   A
CTG ACG CCC CCA CAC TCA GCC AAA TCC AAG TTT GGT TAT GGG GCA 1290                                1300
 K   D   V   R   C   H   A   R   K   A   V   T   H   I   N
AAA GAC GTC CGT TGC CAT GCC AGA AAG GCC GTA ACC CAC ATC AAC

1310
 S   V   W   K   D   L   L   E   D   N   V   T   P   I   D
TCC GTG TGG AAA GAC CTT CTG GAA GAC AAT GTA ACA CCA ATA GAC 1320                                1330
 T   T   I   M   A   K   N   E   V   F   C   V   Q   P   E
ACT ACC ATC ATG GCT AAG AAC GAG GTT TTC TGC GTT CAG CCT GAG

1340
 K   G   G   R   K   P   A   R   L   I   V   F   P   D   L
AAG GGG GGT CGT AAG CCA GCT CGT CTC ATC GTG TTC CCC GAT CTG 1350                                1360
 G   V   R   V   C   E   K   M   A   L   Y   D   V   V   T
GGC GTG CGC GTG TGC GAA AAG ATG GCT TTG TAC GAC GTG GTT ACA

1370
 K   L   P   L   A   V   M   G   S   S   Y   G   F   Q   Y
AAG CTC CCC TTG GCC GTG ATG GGA AGC TCC TAC GGA TTC CAA TAC 1380                                1390
 S   P   G   Q   R   V   E   F   L   V   Q   A   W   K   S
TCA CCA GGA CAG CGG GTT GAA TTC CTC GTG CAA GCG TGG AAG TCC

1400
 K   K   T   P   M   G   F   S   Y   D   T   R   C   F   D
AAG AAA ACC CCA ATG GGG TTC TCG TAT GAT ACC CGC TGC TTT GAC 1410                                1420
 S   T   V   T   E   S   D   I   R   T   E   E   A   I   Y
TCC ACA GTC ACT GAG AGC GAC ATC CGT ACG GAG GAG GCA ATC TAC

1430
 Q   C   C   D   L   D   P   Q   A   R   V   A   I   K   S
CAA TGT TGT GAC CTC GAC CCC CAA GCC CGC GTG GCC ATC AAG TCC 1440                                1450
 L   T   E   R   L   Y   V   G   G   P   L   T   N   S   R
CTC ACC GAG AGG CTT TAT GTT GGG GGC CCT CTT ACC AAT TCA AGG

1460
 G   E   N   C   G   Y   R   R   C   R   A   S   G   V   L
GGG GAG AAC TGC GGC TAT CGC AGG TGC CGC GCG AGC GGC GTA CTG
```

FIG. 3G

```
     T   T   S   C   G   N   T   L   T   C   Y   I   K   A   R
                      1470                                  1480
    ACA ACT AGC TGT GGT AAC ACC CTC ACT TGC TAC ATC AAG GCC CGG

A   A   C   R   A   A   G   L   Q   D   C   T   M   L   V
                                      1490
    GCA GCC TGT CGA GCC GCA GGG CTC CAG GAC TGC ACC ATG CTC GTG

C   G   D   D   L   V   V   I   C   E   S   A   G   V   Q
                      1500                                  1510
    TGT GGC GAC GAC TTA GTC GTT ATC TGT GAA AGC GCG GGG GTC CAG

E   D   A   A   S   L   R   A   F   T   E   A   M   T   R
                                  1520
    GAG GAC GCG GCG AGC CTG AGA GCC TTC ACG GAG GCT ATG ACC AGG

Y   S   A   P   P   G   D   P   P   Q   P   E   Y   D   L
                      1530                                  1540
    TAC TCC GCC CCC CCT GGG GAC CCC CCA CAA CCA GAA TAC GAC TTG

E   L   I   T   S   C   S   S   N   V   S   V   A   H   D
                                      1550
    GAG CTC ATA ACA TCA TGC TCC TCC AAC GTG TCA GTC GCC CAC GAC

G   A   G   K   R   V   Y   Y   L   T   R   D   P   T   T
                      1560                                  1570
    GGC GCT GGA AAG AGG GTC TAC TAC CTC ACC CGT GAC CCT ACA ACC

P   L   A   R   A   A   W   E   T   A   R   H   T   P   V
                                          1580
    CCC CTC GCG AGA GCT GCG TGG GAG ACA GCA AGA CAC ACT CCA GTC

N   S   W   L   G   N   I   I   M   F   A   P   T   L   W
                      1590                                  1600
    AAT TCC TGG CTA GGC AAC ATA ATC ATG TTT GCC CCC ACA CTG TGG

A   R   M   I   L   M   T   H   F   F   S   V   L   I   A
                                          1610
    GCG AGG ATG ATA CTG ATG ACC CAT TTC TTT AGC GTC CTT ATA GCC

R   D   Q   L   E   Q   A   L   D   C   E   I   Y   G   A
                      1620                                  1630
    AGG GAC CAG CTT GAA CAG GCC CTC GAT TGC GAG ATC TAC GGG GCC

C   Y   S   I   E   P   L   D   L   P   P   I   I   Q   R
                                      1640
    TGC TAC TCC ATA GAA CCA CTG GAT CTA CCT CCA ATC ATT CAA AGA

L   H   G   L   S   A   F   S   L   H   S   Y   S   P   G
                      1650                                  1660
    CTC CAT GGC CTC AGC GCA TTT TCA CTC CAC AGT TAC TCT CCA GGT

E   I   N   R   V   A   A   C   L   R   K   L   G   V   P
                                          1670
    GAA ATC AAT AGG GTG GCC GCA TGC CTC AGA AAA CTT GGG GTA CCG
```

FIG. 3H

```
         1680
P   L   R   A   W   R   H   R   A   R   S   V   R   A   R
                                                      1690
CCC TTG CGA GCT TGG AGA CAC CGG GCC CGG AGC GTC CGC GCT AGG

1700
L   L   A   R   G   G   R   A   A   I   C   G   K   Y   L
CTT CTG GCC AGA GGA GGC AGG GCT GCC ATA TGT GGC AAG TAC CTC 1710                                      1720
F   N   W   A   V   R   T   K   L   K   L   T   P   I   A
TTC AAC TGG GCA GTA AGA ACA AAG CTC AAA CTC ACT CCA ATA GCG

1730
A   A   G   Q   L   D   L   S   G   W   F   T   A   G   Y
GCC GCT GGC CAG CTG GAC TTG TTC GGC TGG TTC ACG GCT GGC TAC 1740                                          1750
S   G   G   D   I   Y   H   S   V   S   H   A   R   P   R
AGC GGG GGA GAC ATT TAT CAC AGC GTG TCT CAT GCC CGG CCC CGC

1760
W   I   W   F   C   L   L   L   L   A   A   G   V   G   I
TGG ATC TGG TTT TGC CTA CTC CTG CTT GCT GCA GGG GTA GGC ATC 1770                                      1780
Y   L   L   P   N   R   M   S   T   N   P   K   P   Q   R
TAC CTC CTC CCC AAC CGA ATG AGC ACG AAT CCT AAA CCT CAA AGA

1790
K   T   K   R   N   T   N   R   R   P   Q   D   V   K   F
AAG ACC AAA CGT AAC ACC AAC CGG CGG CCG CAG GAC GTC AAG TTC 1800                                  1810
P   G   G   G   Q   I   V   G   G   V   Y   L   L   P   R
CCG GGT GGC GGT CAG ATC GTT GGT GGA GTT TAC TTG TTG CCG CGC

1820
R   G   P   R   L   G   V   R   A   T   R   K   T   S   E
AGG GGC CCT AGA TTG GGT GTG CGC GCG ACG AGA AAG ACT TCC GAG 1830                                      1840
R   S   Q   P   R   G   R   R   Q   P   I   P   K   A   R
CGG TCG CAA CCT CGA GGT AGA CGT CAG CCT ATC CCC AAG GCT CGT

1850
R   P   E   G   R   T   W   A   Q   P   G   Y   P   W   P
CGG CCC GAG GGC AGG ACC TGG GCT CAG CCC GGG TAC CCT TGG CCC 1860                                  1870
L   Y   G   N   E   G   C   G   W   A   G   W   L   L   S
CTC TAT GGC AAT GAG GGC TGC GGG TGG GCG GGA TGG CTC CTG TCT

1880
P   R   G   S   R   P   S   W   G   P   T   D   P   R   R
CCC CGT GGC TCT CGG CCT AGC TGG GGC CCC ACA GAC CCC CGG CGT
```

FIG. 31

```
                       1890           1892
   R    S    R    N    L    G    K    OC
  AGG  TCG  CGC  AAT  TTG  GGT  AAG  TAA
```

FIG. 3J

```
                   NS5a
                   1973
                   SerGlySerTrpLeuArgAspIleTrpAspTrpIleCysGlu
                   TCCGGTTCCTGGCTAAGGGACATCTGGGACTGGATATGCGAG
                   AGGCCAAGGACCGATTCCCTGTAGACCCTGACCTATACGCTC

ValLeuSerAspPheLysThrTrpLeuLysAlaLysLeuMetProGlnLeuProGlyIle
GTGTTGAGCGACTTTAAGACCTGGCTAAAAGCTAAGCTCATGCCACAGCTGCCTGGGATC
CACAACTCGCTGAAATTCTGGACCGATTTTCGATTCGAGTACGGTGTCGACGGACCCTAG

ProPheValSerCysGlnArgGlyTyrLysGlyValTrpArgGlyAspGlyIleMetHis
CCCTTTGTGTCCTGCCAGCGCGGGTATAAGGGGGTCTGGCGAGGGGACGGCATCATGCAC
GGGAAACACAGGACGGTCGCGCCCATATTCCCCCAGACCGCTCCCCTGCCGTAGTACGTG

ThrArgCysHisCysGlyAlaGluIleThrGlyHisValLysAsnGlyThrMetArgIle
ACTCGCTGCCACTGTGGAGCTGAGATCACTGGACATGTCAAAAACGGGACGATGAGGATC
TGAGCGACGGTGACACCTCGACTCTAGTGACCTGTACAGTTTTTGCCCTGCTACTCCTAG

ValGlyProArgThrCysArgAsnMetTrpSerGlyThrPheProIleAsnAlaTyrThr
GTCGGTCCTAGGACCTGCAGGAACATGTGGAGTGGGACCTTCCCCATTAATGCCTACACC
CAGCCAGGATCCTGGACGTCCTTGTACACCTCACCCTGGAAGGGGTAATTACGGATGTGG

ThrGlyProCysThrProLeuProAlaProAsnTyrThrPheAlaLeuTrpArgValSer
ACGGGCCCCTGTACCCCCCTTCCTGCGCCGAACTACACGTTCGCGCTATGGAGGGTGTCT
TGCCCGGGGACATGGGGGGAAGGACGCGGCTTGATGTGCAAGCGCGATACCTCCCACAGA

AlaGluGluTyrValGluIleArgGlnValGlyAspPheHisTyrValThrGlyMetThr
GCAGAGGAATACGTGGAGATAAGGCAGGTGGGGGACTTCCACTACGTGACGGGTATGACT
CGTCTCCTTATGCACCTCTATTCCGTCCACCCCCTGAAGGTGATGCACTGCCCATACTGA

ThrAspAsnLeuLysCysProCysGlnValProSerProGluPhePheThrGluLeuAsp
ACTGACAATCTTAAATGCCCGTGCCAGGTCCCATCGCCCGAATTTTTCACAGAATTGGAC
TGACTGTTAGAATTTACGGGCACGGTCCAGGGTAGCGGGCTTAAAAAGTGTCTTAACCTG

GlyValArgLeuHisArgPheAlaProProCysLysProLeuLeuArgGluGluValSer
GGGGTGCGCCTACATAGGTTTGCGCCCCCCTGCAAGCCCTTGCTGCGGGAGGAGGTATCA
CCCCACGCGGATGTATCCAAACGCGGGGGGACGTTCGGGAACGACGCCCTCCTCCATAGT

PheArgValGlyLeuHisGluTyrProValGlySerGlnLeuProCysGluProGluPro
TTCAGAGTAGGACTCCACGAATACCCGGTAGGGTCGCAATTACCTTGCGAGCCCGAACCG
AAGTCTCATCCTGAGGTGCTTATGGGCCATCCCAGCGTTAATGGAACGCTCGGGCTTGGC

AspValAlaValLeuThrSerMetLeuThrAspProSerHisIleThrAlaGluAlaAla
GACGTGGCCGTGTTGACGTCCATGCTCACTGATCCCTCCCATATAACAGCAGAGGCGGCC
CTGCACCGGCACAACTGCAGGTACGAGTGACTAGGGAGGGTATATTGTCGTCTCCGCCGG

GlyArgArgLeuAlaArgGlySerProProSerValAlaSerSerSerAlaSerGlnLeu
GGGCGAAGGTTGGCGAGGGGATCACCCCCCTCTGTGGCCAGCTCCTCGGCTAGCCAGCTA
CCCGCTTCCAACCGCTCCCCTAGTGGGGGGAGACACCGGTCGAGGAGCCGATCGGTCGAT
```

FIGURE 5A

```
SerAlaProSerLeuLysAlaThrCysThrAlaAsnHisAspSerProAspAlaGluLeu
TCCGCTCCATCTCTCAAGGCAACTTGCACCGCTAACCATGACTCCCTGATGCTGAGCTC
AGGCGAGGTAGAGAGTTCCGTTGAACGTGGCGATTGGTACTGAGGGGACTACGACTCGAG

IleGluAlaAsnLeuLeuTrpArgGlnGluMetGlyGlyAsnIleThrArgValGluSer
ATAGAGGCCAACCTCCTATGGAGGCAGGAGATGGGCGGCAACATCACCAGGGTTGAGTCA
TATCTCCGGTTGGAGGATACCTCCGTCCTCTACCCGCCGTTGTAGTGGTCCCAACTCAGT

GluAsnLysValValIleLeuAspSerPheAspProLeuValAlaGluGluAspGluArg
GAAAACAAAGTGGTGATTCTGGACTCCTTCGATCCGCTTGTGGCGGAGGAGGACGAGCGG
CTTTTGTTTCACCACTAAGACCTGAGGAAGCTAGGCGAACACCGCCTCCTCCTGCTCGCC

GluIleSerValProAlaGluIleLeuArgLysSerArgArgPheAlaGlnAlaLeuPro
GAGATCTCCGTACCCGCAGAAATCCTGCGGAAGTCTCGGAGATTCGCCCAGGCCCTGCCC
CTCTAGAGGCATGGGCGTCTTTAGGACGCCTTCAGAGCCTCTAAGCGGGTCCGGGACGGG

ValTrpAlaArgProAspTyrAsnProProLeuValGluThrTrpLysLysProAspTyr
GTTTGGGCGCGGCCGGACTATAACCCCCCGCTAGTGGAGACGTGGAAAAAGCCCGACTAC
CAAACCCGCGCCGGCCTGATATTGGGGGGCGATCACCTCTGCACCTTTTTCGGGCTGATG

GluProProValValHisGlyCysProLeuProProProLysSerProProValProPro
GAACCACCTGTGGTCCATGGCTGCCCGCTTCCACCTCCAAAGTCCCCTCCTGTGCCTCCG
CTTGGTGGACACCAGGTACCGACGGGCGAAGGTGGAGGTTTCAGGGGAGGACACGGAGGC

ProArgLysLysArgThrValValLeuThrGluSerThrLeuSerThrAlaLeuAlaGlu
CCTCGGAAGAAGCGGACGGTGGTCCTCACTGAATCAACCCTATCTACTGCCTTGGCCGAG
GGAGCCTTCTTCGCCTGCCACCAGGAGTGACTTAGTTGGGATAGATGACGGAACCGGCTC

LeuAlaThrArgSerPheGlySerSerSerThrSerGlyIleThrGlyAspAsnThrThr
CTCGCCACCAGAAGCTTTGGCAGCTCCTCAACTTCCGGCATTACGGGCGACAATACGACA
GAGCGGTGGTCTTCGAAACCGTCGAGGAGTTGAAGGCCGTAATGCCCGCTGTTATGCTGT

ThrSerSerGluProAlaProSerGlyCysProProAspSerAspAlaGluSerTyrSer
ACATCCTCTGAGCCCGCCCCTTCTGGCTGCCCCCCCGACTCCGACGCTGAGTCCTATTCC
TGTAGGAGACTCGGGCGGGGAAGACCGACGGGGGGGCTGAGGCTGCGACTCAGGATAAGG

SerMetProProLeuGluGlyGluProGlyAspProAspLeuSerAspGlySerTrpSer
TCCATGCCCCCCCTGGAGGGGGAGCCTGGGGATCCGGATCTTAGCGACGGGTCATGGTCA
AGGTACGGGGGGGACCTCCCCCTCGGACCCCTAGGCCTAGAATCGCTGCCCAGTACCAGT

ThrValSerSerGluAlaAsnAlaGluAspValValCysCysSerMetSerTyrSerTrp
ACGGTCAGTAGTGAGGCCAACGCGGAGGATGTCGTGTGCTGCTCAATGTCTTACTCTTGG
TGCCAGTCATCACTCCGGTTGCGCCTCCTACAGCACACGACGAGTTACAGAATGAGAACC

ThrGlyAlaLeuValThrProCysAlaAlaGluGluGlnLysLeuProIleAsnAlaLeu
ACAGGCGCACTCGTCACCCCGTGCGCCGCGGAAGAACAGAAACTGCCCATCAATGCACTA
TGTCCGCGTGAGCAGTGGGGCACGCGGCGCCTTCTTGTCTTTGACGGGTAGTTACGTGAT

SerAsnSerLeuLeuArgHisHisAsnLeuValTyrSerThrThrSerArgSerAlaCys
AGCAACTCGTTGCTACGTCACCACAATTTGGTGTATTCCACCACCTCACGCAGTGCTTGC
TCGTTGAGCAACGATGCAGTGGTGTTAAACCACATAAGGTGGTGGAGTGCGTCACGAACG
```

FIGURE 5B

```
GlnArgGlnLysLysValThrPheAspArgLeuGlnValLeuAspSerHisTyrGlnAsp
CAAAGGCAGAAGAAAGTCACATTTGACAGACTGCAAGTTCTGGACAGCCATTACCAGGAC
GTTTCCGTCTTCTTTCAGTGTAAACTGTCTGACGTTCAAGACCTGTCGGTAATGGTCCTG

ValLeuLysGluValLysAlaAlaAlaSerLysValLysAlaAsnLeuLeuSerValGlu
GTACTCAAGGAGGTTAAAGCAGCGGCGTCAAAAGTGAAGGCTAACTTGCTATCCGTAGAG
CATGAGTTCCTCCAATTTCGTCGCCGCAGTTTTCACTTCCGATTGAACGATAGGCATCTC

GluAlaCysSerLeuThrProProHisSerAlaLysSerLysPheGlyTyrGlyAlaLys
GAAGCTTGCAGCCTGACGCCCCACACTCAGCCAAATCCAAGTTTGGTTATGGGGCAAAA
CTTCGAACGTCGGACTGCGGGGGTGTGAGTCGGTTTAGGTTCAAACCAATACCCCGTTTT

AspValArgCysHisAlaArgLysAlaValThrHisIleAsnSerValTrpLysAspLeu
GACGTCCGTTGCCATGCCAGAAAGGCCGTAACCCACATCAACTCCGTGTGGAAAGACCTT
CTGCAGGCAACGGTACGGTCTTTCCGGCATTGGGTGTAGTTGAGGCACACCTTTCTGGAA

LeuGluAspAsnValThrProIleAspThrThrIleMetAlaLysAsnGluValPheCys
CTGGAAGACAATGTAACACCAATAGACACTACCATCATGGCTAAGAACGAGGTTTTCTGC
GACCTTCTGTTACATTGTGGTTATCTGTGATGGTAGTACCGATTCTTGCTCCAAAAGACG

ValGlnProGluLysGlyGlyArgLysProAlaArgLeuIleValPheProAspLeuGly
GTTCAGCCTGAGAAGGGGGGTCGTAAGCCAGCTCGTCTCATCGTGTTCCCCGATCTGGGC
CAAGTCGGACTCTTCCCCCCAGCATTCGGTCGAGCAGAGTAGCACAAGGGGCTAGACCCG

ValArgValCysGluLysMetAlaLeuTyrAspValValThrLysLeuProLeuAlaVal
GTGCGCGTGTGCGAAAAGATGGCTTTGTACGACGTGGTTACAAAGCTCCCCTTGGCCGTG
CACGCGCACACGCTTTTCTACCGAAACATGCTGCACCAATGTTTCGAGGGGAACCGGCAC

MetGlySerSerTyrGlyPheGlnTyrSerProGlyGlnArgValGluPheLeuValGln
ATGGGAAGCTCCTACGGATTCCAATACTCACCAGGACAGCGGGTTGAATTCCTCGTGCAA
TACCCTTCGAGGATGCCTAAGGTTATGAGTGGTCCTGTCGCCCAACTTAAGGAGCACGTT

AlaTrpLysSerLysLysThrProMetGlyPheSerTyrAspThrArgCysPheAspSer
GCGTGGAAGTCCAAGAAAACCCCAATGGGGTTCTCGTATGATACCCGCTGCTTTGACTCC
CGCACCTTCAGGTTCTTTTGGGGTTACCCCAAGAGCATACTATGGGCGACGAAACTGAGG

ThrValThrGluSerAspIleArgThrGluGluAlaIleTyrGlnCysCysAspLeuAsp
ACAGTCACTGAGAGCGACATCCGTACGGAGGAGGCAATCTACCAATGTTGTGACCTCGAC
TGTCAGTGACTCTCGCTGTAGGCATGCCTCCTCCGTTAGATGGTTACAACACTGGAGCTG

ProGlnAlaArgValAlaIleLysSerLeuThrGluArgLeuTyrValGlyGlyProLeu
CCCCAAGCCCGCGTGGCCATCAAGTCCCTCACCGAGAGGCTTTATGTTGGGGGCCCTCTT
GGGGTTCGGGCGCACCGGTAGTTCAGGGAGTGGCTCTCCGAAATACAACCCCCGGGAGAA

ThrAsnSerArgGlyGluAsnCysGlyTyrArgArgCysArgAlaSerGlyValLeuThr
ACCAATTCAAGGGGGGAGAACTGCGGCTATCGCAGGTGCCGCGCGAGCGGCGTACTGACA
TGGTTAAGTTCCCCCCTCTTGACGCCGATAGCGTCCACGGCGCGCTCGCCGCATGACTGT

ThrSerCysGlyAsnThrLeuThrCysTyrIleLysAlaArgAlaAlaCysArgAlaAla
ACTAGCTGTGGTAACACCCTCACTTGCTACATCAAGGCCCGGGCAGCCTGTCGAGCCGCA
TGATCGACACCATTGTGGGAGTGAACGATGTAGTTCCGGGCCCGTCGGACAGCTCGGCGT
```

FIGURE 5C

```
GlyLeuGlnAspCysThrMetLeuValCysGlyAspAspLeuValValIleCysGluSer
GGGCTCCAGGACTGCACCATGCTCGTGTGTGGCGACGACTTAGTCGTTATCTGTGAAAGC
CCCGAGGTCCTGACGTGGTACGAGCACACACCGCTGCTGAATCAGCAATAGACACTTTCG

AlaGlyValGlnGluAspAlaAlaSerLeuArgAlaPheThrGluAlaMetThrArgTyr
GCGGGGGTCCAGGAGGACGCGGCGAGCCTGAGAGCCTTCACGGAGGCTATGACCAGGTAC
CGCCCCCAGGTCCTCCTGCGCCGCTCGGACTCTCGGAAGTGCCTCCGATACTGGTCCATG

SerAlaProProGlyAspProProGlnProGluTyrAspLeuGluLeuIleThrSerCys
TCCGCCCCCCCTGGGGACCCCCCACAACCAGAATACGACTTGGAGCTCATAACATCATGC
AGGCGGGGGGGACCCCTGGGGGGTGTTGGTCTTATGCTGAACCTCGAGTATTGTAGTACG

SerSerAsnValSerValAlaHisAspGlyAlaGlyLysArgValTyrTyrLeuThrArg
TCCTCCAACGTGTCAGTCGCCCACGACGGCGCTGGAAAGAGGGTCTACTACCTCACCCGT
AGGAGGTTGCACAGTCAGCGGGTGCTGCCGCGACCTTTCTCCCAGATGATGGAGTGGGCA

AspProThrThrProLeuAlaArgAlaAlaTrpGluThrAlaArgHisThrProValAsn
GACCCTACAACCCCCCTCGCGAGAGCTGCGTGGGAGACAGCAAGACACACTCCAGTCAAT
CTGGGATGTTGGGGGGAGCGCTCTCGACGCACCCTCTGTCGTTCTGTGTGAGGTCAGTTA

SerTrpLeuGlyAsnIleIleMetPheAlaProThrLeuTrpAlaArgMetIleLeuMet
TCCTGGCTAGGCAACATAATCATGTTTGCCCCCACACTGTGGGCGAGGATGATACTGATG
AGGACCGATCCGTTGTATTAGTACAAACGGGGGTGTGACACCCGCTCCTACTATGACTAC

ThrHisPhePheSerValLeuIleAlaArgAspGlnLeuGluGlnAlaLeuAspCysGlu
ACCCATTTCTTTAGCGTCCTTATAGCCAGGGACCAGCTTGAACAGGCCCTCGATTGCGAG
TGGGTAAAGAAATCGCAGGAATATCGGTCCCTGGTCGAACTTGTCCGGGAGCTAACGCTC

IleTyrGlyAlaCysTyrSerIleGluProLeuAspLeuProProIleIleGlnArgLeu
ATCTACGGGGCCTGCTACTCCATAGAACCACTGGATCTACCTCCAATCATTCAAAGACTC
TAGATGCCCCGGACGATGAGGTATCTTGGTGACCTAGATGGAGGTTAGTAAGTTTCTGAG

HisGlyLeuSerAlaPheSerLeuHisSerTyrSerProGlyGluIleAsnArgValAla
CATGGCCTCAGCGCATTTTCACTCCACAGTTACTCTCCAGGTGAAATCAATAGGGTGGCC
GTACCGGAGTCGCGTAAAAGTGAGGTGTCAATGAGAGGTCCACTTTAGTTATCCCACCGG

AlaCysLeuArgLysLeuGlyValProProLeuArgAlaTrpArgHisArgAlaArgSer
GCATGCCTCAGAAAACTTGGGGTACCGCCCTTGCGAGCTTGGAGACACCGGGCCCGGAGC
CGTACGGAGTCTTTTGAACCCCATGGCGGGAACGCTCGAACCTCTGTGGCCCGGGCCTCG

ValArgAlaArgLeuLeuAlaArgGlyGlyArgAlaAlaIleCysGlyLysTyrLeuPhe
GTCCGCGCTAGGCTTCTGGCCAGAGGAGGCAGGGCTGCCATATGTGGCAAGTACCTCTTC
CAGGCGCGATCCGAAGACCGGTCTCCTCCGTCCCGACGGTATACACCGTTCATGGAGAAG

AsnTrpAlaValArgThrLysLeuLysLeuThrProIleAlaAlaAlaGlyGlnLeuAsp
AACTGGGCAGTAAGAACAAAGCTCAAACTCACTCCAATAGCGGCCGCTGGCCAGCTGGAC
TTGACCCGTCATTCTTGTTTCGAGTTTGAGTGAGGTTATCGCCGGCGACCGGTCGACCTG

LeuSerGlyTrpPheThrAlaGlyTyrSerGlyGlyAspIleTyrHisSerValSerHis
TTGTCCGGCTGGTTCACGGCTGGCTACAGCGGGGGAGACATTTATCACAGCGTGTCTCAT
AACAGGCCGACCAAGTGCCGACCGATGTCGCCCCCTCTGTAAATAGTGTCGCACAGAGTA
```

FIGURE 5D

```
          2990core---------->
AlaArgProArgMetSerThrAsnProLysProGlnArgLysThrLysArgAsnThrAsn
GCCCGGCCCCGCATGAGCACGAATCCTAAACCTCAAAGAAAGACCAAACGTAACACCAAC
CGGGCCGGGGCGTACTCGTGCTTAGGATTTGGAGTTTCTTTCTGGTTTGCATTGTGGTTG ArgArgProGlnAspValLysPheProGlyGlyGlyGlnIleValGlyGlyValTyrLeu
CGGCGGCCGCAGGACGTCAAGTTCCCGGGTGGCGGTCAGATCGTTGGTGGAGTTTACTTG
GCCGCCGGCGTCCTGCAGTTCAAGGGCCCACCGCCAGTCTAGCAACCACCTCAAATGAAC LeuProArgArgGlyProArgLeuGlyValArgAlaThrArgLysThrSerGluArgSer
TTGCCGCGCAGGGGCCCTAGATTGGGTGTGCGCGCGACGAGAAAGACTTCCGAGCGGTCG
AACGGCGCGTCCCCGGGATCTAACCCACACGCGCGCTGCTCTTTCTGAAGGCTCGCCAGC GlnProArgGlyArgArgGlnProIleProLysAlaArgArgProGluGlyArgThrTrp
CAACCTCGAGGTAGACGTCAGCCTATCCCCAAGGCTCGTCGGCCCGAGGGCAGGACCTGG
GTTGGAGCTCCATCTGCAGTCGGATAGGGGTTCCGAGCAGCCGGGCTCCCGTCCTGGACC AlaGlnProGlyTyrProTrpProLeuTyrGlyAsnGluGlyCysGlyTrpAlaGlyTrp
GCTCAGCCCGGGTACCCTTGGCCCCTCTATGGCAATGAGGGCTGCGGGTGGGCGGGATGG
CGAGTCGGGCCCATGGGAACCGGGGAGATACCGTTACTCCCGACGCCCACCCGCCCTACC LeuLeuSerProArgGlySerArgProSerTrpGlyProThrAspProArgArgArgSer
CTCCTGTCTCCCCGTGGCTCTCGGCCTAGCTGGGGCCCCACAGACCCCCGGCGTAGGTCG
GAGGACAGAGGGGCACCGAGAGCCGGATCGACCCCGGGGTGTCTGGGGCCGCATCCAGC 121
ArgAsnLeuGlyLys
CGCAATTTGGGTAAG
GCGTTAAACCCATTC
```

FIGURE 5E

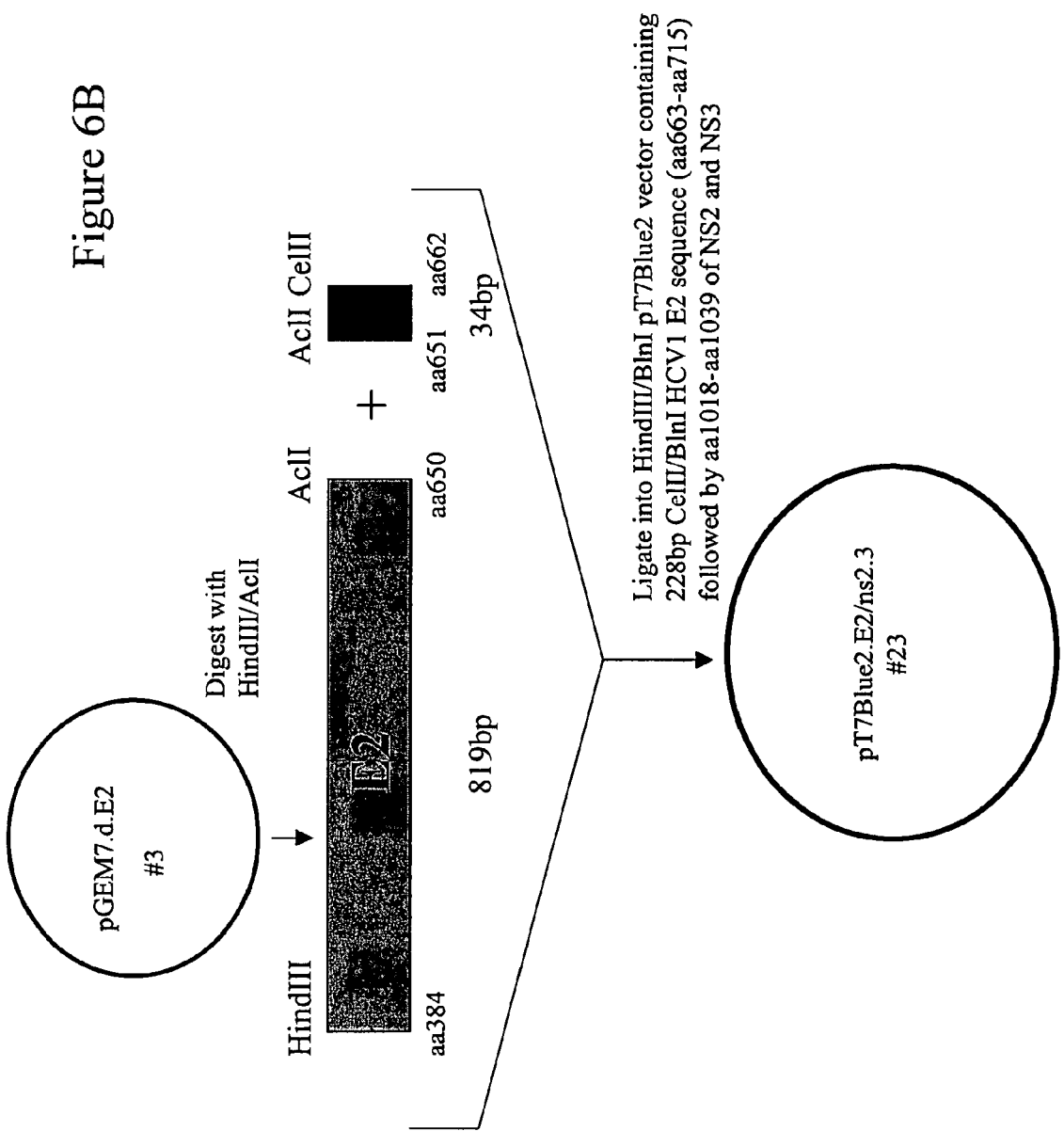

ST-See Blue Standard  
C-pAB24  
1-ns3m-ns5 (219.3 kD)  
2-ns3m-ns5 "  
3-ns3m-ns5tr (217.0 kD)  
4-ns3m-ns5tr "  
5-ns3m-ns5core121 (233.6 kD)  
6-ns3m-ns5core121 "  
7-ns3m-ns5tr.core121 (230.3 kD)  
8-ns3m-ns5tr.core121 "  
9-Δns3-ns5.core121 (208.0 kD)  
10-Δns3-ns5.core121 "

All samples represent the insoluble pellet (IP), resuspended in 1ml pH12 SB+DTT for 1hr and sonicated for ~8 seconds.

C-pAB24   3-e2.ns3m-ns5tr (253.6 kD)   7-e2.ns3m-ns5tr.core121 (266.3 kD)

ST-See Blue Standard   4-e2.ns3m-ns5tr   "   8-e2.ns3m-ns5tr.core121   "

1-e2.ns3m-ns5 (256.0 kD)   5-e2.ns3m-ns5core121 (269.2 kD)   9-Δns3-ns5.core121 (208.0 kD)

2-e2.ns3m-ns5   "   6-e2.ns3m-ns5core121   "   10-Δns3-ns5.core121   "

All samples represent the insoluble pellet IP, resuspended in 1ml pH12 SB+DTT for 1hr and sonicated for ~8 seconds.

ST-See Blue Standard  3-ns3m-ns5tr.core121(230.3 kD) 7-e2.ns3m-ns5tr.core121(266.3kD)

C-pAB24                  4-ns3m-ns5tr.core121        "           8-e2.ns3m-ns5tr.core121      "

1-ns3m-ns5 (219.3 kD)   5-e2.ns3m-ns5 (256.0 kD)    "           9-e2.ns3m-ns5tr.core121      "

2-ns3m-ns5        "      6-e2.ns3m-ns5              "          10-Δns3-ns5.core121 (208.0 kD)

All samples represent the IP, resuspended in 1ml pH12 SB+DTT for 1hr and sonicated for ~8 seconds. Inocula from *frozen glycerol stocks* (except pAB24).

ST-See Blue Standard  3-ns3m-ns5tr.core121 (230.3 kD)  6-e2.ns3m-ns5tr.core121 (266.3 kD)

C-pAB24  4-ns3m-ns5tr.core121  "  7-e2.ns3m-ns5tr.core121  "

1-ns3m-ns5 (219.3 kD)  ST-See Blue Standard  8-e2.ns3m-ns5tr.core121  "

2-ns3m-ns5  "  5-e2ns3m-ns5 (256.0 kD)

All samples represent the IP, resuspended in 1ml pH12 SB+DTT for 1hr and sonicated for ~8 seconds. Inocula from *liquid culture.*

HCV FUSION POLYPEPTIDES

CROSS REFERENCE TO RELATED APPLICATIONS

This application is a §371 filing from PCT/US2007/018940, filed Aug. 27, 2007, and claims the benefit under 35 U.S.C. §119(e)(1) of U.S. Provisional Application No. 60/840,162, filed Aug. 25, 2006, which is applications are incorporated herein by reference in their entireties and from which applications priority is claimed pursuant to the provisions of 35 U.S.C. §§119/120.

TECHNICAL FIELD

The present invention relates to hepatitis C virus (HCV) polypeptides. More particularly, the invention relates to nucleic acids and proteins wherein the nucleic acids encode truncated HCV fusion proteins comprising E2, a portion of the carboxy terminus of NS2, a mutated NS3, NS4, a truncated NS5 and optionally a core polypeptide from HCV. The proteins are useful for stimulating immune responses, such as cell-mediated immune responses, for priming and/or activating HCV-specific T cells, as well as for diagnostic reagents. The invention also relates to methods of enhancing production of HCV fusion polypeptide.

BACKGROUND OF THE INVENTION

Hepatitis C virus (HCV) infection is an important health problem with approximately 1% of the world's population infected with the virus. Over 75% of acutely infected individuals eventually progress to a chronic carrier state that can result in cirrhosis, liver failure, and hepatocellular carcinoma. See, Alter et al. (1992) N. Engl. J. Med. 327:1899-1905; Resnick and Koff. (1993) Arch. Intem. Med. 153:1672-1677; Seeff (1995) Gastrointest. Dis. 6:20-27; Tong et al. (1995) N. Engl. J. Med. 332:1463-1466.

HCV was first identified and characterized as a cause of NANBH by Houghton et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391-2399). The virus encodes a single polyprotein having more than 3000 amino acid residues (Choo et al., *Science* (1989) 244:359-362; Choo et al., *Proc. Natl. Acad. Sci. USA* (1991) 88:2451-2455; Han et al., *Proc. Natl. Acad. Sci. USA* (1991) 88:1711-1715). The polyprotein is processed co- and post-translationally into both structural and non-structural (NS) proteins.

In particular, as shown in FIG. 1, several proteins are encoded by the HCV genome. The order and nomenclature of the cleavage products of the HCV polyprotein is as follows: $NH_2$-C-E1-E2-p7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, "E1" (also known as E) and "E2" (also known as E2/NS1), as well as nonstructural (NS) proteins that contain the viral enzymes. The NS regions are termed NS2, NS3, NS4 and NS5. NS2 is an integral membrane protein with proteolytic activity and, in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. In these reactions, NS3 liberates an NS3 cofactor (NS4a), two proteins (NS4b and NS5a), and an RNA-dependent RNA polymerase (NS5b). Completion of polyprotein maturation is initiated by autocatalytic cleavage at the NS3-NS4a junction, catalyzed by the NS3 serine protease.

Despite extensive advances in the development of pharmaceuticals against certain viruses like HIV, control of acute and chronic HCV infection has had limited success (Hoofnagle and di Bisceglie (1997) N. Engl. J. Med. 336:347-356). In particular, generation of cellular immune responses, such as strong cytotoxic T lymphocyte (CTL) responses, is thought to be important for the control and eradication of HCV infections.

Immunogenic HCV fusion proteins capable of generating cellular immune responses are described in International Application WO/2004/005473 and U.S. Pat. Nos. 6,562,346; 6,514,731 and 6,428,792. Nevertheless, there remains a need in the art for additional effective methods of stimulating immune responses, such as cellular immune responses, to HCV.

SUMMARY OF THE INVENTION

It is an object of the invention to provide reagents and methods for stimulating an immune response, such as a cellular immune response to HCV, such as priming and/or activating T cells which recognize epitopes of HCV polypeptides. It is also an object of the invention to provide compositions for the prevention and/or treatment of HCV infection. It is also an object of the invention to provide reagents and methods for use in diagnostic assays for detecting the presence of HCV in a biological sample.

Accordingly, in one embodiment, the invention is directed to an immunogenic composition comprising an isolated HCV fusion polypeptide consisting of, in an amino terminal to carboxy terminal direction, a methionine, amino acids 384 to 715 of E2, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a lysine and amino acid 11 of the core sequence is asparagine.

In another embodiment, the invention is directed to an immunogenic composition comprising an isolated HCV fusion polypeptide consisting of, in an amino terminal to carboxy terminal direction, a methionine, amino acids 384 to 715 of E2, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a lysine and amino acid 11 of the core sequence is asparagine.

In another embodiment, the invention is directed to an immunogenic composition comprising an isolated HCV fusion polypeptide consisting of, in an amino terminal to carboxy terminal direction, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a lysine and amino acid 11 of the core sequence is asparagine.

In yet another embodiment, the invention is directed to an immunogenic composition comprising an isolated HCV fusion polypeptide consisting of in an amino terminal to carboxy terminal direction, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a lysine and amino acid 11 of the core sequence is asparagine.

In further embodiments, the invention is directed to an immunogenic composition comprising an isolated HCV fusion polypeptide consisting of, in an amino terminal to carboxy terminal direction, a methionine, amino acids 384 to 715 of E2, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a arginine and amino acid 11 of the core sequence is threonine.

In another embodiment, the invention is directed to an immunogenic composition comprising an isolated HCV fusion polypeptide consisting of, in an amino terminal to carboxy terminal direction, a methionine, amino acids 384 to 715 of E2, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a arginine and amino acid 11 of the core sequence is threonine.

In another embodiment, the invention is directed to an immunogenic composition comprising an isolated HCV fusion polypeptide consisting of, in an amino terminal to carboxy terminal direction, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a arginine and amino acid 11 of the core sequence is threonine.

In yet another embodiment, the invention is directed to an immunogenic composition comprising an isolated HCV fusion polypeptide consisting of, in an amino terminal to carboxy terminal direction, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a arginine and amino acid 11 of the core sequence is threonine.

In a separate embodiment, the invention comprises a nucleic acid encoding a HCV fusion polypeptide of the invention.

All HCV protein regions (eg, E2, NS2, NS3, NS4, NS5, core) are numbered relative to the amino acid sequence of the full-length HCV-1 polyprotein.

In additional embodiments, the HCV polypeptides present in the fusion polypeptide are derived from the same HCV isolate. In other embodiments, at least one of the HCV polypeptides present in the fusion is derived from a different isolate than at least one of the other peptides present in the fusion.

In certain embodiments, the HCV fusion polypeptides comprise an HCV core polypeptide that comprises a C-terminal truncation, such a core polypeptide that consists of the sequence of amino acids depicted at amino acid positions 1772-1892 of FIG. 3A-3J.

In yet further embodiments, the invention is directed to a composition comprising a HCV fusion polypeptide according to any of the embodiments above in combination with a pharmaceutically acceptable excipient. In certain embodiments, the compositions include an immunogenic HCV polypeptide, such as an HCV E1E2 complex. The E1E2 complex can be provided separately from the fusion protein.

In additional embodiments, the invention is directed to a method of stimulating a cellular immune response in a vertebrate subject comprising administering to the subject a therapeutically effective amount of a composition as described above.

In further embodiments, the invention is directed to a recombinant vector comprising:

(a) a polynucleotide encoding one or more of the HCV fusion polypeptides as described above; and (b) at least one control element operably linked to the polynucleotide, whereby the coding sequence can be transcribed and translated in a host cell.

In additional embodiments, the invention is directed to a host cell comprising the recombinant vector described above.

In further embodiments, the invention is directed to a method for producing an HCV fusion polypeptide, the method comprising culturing a population of host cells as described above under conditions for producing the protein. The invention also includes a method for enhancing the recombinant expression of an HCV fusion polypeptide by positioning HCV E2 amino acid sequences at the N-terminal of the fusion polypeptide.

These and other embodiments of the subject invention will readily occur to those of skill in the art in view of the disclosure herein.

BRIEF DESCRIPTION OF THE FIGURES

FIG. 2 (SEQ ID NOS:3 and 4) depicts the DNA and corresponding amino acid sequence of a representative native, unmodified NS3 protease domain.

FIG. 3A-3J (SEQ ID NOS:5 and 6) shows the DNA and corresponding amino acid sequence of a region of a representative modified fusion protein, with the NS3 protease domain deleted from the N-terminus and including amino acids 1-121 of Core on the C-terminus.

FIG. 4A shows expression levels at 25° C. and FIG. 4B shows expression levels at 30° C. Lane 1, standard; Lane 2, plasmid control; Lane 3, plasmid encoding NS5tCore121 (clone 6); Lane 4, plasmid encoding NS5tCore121 (clone 7); Lane 5, plasmid encoding NS5Core121 (clone 8); Lane 6, plasmid encoding NS5Core121 (clone 9); Lane 7, standard.

FIGS. 5A-5E (SEQ ID NOS:7 and 8) show the DNA and corresponding amino acid sequence of a region of a representative fusion protein that includes a C-terminally truncated NS5 polypeptide with the C-terminus of the NS5 polypeptide fused to a core polypeptide. In particular, the C-terminally truncated NS5 polypeptide includes amino acids 1973-2990 of the HCV polyprotein, numbered relative to HCV-1 (see, Choo et al. (1991) *Proc. Natl. Acad. Sci. USA* 88:2451-2455), fused to a core polypeptide that includes amino acids 1-121 of the HCV polyprotein.

FIGS. 6A through 6F depict an exemplary cloning strategy used to generate fusion polypeptides of the present invention.

DETAILED DESCRIPTION OF THE INVENTION

Figure 1:
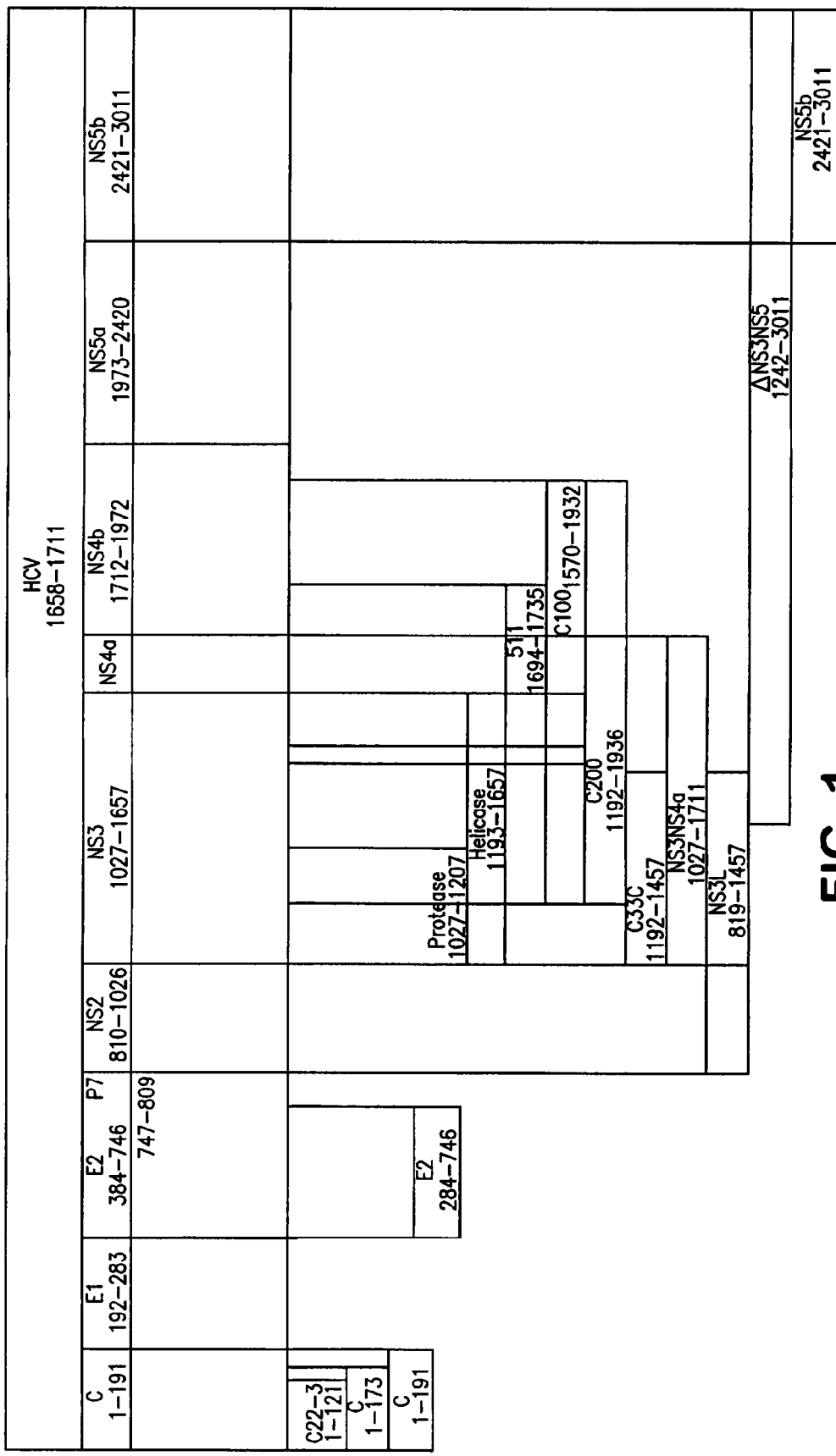
FIG. 1 is a diagrammatic representation of the HCV genome, depicting the various regions of the HCV polyprotein.
Figure 4:
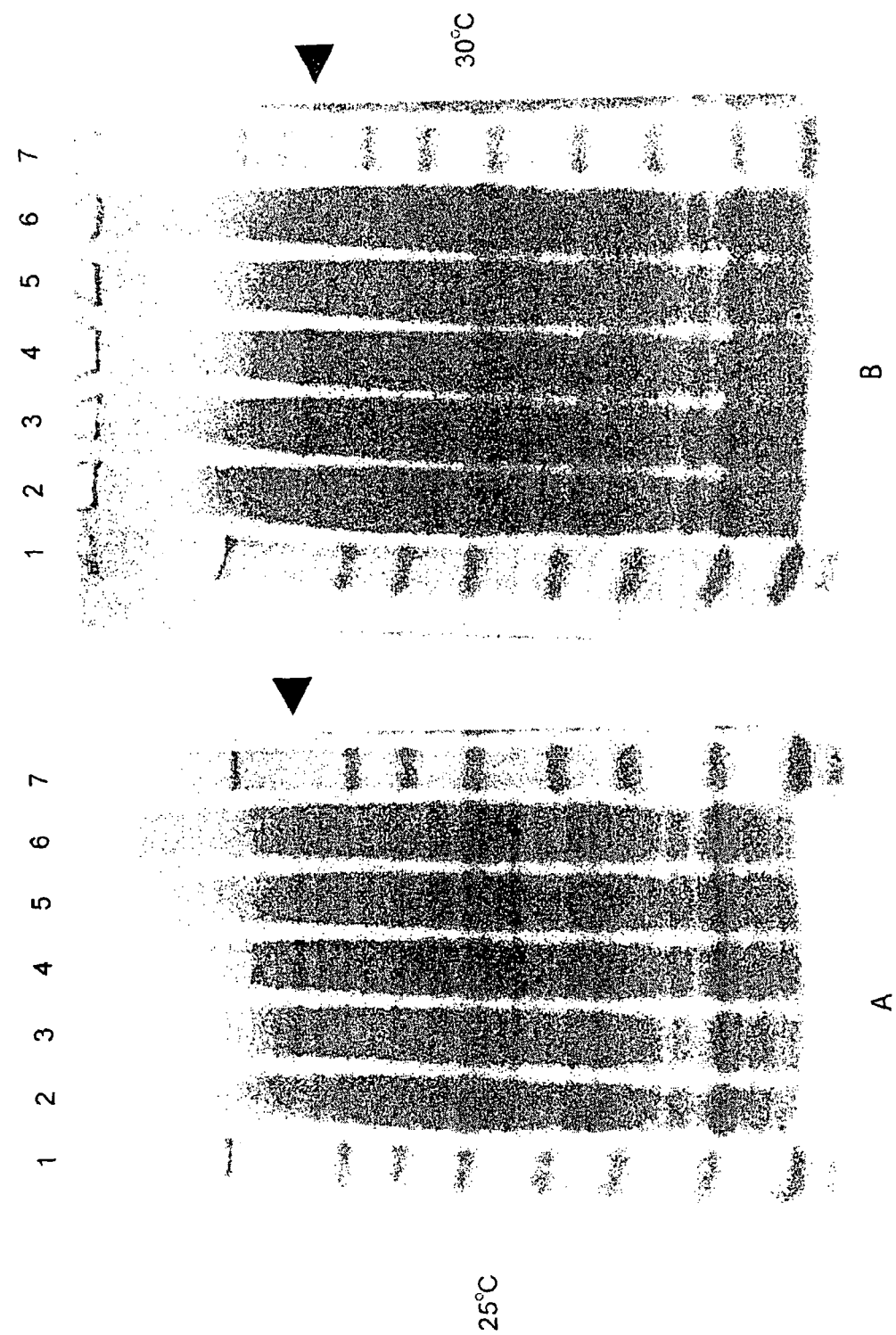
FIGS. 4A and 4B show a comparison of expression levels of NS5tCore121 (amino acids 1973-2990 of NS5 and 1-121 of core) and NS5Core121 (full-length NS5, amino acids 1973-3011 of NS5 and 1-121 of core) in S. cerevisiae strain AD3.

The practice of the present invention will employ, unless otherwise indicated, conventional methods of chemistry, biochemistry, recombinant DNA techniques and immunology, within the skill of the art. Such techniques are explained fully in the literature. See, e.g., Sambrook, et al., *Molecular Cloning: A Laboratory Manual* (2nd Edition); *Methods In Enzymology* (S. Colowick and N. Kaplan eds., Academic Press, Inc.); *DNA Cloning*, Vols. I and II (D. N. Glover ed.); *Oligonucleotide Synthesis* (M. J. Gait ed.); *Nucleic Acid Hybridization* (B. D. Hames & S. J. Higgins eds.); *Animal Cell Culture* (R. K. Freshney ed.); Perbal, B., *A Practical Guide to Molecular Cloning*.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: H is (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An "HCV polypeptide" is a polypeptide, as defined above, derived from the HCV polyprotein. The polypeptide need not be physically derived from HCV, but may be synthetically or recombinantly produced. Moreover, the polypeptide may be derived from any of the various HCV strains and isolates including isolates having any of the 6 genotypes of HCV described in Simmonds et al., *J. Gen. Virol.* (1993) 74:2391-2399 (e.g., strains 1, 2, 3, 4 etc.), as well as newly identified isolates, and subtypes of these isolates, such as HCV1a, HCV1b etc. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS5" polypeptide refers to native NS5 from any of the various HCV strains, as well as NS5 analogs, muteins and immunogenic fragments, as defined further below. The term "HCV polypeptide" will generally be used to refer to the various individual identified and well-known HCV proteins present in the HCV polyprotein, that is core, E1, E2, p7, NS2, NS3, NS4 (including NS4a and NS4b), NS5 (including NS5a and NS5b). The term "HCV fusion polypeptide" will be used to refer to a recombinant polypeptide in which two or more of the HCV polypeptides are present in a single recombinant polypeptide molecule.

The terms "analog" and "mutein" refer to biologically active derivatives of the reference molecule, or fragments of such derivatives, that retain desired activity, such as the ability to stimulate a cell-mediated immune response, as defined below. In the case of a modified NS3, an "analog" or "mutein" refers to an NS3 molecule that lacks its native proteolytic activity. In general, the term "analog" refers to compounds having a native polypeptide sequence and structure with one or more amino acid additions, substitutions (generally conservative in nature, or in the case of modified NS3, non-conservative in nature at the active proteolytic site) and/or deletions, relative to the native molecule, so long as the modifications do not destroy immunogenic activity. The term "mutein" refers to peptides having one or more peptide mimics ("peptoids"). Preferably, the analog or mutein has at least the same immunoactivity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact.

One of skill in the art may readily determine regions of the molecule of interest that can tolerate change by reference to Hopp/Woods and Kyte-Doolittle plots, well known in the art.

By "C-terminally truncated NS5 polypeptide" is meant an NS5 polypeptide that comprises a full-length NS5a polypeptide and an N-terminal portion of an NS5b polypeptide, but not the entire NS5b region. Particular examples of C-terminally truncated NS5 polypeptides are provided below.

By "modified NS3" is meant an NS3 polypeptide with a modification such that protease activity of the NS3 polypeptide is disrupted, that is to say the protease activity is reduced, inhibited or absent (compared with the non-modified or wild type NS3). The modification can include one or more amino acid additions, substitutions (generally non-conservative in nature) and/or deletions, relative to the native molecule, wherein the protease activity of the NS3 polypeptide is disrupted. Methods of measuring protease activity are discussed further below.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunogenic activity, as measured by the assays described herein.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

For a description of various HCV epitopes, see, e.g., Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D.Y., International Publication No. WO 94/01778; and U.S. Pat. Nos. 6,280,927 and 6,150,087.

As used herein the term "T-cell epitope" refers to a feature of a peptide structure which is capable of inducing T-cell immunity towards the peptide structure or an associated hapten. T-cell epitopes generally comprise linear peptide determinants that assume extended conformations within the peptide-binding cleft of MHC molecules, (Unanue et al., *Science* (1987) 236:551-557). Conversion of polypeptides to MHC class II-associated linear peptide determinants (generally between 5-14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc, ed. G. C. Woodrow et al., (1990) pp. 109-116) and further that the amphipathic structures have an $\alpha$-helical configuration (see, e.g., Spouge et al., *J. Immunol.* (1987) 138:204-212; Berkower et al., *J. Immunol.* (1986) 136:2498-2503).

Hence, segments of proteins that include T-cell epitopes can be readily predicted using numerous computer programs. (See e.g., Margalit et al., *Computer Prediction of T-cell Epitopes, New Generation Vaccines* Marcel-Dekker, Inc, ed. G. C. Woodrow et al., (1990) pp. 109-116). Such programs generally compare the amino acid sequence of a peptide to sequences known to induce a T-cell response, and search for patterns of amino acids which are believed to be required for a T-cell epitope.

An "immunological response" to an HCV antigen (including both polypeptide and polynucleotides encoding polypeptides that are expressed in vivo) or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T lymphocytes and/or other white blood cells. One important aspect of cellular immunity involves an antigen-specific response by cytolytic T cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Both CD8+ and CD4+ T cells are capable of killing HCV-infected cells. Another aspect of cellular immunity involves an antigen-specific response by helper T cells. Helper T cells act to help stimulate the function, and focus the activity of, nonspecific effector cells against cells displaying peptide antigens in association with MHC molecules on their surface. A "cellular immune response" also refers to the production of antiviral cytokines, chemokines and other such molecules produced by activated T cells and/or other white blood cells, including those derived from CD4+ and CD8+ T cells, including, but not limited to IFN-γ and TNF-α.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T cells. The antigen of interest may also elicit an antibody-mediated immune response. Hence, an immunological response may include one or more of the following effects: the production of antibodies by B-cells; and/or the activation of suppressor T cells and/or γδ T cells directed specifically to an antigen or antigens present in the composition or vaccine of interest. These responses may serve to neutralize infectivity, and/or mediate antibody-complement, or antibody dependent cell cytotoxicity (ADCC) to provide protection (i.e., prophylactic) or alleviation of symptoms (i.e., therapeutic) to an immunized host. Such responses can be determined using standard immunoassays and neutralization assays, well known in the art.

By "equivalent antigenic determinant" is meant an antigenic determinant from different sub-species or strains of HCV, such as from strains 1, 2, 3, etc., of HCV which antigenic determinants are not necessarily identical due to sequence variation, but which occur in equivalent positions in the HCV sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of biological macromolecules of the same type are present.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98%, or more, sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be readily found at the NCBI Internet site.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By "nucleic acid immunization" is meant the introduction of a nucleic acid molecule encoding one or more selected immunogens into a host cell, for the in vivo expression of the immunogen or immunogens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes Of Carrying Out The Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

The present invention pertains to HCV fusion polypeptides that comprise amino acids 1018 to 1026 of HCV NS2, full-length HCV NS5a polypeptide and a portion of an HCV NS5b polypeptide with a C-terminal truncation. The invention also relates to polynucleotides encoding the same. In particular, the HCV fusion polypeptides of the invention include, in order from the amino terminal to the carboxy terminal, amino acids 1018 to 1026 of HCV NS2, amino acids 1027 to 1657 of HCV NS3, amino acids 1658 to 1972 of HCV NS4, amino acids 1973 to 2990 of NS5 and amino acids 1 to 121 of core. The HCV fusion polypeptide can additionally include amino acids 384 to 715 of HCV E2 at the amino terminal preceding the NS2 sequence, and/or amino acids 2991 to 3011 of HCV NS5 immediately following the NS5 2990 amino acid. The HCV fusion polypeptides of the present invention can be used to stimulate immunological responses, such as a humoral and/or cellular immune response, for example to activate HCV-specific T cells, i.e., T cells which recognize epitopes of these polypeptides and/or to elicit the production of helper T cells and/or to stimulate the production of antiviral cytokines, chemokines, and the like. Activation of HCV-specific T cells by such fusion proteins provides both in vitro and in vivo model systems for the development of HCV vaccines, particularly for identifying HCV polypeptide epitopes associated with a response. The HCV fusion polypeptides can also be used to generate an immune response against HCV in a mammal, for example a CTL response, and/or to prime CD8+ and CD4+ T cells to produce antiviral agents, for either therapeutic or prophylactic purposes.

The HCV fusion polypeptides are therefore useful for treating and/or preventing HCV infection. The HCV fusion polypeptides can be used alone or in combination with one or more bacterial or viral immunogens. The combinations may include multiple immunogens from the same pathogen, multiple immunogens from different pathogens or multiple immunogens from the same and from different pathogens. Thus, bacterial, viral, and/or other immunogens may be included in the same composition as the HCV fusion polypeptides, or may be administered to the same subject separately.

Moreover, the HCV fusion polypeptides of the present invention can also be used as diagnostic reagents to detect HCV infection in a biological sample.

In order to further an understanding of the invention, a more detailed discussion is provided below regarding HCV fusion polypeptides for use in the subject compositions, as well as production of the HCV fusion polypeptides, compositions comprising the same and methods of using the HCV fusion polypeptides.

HCV Fusion Polypeptides

The genomes of HCV strains contain a single open reading frame of approximately 9,000 to 12,000 nucleotides, which is transcribed into a polyprotein. As shown in FIG. 1 and Table 1, an HCV polyprotein, upon cleavage, produces at least ten distinct products, in the order of $NH_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) Proc. Natl. Acad. Sci. USA 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, in combination with NS3, (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011). Completion of polyprotein maturation is initiated by autocatalytic cleavage at the NS3-NS4a junction, catalyzed by the NS3 serine protease.

TABLE 1

| Domain | Approximate Boundaries* |
|---|---|
| C (core) | 1-191 |
| E1 | 192-383 |
| E2 | 384-746 |
| P7 | 747-809 |
| NS2 | 810-1026 |
| NS3 | 1027-1657 |
| NS4a | 1658-1711 |
| NS4b | 1712-1972 |
| NS5a | 1973-2420 |
| NS5b | 2421-3011 |

*Numbered relative to HCV-1. See, Choo et al. (1991) Proc. Natl. Acad. Sci. USA 88: 2451-2455.

HCV fusion polypeptides of the invention include a C-terminally truncated NS5 polypeptide (also referred to herein as "NS5t" or "NS5tr"). In particular, the C-terminally truncated NS5 polypeptide comprises a full-length NS5a polypeptide and an N-terminal portion of an NS5b polypeptide. The C-terminally truncated polypeptide can be truncated at any position between amino acid 2500 and the C-terminus, numbered relative to the full-length HCV-1 polyprotein, such as after amino acid 2505 . . . 2550 . . . 2600 . . . 2650 . . . 2700 . . . 2750 . . . 2800 . . . 2850 . . . 2900 . . . 2950 . . . 2960 . . . 2970 . . . 2975 . . . 2980 . . . 2985 . . . 2990 . . . 2995 . . . 3000, etc, numbered relative to the full-length HCV-1 sequence. It is readily apparent that the molecule can be truncated at any amino acid between 2500 and 3010, numbered relative to the full-length HCV-1 sequence. One particularly preferred NS5 polypeptide is truncated at the amino acid corresponding to the amino acid immediately following amino acid 2990, numbered relative to the full-length HCV-1 polyprotein, and comprises an amino acid sequence corresponding to amino acids 1973-2990, numbered relative to the full-length HCV-1 polyprotein. The sequence for such a construct is shown at amino acid positions 1-1018 of SEQ ID NO:8 (labeled as amino acids 1973-2990 in FIGS. 5A-5E). The fusions of the invention optionally have an N-terminal methionine for expression.

The C-terminally truncated NS5 polypeptides can be used alone, in compositions described below, or in combination with one or more other HCV immunogenic polypeptides derived from any of the various domains of the HCV polyprotein. The additional HCV polypeptides can be provided separately or in the fusion. In fact, the fusion can include all the regions of the HCV polyprotein. These polypeptides may be derived from the same HCV isolate as the NS5 polypeptide, or from different strains and isolates including isolates having any of the various HCV genotypes, to provide increased protection against a broad range of HCV genotypes. Additionally, polypeptides can be selected based on the particular viral clades endemic in specific geographic regions where vaccine compositions containing the fusions will be used. It is readily apparent that the subject fusions provide an effective means of treating HCV infection in a wide variety of contexts.

Thus, NS5t can be included in a fusion polypeptide comprising any combination of NS5t with one or more immunogenic HCV polypeptide from other domains in the HCV polyprotein, i.e., an NS5t combined with an E1, E2, p7, NS2, NS3, NS4, and/or a core polypeptide. Preferably, the NS5t is combined with portions of the NS2, NS3, NS4, and core polypeptides, and optionally E2, in a HCV fusion polypeptide. These regions need not be in the order in which they occur naturally. Moreover, each of these regions can be derived from the same or a different HCV isolate. The various HCV polypeptides present in the various fusions described herein can either be full-length polypeptides or portions thereof.

The portions of the HCV polypeptides making up the fusion polypeptide each generally comprise at least one epitope, which is recognized by a T cell receptor on an activated T cell, such as 2152-HEYPVGSQL-2160 (SEQ ID NO:1) and/or 2224-AELIEANLLWRQEMG-2238 (SEQ ID NO:2). Epitopes can be identified by several methods. For example, the individual polypeptides or fusion proteins comprising any combination of the above, can be isolated by, e.g., immunoaffinity purification using a monoclonal antibody for the polypeptide or protein. The isolated protein sequence can then be screened by preparing a series of short peptides by proteolytic cleavage of the purified protein, which together span the entire protein sequence. By starting with, for example, 100-mer polypeptides, each polypeptide can be tested for the presence of epitopes recognized by a T-cell receptor on an HCV-activated T cell, progressively smaller and overlapping fragments can then be tested from an identified 100-mer to map the epitope of interest.

Epitopes recognized by a T-cell receptor on an HCV-activated T cell can be identified by, for example, a $^{51}$Cr release assay or by a lymphoproliferation assay (see the examples). In a $^{51}$Cr release assay, target cells can be constructed that display the epitope of interest by cloning a polynucleotide encoding the epitope into an expression vector and transforming the expression vector into the target cells. HCV-specific CD8$^+$ T cells will lyse target cells displaying, for example, one or more epitopes from one or more regions of the HCV polyprotein found in the fusion, and will not lyse cells that do not display such an epitope. In a lymphoproliferation assay, HCV-activated CD4$^+$ T cells will proliferate when cultured with, for example, one or more epitopes from one or more regions of the HCV polyprotein found in the fusion, but not in the absence of an HCV epitopic peptide.

The various HCV polypeptides can occur in any order in the fusion polypeptide. If desired, at least 2, 3, 4, 5, 6, 7, 8, 9, or 10 or more of one or more of the HCV polypeptides may occur in the HCV fusion polypeptide. Multiple viral strains of HCV occur, and HCV polypeptides of any of these strains can be used in the fusion polypeptide.

Nucleic acid and amino acid sequences of a number of HCV strains and isolates, including nucleic acid and amino acid sequences of the various regions of the HCV polyprotein, including Core, NS2, p7, E1, E2, NS3, NS4, NS5a, NS5b genes and polypeptides have been determined. For example, isolate HCV J1.1 is described in Kubo et al. (1989) Japan. Nucl. Acids Res. 17:10367-10372; Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al. (1990) Proc. Natl. Acad. Sci. USA 87:9524-9528 and Takamizawa et al., (1991) J. Virol. 65:1105-1113 respectively.

Publications that describe HCV-1 isolates include Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254.

As explained above, each of the components of an HCV fusion polypeptide can be obtained from the same HCV strain or isolate or from different HCV strains or isolates. For example, the NS5 polypeptide can be derived from a first strain of HCV, and the other HCV polypeptides present can be derived from a second strain of HCV. Alternatively, one or more of the other HCV polypeptides, for example NS2, NS3, NS4, Core, p'7, E1 and/or E2, if present, can be derived from a first strain of HCV, and the remaining HCV polypeptides can be derived from a second strain of HCV. Additionally, each or the HCV polypeptides present can be derived from different HCV strains.

For a description of various HCV epitopes from the HCV regions for use in the subject fusions, see, e.g., Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and U.S. Pat. Nos. 6,280,927 and 6,150,087.

For example, fusions can comprise the C-terminally truncated NS5 polypeptide and an NS3 polypeptide. The NS3 polypeptide can be modified to inhibit or reduce protease activity, such that further cleavage of the fusion is inhibited (also referred to herein as "NS3*"). The NS3 polypeptide can be modified by deletion of all or a portion of the NS3 protease domain. Alternatively, proteolytic activity can be inhibited by substitutions of amino acids within active regions of the protease domain. Finally, additions of amino acids to active regions of the domain, such that the catalytic site is modified, will also serve to inhibit proteolytic activity.

As explained above, the protease activity is found at about amino acid positions 1027-1207, numbered relative to the full-length HCV-1 polyprotein (see, Choo et al., *Proc. Natl. Acad. Sci. USA* (1991) 88:2451-2455), positions 2-182 of FIG. 2. The structure of the NS3 protease and active site are known. See, e.g., De Francesco et al., *Antivir. Ther.* (1998) 3:99-109; Koch et al., *Biochemistry* (2001) 40:631-640. Thus, deletions or modifications to the native sequence will typically occur at or near the active site of the molecule. Particularly, it is desirable to modify or make deletions to one or more amino acids occurring at positions 1- or 2-182, preferably 1- or 2-170, or 1- or 2-155 of FIG. 2. Preferred modifications are to the catalytic triad at the active site of the protease, i.e., H, D and/or S residues, in order to inactivate the protease. These residues occur at positions 1083, 1107 and 1165, respectively, numbered relative to the full-length HCV polyprotein (positions 58, 80 and 140, respectively, of FIG. 2). Such modifications will suppress proteolytic cleavage while maintaining T-cell epitopes. One particularly preferred modification is a substitution of Ser-1165 with Ala. One of skill in the art can readily determine portions of the NS3 protease to delete in order to disrupt activity. The presence or absence of activity can be determined using methods known to those of skill in the art.

For example, protease activity or lack thereof may be determined using the procedure described below in the examples, as well as using assays well known in the art. See, e.g., Takeshita et al., *Anal. Biochem.* (1997) 247:242-246; Kakiuchi et al., *J. Biochem.* (1997) 122:749-755; Sali et al., *Biochemistry* (1998) 37:3392-3401; Cho et al., *J. Virol. Meth.* (1998) 72:109-115; Cerretani et al., *Anal. Biochem.* (1999) 266:192-197; Zhang et al., *Anal. Biochem.* (1999) 270:268-275; Kakiuchi et al., *J. Virol. Meth.* (1999) 80:77-84; Fowler et al., *J. Biomol. Screen.* (2000) 5:153-158; and Kim et al., *Anal. Biochem.* (2000) 284:42-48.

FIG. 3A-3J shows a representative HCV fusion polypeptide containing modified NS3 polypeptide, with the NS3 protease domain deleted from the N-terminus and including amino acids 1-121 of Core on the C-terminus.

As explained above, it may be desirable to include polypeptides derived from the core region of the HCV polyprotein in the fusions of the invention. This region occurs at amino acid positions 1-191 of the HCV polyprotein, numbered relative to HCV-1. Either the full-length protein, fragments thereof, such as amino acids 1-160, e.g., amino acids 1-150, 1-140, 1-130, 1-120, for example, amino acids 1-121, 1-122, 1-123 . . . 1-151, etc., or smaller fragments containing epitopes of the full-length protein may be used in the subject fusions, such as those epitopes found between amino acids 10-53, amino acids 10-45, amino acids 67-88, amino acids 120-130, or any of the core epitopes identified in, e.g., Houghton et al., U.S. Pat. No. 5,350,671; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and U.S. Pat. Nos. 6,280,927 and 6,150,087. Moreover, a protein resulting from a frameshift in the core region of the polyprotein, such as described in International Publication No. WO 99/63941, may be used. One particularly desirable core polypeptide for use with the present fusions includes the sequence of amino acids depicted at amino acid positions 1772-1892 of FIG. 3A-3J. This core polypeptide includes amino acids 1-121 of the HCV polyprotein, with consensus amino acids Arg-9 and Thr-11 (positions 1780 and 1782, respectively, of FIG. 3A-3J). FIGS. 5A-5E (SEQ ID NOS:7 and 8) show the DNA and corresponding amino acid sequence of a representative fusion protein that includes a C-terminally truncated NS5 polypeptide with the C-terminus of the NS5 polypeptide fused to this core polypeptide. The C-terminally truncated NS5 polypeptide includes amino acids 1973-2990 of the HCV polyprotein, numbered relative to HCV-1 (see, Choo et al. (1991) *Proc. Natl. Acad. Sci. USA* 88:2451-2455), (amino acids 1-1018 of SEQ ID NO:8), fused to a core polypeptide as described above that includes amino acids 1-121 of the HCV polyprotein (amino acids 1019-1139 of SEQ ID NO:8).

If a core polypeptide is present, it can occur at the N-terminus, the C-terminus and/or internal to the fusion. Particularly preferred is a core polypeptide on the C-terminus as this allows for the formation of complexes with certain adjuvants, such as ISCOMs, described further below.

Other useful polypeptides in the HCV fusion include T-cell epitopes derived from any of the various regions in the polyprotein. In this regard, E1, E2, p7 and NS2 are known to contain human T-cell epitopes (both CD4+ and CD8+) and including one or more of these epitopes serves to increase vaccine efficacy as well as to increase protective levels against multiple HCV genotypes. Moreover, multiple copies of specific, conserved T-cell epitopes can also be used in the fusions, such as a composite of epitopes from different genotypes.

For example, polypeptides from the HCV E1 and/or E2 regions can be used in the fusions of the present invention. E2 exists as multiple species (Spaete et al., *Virol.* (1992) 188: 819-830; Selby et al., *J. Virol.* (1996) 70:5177-5182; Grakoui et al., *J. Virol.* (1993) 67:1385-1395; Tomei et al., *J. Virol.* (1993) 67:4017-4026) and clipping and proteolysis may occur at the N- and C-termini of the E2 polypeptide. Thus, an E2 polypeptide for use herein may comprise amino acids 405-661, e.g., 400, 401, 402 . . . to 661, as well as polypeptides such as 383 or 384-661, 383 or 384-715, 383 or 384-746, 383 or 384-749 or 383 or 384-809, or 383 or 384 to any C-terminus between 661-809, of an HCV polyprotein, numbered relative to the full-length HCV-1 polyprotein. Preferably, a portion of the E2 polypeptide that includes amino acids 384-715 is included in the HCV fusions polypeptide. Preferably, the E2 polypeptide sequence occurs at the N-terminal of the HCV fusion polypeptide.

Similarly, E1 polypeptides for use herein can comprise amino acids 192-326, 192-330, 192-333, 192-360, 192-363, 192-383, or 192 to any C-terminus between 326-383, of an HCV polyprotein.

Immunogenic fragments of E1 and/or E2 which comprise epitopes may be used in the subject fusions. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers.

For example, epitopes derived from, e.g., the hypervariable region of E2, such as a region spanning amino acids 384-410 or 390-410, can be included in the fusions. A particularly effective E2 epitope to incorporate into an E2 polypeptide sequence is one which includes a consensus sequence derived from this region, such as the consensus sequence (SEQ ID NO: 9) Gly-Ser-Ala-Ala-Arg-Thr-Thr-Ser-Gly-Phe-Val-Ser-Leu-Phe-Ala-Pro-Gly-Ala-Lys-Gln-Asn, which represents a consensus sequence for amino acids 390-410 of the HCV type 1 genome. Additional epitopes of E1 and E2 are known and described in, e.g., Chien et al., International Publication No. WO 93/00365.

Moreover, the E1 and/or E2 polypeptides may lack all or a portion of the membrane spanning domain. With E1, generally polypeptides terminating with about amino acid position 370 and higher (based on the numbering of the HCV-1 polyprotein) will be retained by the ER and hence not secreted into growth media. With E2, polypeptides terminating with about amino acid position 731 and higher (also based on the numbering of the HCV-1 polyprotein) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and/or E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acids 730 and lower. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond about amino acid position 715. Particularly preferred E2 truncations are those molecules truncated after any of amino acids 715-730, such as 725.

In certain preferred embodiments, the fusion protein comprises a modified NS3, an NS4 (NS4a and NS4b), a C-terminally truncated NS5 and, optionally, a core polypeptide of an HCV (NS3*NS4NS5t or NS3*NS4NS5tCore fusion proteins, also termed "NS3*45t" and "NS3*45tCore" herein). These fusion polypeptides may also include a portion of the HCV NS2 polypeptide, preferably, the NS2 portion from amino acids 1018 to 1026 (numbered as in the HCV-1 polyprotein). These regions need not be in the order in which they naturally occur in the native HCV polyprotein. Thus, for example, the core polypeptide may be at the N- and/or C-terminus of the fusion. In a particularly preferred embodiment, the NS5t includes amino acids 1973-2990, numbered relative to the full-length HCV-1 polyprotein and the NS3* molecule includes a substitution of Ala for Ser normally found at position 1165, and the regions occur in the following N-terminus to C-terminus order: NS3*NS4NS5t or NS2NS3*NS4NS5t. These fusions can include a core polypeptide at the C-terminus of the molecule. If present, the core polypeptide preferably includes the sequence of amino acids depicted at amino acid positions 1772-1892 of FIG. 3A-3J. This core polypeptide includes amino acids 1-121 of the HCV polyprotein, with consensus amino acids Arg-9 and Thr-11 (positions 1780 and 1782, respectively, of FIG. 3A-3J).

In another preferred embodiment, the HCV fusion polypeptides described immediately above include an E2 polypeptide at the N-terminus preceding NS3* or NS2. Preferably, the E2 polypeptide is a C-terminally truncated polypeptide and includes amino acids 384-715, numbered relative to the full-length HCV-1 polyprotein. This fusion can also optionally include a core polypeptide as described above.

If desired, the fusion proteins, or the individual components of these proteins, also can contain other amino acid sequences, such as amino acid linkers or signal sequences, as well as ligands useful in protein purification, such as glutathione-S-transferase and staphylococcal protein A.

Polynucleotides Encoding the HCV Fusion Polypeptides

Polynucleotides contain less than an entire HCV genome, or alternatively can include the sequence of the entire polyprotein with a C-terminally truncated NS5 domain, as described above. The polynucleotides can be RNA or single- or double-stranded DNA. Preferably, the polynucleotides are isolated free of other components, such as proteins and lipids. The polynucleotides encode the fusion proteins described above, and thus comprise coding sequences for NS5t and at least one other HCV polypeptide from a different region of the HCV polyprotein, such as polypeptides derived from NS2, p7, E1, E2, NS3, NS4, core, etc. The polynucleotides preferably encode HCV fusion polypeptides comprising or consisting of E2NS2NS3*NS4NS5core, E2NS2NS3*NS4NS5tcore, NS2NS3*NS4NS5core or NS2NS3*NS4NS5tcore. Polynucleotides of the invention can also comprise other nucleotide sequences, such as sequences coding for linkers, signal sequences, or ligands useful in protein purification such as glutathione-S-transferase and staphylococcal protein A.

To aid expression yields, it may be desirable to split the polyprotein into fragments for expression. These fragments can be used in combination in compositions as described herein. Alternatively, these fragments can be joined subsequent to expression. Thus, for example, NS3*NS4 can be expressed as one construct and NS5tCore can be expressed as a second construct and the two proteins subsequently fused or added separately to compositions. Similarly, E2NS3*NS4 can be expressed as one construct and NS5tCore expressed as a second construct. It is to be understood that the above combinations are merely representative and any combination of fusions can be expressed separately.

It has been previously shown that inclusion of a truncated NS5 (for example, NS5 truncated at amino acid 2990) in a HCV fusion polypeptide often results in a higher level of expression of the fusion polypeptide compared to one with a full-length NS5 included. It has also been previously suggested that addition of HCV core sequences (for example core amino acids 1-121), at the carboxy terminal of an HCV fusion polypeptide results in a higher level of expression than the expression level of HCV fusion polypeptides without core sequences at the carboxy-terminal. The present inventors have now found that addition of certain HCV E2 sequences (for example, amino acids 384-715) at the N-terminal of an HCV fusion polypeptide enhances the recombinant expression level of the fusion polypeptide compared to those not containing E2 sequences at the N-terminal. The invention thus also provides a method of enhancing the recombinant expression of an HCV fusion polypeptide by positioning HCV E2 sequences, preferably amino acids 384-715 (numbered with respect to the HCV-1 polyprotein), at the N-terminal of the fusion polypeptide. It will be apparent that such positioning of the E2 amino acid sequences at the N-terminal can be accomplished by fusing E2 coding sequences to the 5' end of the fusion polypeptide.

Polynucleotides encoding the various HCV polypeptides can be isolated from a genomic library derived from nucleic acid sequences present in, for example, the plasma, serum, or liver homogenate of an HCV infected individual or can be synthesized in the laboratory, for example, using an automatic synthesizer. An amplification method such as PCR can be used to amplify polynucleotides from either HCV genomic DNA or cDNA encoding therefor.

Polynucleotides can comprise coding sequences for these polypeptides which occur naturally or can be artificial sequences which do not occur in nature. These polynucleotides can be ligated to form a coding sequence for the fusion proteins using standard molecular biology techniques. A polynucleotide encoding these proteins can be introduced into an expression vector which can be expressed in a suitable expression system. A variety of bacterial, yeast, mammalian and insect expression systems are available in the art and any such expression system can be used. Optionally, a polynucleotide encoding these proteins can be translated in a cell-free translation system. Such methods are well known in the art. The proteins also can be constructed by solid phase protein synthesis.

The expression constructs of the present invention, including the desired fusion, or individual expression constructs comprising the individual components of these fusions, may be used for nucleic acid immunization, to stimulate a cellular immune response, using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use with the polynucleotides of the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. (See, also, Feigner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443: 629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255: 10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219, 740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508-519; and International Publication Nos. WO 95/07995 and WO 96/17072.

Other vectors can be used, including but not limited to adeno-associated virus vectors, simian virus 40 and cytomegalovirus. Bacterial vectors, such as *Salmonella* ssp. *Yersinia enterocolitica*, *Shigella* spp., *Vibrio cholerae*, *Mycobacterium* strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Feigner, P. L., *Advanced Drug Delivery Reviews* (1990) 5:163-187, for a review of delivery systems useful for gene transfer. One particularly effective method of delivering DNA using electroporation is described in International Publication No. WO/0045823.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Compositions Comprising Fusion Proteins or Polynucleotides

The invention also provides immunogenic compositions comprising the fusion proteins or polynucleotides. The compositions may be used to stimulate an immunological response, as defined above. The compositions may include one or more fusions, so long as one of the fusions includes a C-terminally truncated NS5 domain as described herein. Preferably, the composition will include a HCV fusion polypeptide comprising or consisting of a portion of NS2, NS3 (particularly a modified NS3), NS4, NS5t and core. More preferably, the composition will include a HCV fusion polypeptide comprising or consisting of a portion of E2, NS2, NS3 (particularly a modified NS3), NS4, NS5t and core. Compositions of the invention may also comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. The proteins or polynucleotides of the invention can also be adsorbed to, entrapped within or otherwise associated with liposomes and particulate carriers such as PLG. Liposomes and other particulate carriers are described above.

If desired, co-stimulatory molecules which improve immunogen presentation to lymphocytes, such as B7-1 or B7-2, or cytokines, lymphokines, and chemokines, including but not limited to cytokines such as IL-2, modified IL-2 (cys125 to ser125), GM-CSF, IL-12, γ-interferon, IP-10, MIP1β, FLP-3, ribavirin and RANTES, may be included in the composition. Optionally, adjuvants can also be included in a composition. Adjuvants which can be used include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% TWEEN 80, and 0.5% SPAN 85 (optionally containing various amounts of MTP-PE), formulated into submicron particles using a microfluidizer such as Model 110Y microfluidizer (Microfluidics, Newton, Mass.), (b) SAF, containing 10% Squalane, 0.4% TWEEN 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as QS21 or Stimulon™ (Cambridge Bioscience, Worcester, Mass.) may be used or particles generated therefrom such as ISCOMs (immunostimulating complexes), which ISCOMs may be devoid of additional detergent (see, e.g., International Publication No. WO 00/07621); (4) Complete Freunds Adjuvant (CFA) and Incomplete Freunds Adjuvant (IFA); (5) cytokines, such as interleukins, such as IL-1, IL-2, IL-4, IL-5, IL-6, IL-7, IL-12 etc. (see, e.g., International Publication No. WO 99/44636), interferons, such as gamma interferon, macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (7) monophosphoryl lipid A (MPL) or 3-O-deacylated MPL (3dMPL) (see, e.g., GB 2220221; EPA 0689454), optionally in the substantial absence of alum (see, e.g., International Publication No. WO 00/56358); (8) combinations of 3dMPL with, for example, QS21 and/or oil-in-water emulsions (see, e.g., EPA 0835318; EPA 0735898; EPA 0761231); (9) a polyoxyethylene ether or a polyoxyethylene ester (see, e.g., International Publication No. WO 99/52549); (10) an immunostimulatory oligonucleotide such as a CpG oligonucleotide, or a saponin and an immunostimulatory oligonucleotide, such as a CpG oligonucleotide (see, e.g., International Publication No. WO 00/62800); (11) an immunostimulant and a particle of a metal salt (see, e.g., International Publication No. WO 00/23105); (12) a saponin and an oil-in-water emulsion (see, e.g., International Publication No. WO 99/11241; (13) a saponin (e.g., QS21)+3dMPL+IL-12 (optionally+a sterol) (see, e.g., International Publication No. WO 98/57659); (14) the MPL derivative RC529; and (15) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), -acetyl-normuramyl-L-alanyl-D-isoglutamine (CGP 11637, referred to nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), etc.

Moreover, the fusion protein can be adsorbed to, or entrapped within, an ISCOM. Classic ISCOMs are formed by combination of cholesterol, saponin, phospholipid, and immunogens. Generally, immunogens (usually with a hydrophobic region) are solubilized in detergent and added to the reaction mixture, whereby ISCOMs are formed with the immunogen incorporated therein. ISCOM matrix compositions are formed identically, but without viral proteins. Proteins with high positive charge may be electrostatically bound in the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998).

ISCOMs for use with the present invention are produced using standard techniques, well known in the art, and are described in e.g., U.S. Pat. Nos. 4,981,684, 5,178,860, 5,679,354 and 6,027,732; European Publ. Nos. EPA 109,942; 180,564 and 231,039; Coulter et al. (1998) *Vaccine* 16:1243. Typically, the term "ISCOM" refers to immunogenic complexes formed between glycosides, such as triterpenoid saponins (particularly Quil A), and antigens which contain a hydrophobic region. See, e.g., European Publ. Nos. EPA 109,942 and 180,564. In this embodiment, the HCV fusions (usually with a hydrophobic region) are solubilized in detergent and added to the reaction mixture, whereby ISCOMs are formed with the fusions incorporated therein. The HCV polypeptide ISCOMs are readily made with HCV polypeptides which show amphipathic properties. However, proteins and peptides which lack the desirable hydrophobic properties may be incorporated into the immunogenic complexes after coupling with peptides having hydrophobic amino acids, fatty acid radicals, alkyl radicals and the like.

As explained in European Publ. No. EPA 231,039, the presence of antigen is not necessary in order to form the basic ISCOM structure (referred to as a matrix or ISCOMATRIX), which may be formed from a sterol, such as cholesterol, a phospholipid, such as phosphatidylethanolamine, and a glycoside, such as Quil A. Thus, the HCV fusion of interest, rather than being incorporated into the matrix, is present on the outside of the matrix, for example adsorbed to the matrix via electrostatic interactions. For example, HCV fusions with high positive charge may be electrostatically bound to the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998).

The ISCOM matrix may be prepared, for example, by mixing together solubilized sterol, glycoside and (optionally) phospholipid. If phospholipids are not used, two dimensional structures are formed. See, e.g., European Publ. No. EPA 231,039. The term "ISCOM matrix" is used to refer to both the 3-dimensional and 2-dimensional structures. The glycosides to be used are generally glycosides which display amphipathic properties and comprise hydrophobic and hydrophilic regions in the molecule. Preferably saponins are used, such as the saponin extract from *Quillaja saponaria* Molina and Quil A. Other preferred saponins are aescine from *Aesculus hippocastanum* (Patt et al. (1960) *Arzneimittelforschung* 10:273-275 and sapoalbin from *Gypsophilla struthium* (Vochten et al. (1968) *J. Pharm. Belg.* 42:213-226.

In order to prepare the ISCOMs, glycosides are used in at least a critical micelle-forming concentration. In the case of Quil A, this concentration is about 0.03% by weight. The sterols used to produce ISCOMs may be known sterols of animal or vegetable origin, such as cholesterol, lanosterol, lumisterol, stigmasterol and sitosterol. Suitable phospholipids include phosphatidylcholine and phosphatidylethanolamine. Generally, the molar ratio of glycoside (especially when it is Quil A) to sterol (especially when it is cholesterol) to phospholipid is 1:1:0-1,±20% (preferably not more than ±10%) for each figure. This is equivalent to a weight ratio of about 5:1 for the Quil A:cholesterol.

A solubilizing agent may also be present and may be, for example a detergent, urea or guanidine. Generally, a nonionic, ionic or zwitter-ionic detergent or a cholic acid based detergent, such as sodium desoxycholate, cholate and CTAB (cetyltriammonium bromide), can be used for this purpose. Examples of suitable detergents include, but are not limited to, octylglucoside, nonyl N-methyl glucamide or decanoyl N-methyl glucamide, alkylphenyl polyoxyethylene ethers such as a polyethylene glycol p-isooctyl-phenylether having 9 to 10 oxyethylene groups (commercialized under the trade name TRITON X-100R™), acylpolyoxyethylene esters such as acylpolyoxyethylene sorbitane esters (commercialized under the trade name TWEEN 20™, TWEEN 80™, and the like). The solubilizing agent is generally removed for formation of the ISCOMs, such as by ultrafiltration, dialysis, ultracentrifugation or chromatography, however, in certain methods, this step is unnecessary. (See, e.g., U.S. Pat. No. 4,981,684).

Generally, the ratio of glycoside, such as QuilA, to HCV fusion by weight is in the range of 5:1 to 0.5:1. Preferably the ratio by weight is approximately 3:1 to 1:1, and more preferably the ratio is 2:1.

Once the ISCOMs are formed, they may be formulated into compositions and administered to animals, as described herein. If desired, the solutions of the immunogenic complexes obtained may be lyophilized and then reconstituted before use.

The HCV fusion polypeptides and compositions including the fusion polypeptides or the polynucleotides encoding the HCV fusion polypeptides, described above, can be used in combination with other HCV immunogenic proteins, and/or compositions comprising the same. For example, the HCV fusion polypeptides can be used in combination with any of the various HCV immunogenic proteins derived from one or more of the regions of the HCV polyprotein described in Table 1. One particular HCV antigen for use with the subject fusion polypeptide and/or composition comprising the fusion polypeptide, is an HCV E1E2 antigen. HCV E1E2 antigens are known, including complexes of HCV E1 with HCV E2, optionally containing part or all of the p7 region, such as HCV E1E2 complexes as described in PCT Publication No. WO 03/002065. The additional HCV immunogenic proteins can be provided in compositions with excipients, adjuvants, immunstimulatory molecules and the like, as described above. For example, the E1E2 complexes can be provided in compositions that include a submicron oil-in-water emulsion such as MF59 and/or oligonucleotides containing immunostimulatory nucleic acid sequences (ISS), such as CpY, CpR and unmethylated CpG motifs (a cytosine followed by guanosine and linked by a phosphate bond). Such compositions are described in detail in PCT Publication No. WO 03/002065.

Thus, it is readily apparent that the compositions of the present invention may be administered in conjunction with a number of immunoregulatory agents and will usually include an adjuvant. Such agents and adjuvants for use with the compositions include, but are not limited to, any of those substances described above, as well as one or more of the following set forth below.

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* (1995) eds. Powell & Newman. ISBN: 030644867X. Plenum), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (PCT Publication No. WO00/23105).

Aluminum salts may be included in compositions of the invention such that the dose of $Al^{3+}$ is between 0.2 and 1.0 mg per dose. In one embodiment, the aluminum-based adjuvant for use in the present compositions is alum (aluminum potassium sulfate ($AlK(SO_4)_2$)), or an alum derivative, such as that formed in situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment, the adjuvant for use with the present compositions comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particularly, aluminum salts may be present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil Emulsions

Oil emulsion compositions suitable for use as adjuvants in the compositions include squalene-water emulsions. Particularly preferred adjuvants are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the subject compositions.

C. Saponin Formulations

Saponin formulations, may also be used as adjuvants in the compositions. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see, PCT Publication No. WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin-based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPS)

Virosomes and Virus Like Particles (VLPs) can also be used as adjuvants with the present compositions. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Adjuvants suitable for use in the present compositions include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See, Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See, Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-Ribosylating Toxins and Detoxified Derivatives Thereof.

Bacterial ADP-ribosylating toxins and detoxified derivatives thereof may be used as adjuvants in the compositions. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., "The LTR72 Mutant of Heat-Labile Enterotoxin of *Escherichia coli* Enahnces the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6):1165-1167.

F. Bioadhesives and Mucoadhesives

Bioadhesives and mucoadhesives may also be used as adjuvants in the subject compositions. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the compositions. See, e.g., WO99/27960.

G. Microparticles

Microparticles may also be used as adjuvants in the compositions. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly($\alpha$-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the compositions include polyoxyethylene ethers and polyoxyethylene esters. See, e.g., WO99/52549. Such formulations further include polyoxyethylene sorbitan ester surfactants in combination with an octoxynol (WO01/21657) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use as adjuvants in the compositions include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2):214-218; and U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612.

M. Thiosemicarbazone Compounds

Examples of thiosemicarbazone compounds, as well as methods of formulating, manufacturing, and screening for compounds all suitable for use as adjuvants in the compositions include those described in WO04/60308. The thiosemicarbazones are particularly effective in the stimulation of human peripheral blood mononuclear cells for the production of cytokines, such as TNF-$\alpha$.

N. Tryptanthrin Compounds

Examples of tryptanthrin compounds, as well as methods of formulating, manufacturing, and screening for compounds all suitable for use as adjuvants in the compositions include those described in WO04/64759. The tryptanthrin compounds are particularly effective in the stimulation of human peripheral blood mononuclear cells for the production of cytokines, such as TNF-$\alpha$.

O. Human Immunomodulators Human immunomodulators suitable for use as adjuvants in the compositions include cytokines, such as interleukins (e.g. IL-1, IL-2, IL-4, IL-5, IL-6, IL-7, IL-12, etc.), interferons (e.g. interferon-$\gamma$), macrophage colony stimulating factor, and tumor necrosis factor.

The compositions may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally +a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

Aluminum salts and MF59 are preferred adjuvants for use with injectable vaccines. Bacterial toxins and bioadhesives are preferred adjuvants for use with mucosally-delivered vaccines, such as nasal vaccines.

Methods of Producing HCV-Specific Antibodies

The HCV fusion polypeptides can be used to produce HCV-specific polyclonal and monoclonal antibodies. HCV-specific polyclonal and monoclonal antibodies specifically bind to HCV antigens. Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against HCV-specific epitopes present in the fusion polypeptides can also be readily produced. Normal B cells from a mammal, such as a mouse, immunized with an HCV fusion polypeptide, can be fused with, for example, HAT-sensitive mouse myeloma cells to produce hybridomas. Hybridomas producing HCV-specific antibodies can be identified using RIA or ELISA and isolated by cloning in semi-solid agar or by limiting dilution. Clones producing HCV-specific antibodies are isolated by another round of screening.

Antibodies, either monoclonal and polyclonal, which are directed against HCV epitopes, are particularly useful for detecting the presence of HCV or HCV antigens in a sample, such as a serum sample from an HCV-infected human. An immunoassay for an HCV antigen may utilize one antibody or several antibodies. An immunoassay for an HCV antigen may use, for example, a monoclonal antibody directed towards an HCV epitope, a combination of monoclonal antibodies directed towards epitopes of one HCV polypeptide, monoclonal antibodies directed towards epitopes of different HCV polypeptides, polyclonal antibodies directed towards the same HCV antigen, polyclonal antibodies directed towards different HCV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate HCV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HCV particles or antigens from a biological sample, such as blood or plasma. The bound HCV particles or antigens are recovered from the column matrix by, for example, a change in pH.

HCV-Specific T cells

HCV-specific T cells that are activated by the above-described fusions, including the NS2NS3*NS4NS5t fusion protein or E2NS2NS3*NS4NS5t fusion protein, with or without a core polypeptide, as well as any of the other various fusions described herein, expressed in vivo or in vitro, preferably recognize an epitope of an HCV polypeptide such as an NS2, p7, E1, E2, NS3, NS4, NS5a or NS5b polypeptide, including an epitope of a fusion of one or more of these peptides with an NS5t, with or without a core polypeptide. HCV-specific T cells can be $CD8^+$ or $CD4^+$. In other embodiments, the NS5 portion may not be truncated.

The invention provides novel HCV fusion polypeptides that include the naturally occurring methionine of the NS2 protein found at amino acid position 1018 fused to at least the NS345 protein sequences, wherein the NS3 sequence is mutated to remove the inherent protease function of NS3. These compositions can further comprise E2 and core.

Adding E2 and/or core to the fusion proteins provides additional T-cell epitopes for the immune system to recognize. By not including E1, P7 and the major portion of NS2, expression is optimized due to loss of hydrophobic regions.

Expressing HCV proteins without the terminus of NS5b also enhances protein expression. (See, US20060088819-A1)

HCV-specific $CD8^+$ T cells can be cytotoxic T lymphocytes (CTL) which can kill HCV-infected cells that display any of these epitopes complexed with an MHC class I molecule. HCV-specific $CD8^+$ T cells can be detected by, for example, $^{51}Cr$ release assays (see the examples). $^{51}Cr$ release assays measure the ability of HCV-specific $CD8^+$ T cells to lyse target cells displaying one or more of these epitopes. HCV-specific $CD8^+$ T cells which express antiviral agents, such as IFN-γ, are also contemplated herein and can also be detected by immunological methods, preferably by intracellular staining for IFN-γ or like cytokine after in vitro stimulation with one or more of the HCV polypeptides, such as but not limited to an E2, NS3, NS4, NS5a, or NS5b polypeptide or core (see the examples).

HCV-specific $CD4^+$ cells activated by the above-described fusions, such as but not limited to an NS2NS3*NS4NS5t fusion polypeptide or an E2NS2NS3*NS4NS5t fusion polypeptide, with or without a core polypeptide, expressed in vivo or in vitro, preferably recognize an epitope of an HCV polypeptide, such as but not limited to an NS2, E2, NS3, NS4, NS5a, or NS5b or core polypeptide, including an epitope of fusions thereof, bound to an MHC class II molecule on an HCV-infected cell and proliferate in response to stimulating, e.g., NS2NS3*NS4NS5t or E2NS2NS3*NS4NS5t fusion polypeptide, with or without a core polypeptide.

HCV-specific $CD4^+$ T cells can be detected by a lymphoproliferation assay (see the examples). Lymphoproliferation assays measure the ability of HCV-specific $CD4^+$ T cells to proliferate in response to, e.g., an NS2, E2, NS3, an NS4, an NS5a, and/or an NS5b or core epitope.

Methods of Activating HCV-Specific T Cells.

The HCV fusion polypeptides or polynucleotides can be used to activate HCV-specific T cells either in vitro or in vivo. Activation of HCV-specific T cells can be used, inter alia, to provide model systems to optimize CTL responses to HCV and to provide prophylactic or therapeutic treatment against HCV infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with an HCV. Preferred mammals include mice, chimpanzees, baboons, and humans. The HCV serves to expand the number of activated HCV-specific T cells in the mammal. The HCV-specific T cells derived from the mammal can then be restimulated in vitro by adding an HCV fusion polypeptide as described herein, such as but not limited to an HCV NS2NS3*NS4NS5t fusion protein or an E2NS2NS3*NS4NS5t fusion protein, with or without a core polypeptide, to the T cells. The HCV-specific T cells can then be tested for, inter alia, proliferation, the production of IFN-γ, and the ability to lyse target cells displaying HCV epitopes in vitro.

In a lymphoproliferation assay, HCV-activated CD4+ T cells proliferate when cultured with an HCV polypeptide, such as but not limited to an NS3, NS4, NS5a, NS5b, NS3NS4NS5, E2NS3NS4NS5, or E2NS2NS3NS4NS5, or E2NS3NS4NS5t, or E2NS2NS3NS4NS5t, or E2NS3NS4NS5core, or E2NS2NS3NS4NS5core, or E2NS3NS4NS5tcore, or E2NS2NS3NS4NS5tcore epitopic peptide, but not in the absence of an epitopic peptide. Thus, particular HCV epitopes, such as NS2, E2, NS3, NS4, NS5a, NS5b, or core and fusions of these epitopes, such as but not limited to NS3NS4NS5 and E2NS3NS4NS5 epitopes that are recognized by HCV-specific CD4+ T cells can be identified using a lymphoproliferation assay.

Similarly, detection of IFN-γ in HCV-specific CD4+ and/or CD8+ T cells after in vitro stimulation with the above-described fusion proteins, can be used to identify, for example, fusion protein epitopes, such as but not limited to epitopes of NS2, p7, E1, E2, NS3, NS4, NS5a, NS5b, and fusions of these epitopes, such as but not limited to NS3NS4NS5, and E2NS3NS4NS5 epitopes that are particularly effective at stimulating CD4+ and/or CD8+ T cells to produce IFN-γ (see Example 2).

Further, $^{51}$Cr release assays are useful for determining the level of CTL response to HCV. See Cooper et al. Immunity 10:439-449. For example, HCV-specific CD8+ T cells can be derived from the liver of an HCV infected mammal. These T cells can be tested in $^{51}$Cr release assays against target cells displaying, e.g., E2NS2NS3NS4NS5 or NS2NS3NS4NS5 epitopes. Several target cell populations expressing different NS2NS3NS4NS5 or E2NS2NS3NS4NS5 epitopes can be constructed so that each target cell population displays different epitopes of NS2NS3NS4NS5 or E2NS2NS3NS4NS5. The HCV-specific CD8+ cells can be assayed against each of these target cell populations. The results of the $^{51}$Cr release assays can be used to determine which epitopes of NS2NS3NS4NS5 or E2NS2NS3NS4NS5 are responsible for the strongest CTL response to HCV. NS2NS3*NS4NS5t fusion proteins or E2NS2NS3*NS4NS5t fusion proteins, with or without core polypeptides, which contain the epitopes responsible for the strongest CTL response can then be constructed using the information derived from the $^{51}$Cr release assays.

An HCV fusion polypeptide as described above, or polynucleotide encoding such a fusion polypeptide, can be administered to a mammal, such as a mouse, baboon, chimpanzee, or human, to stimulate a humoral and/or cellular immune response, such as to activate HCV-specific T cells in vivo. Administration can be by any means known in the art, including parenteral, intranasal, intramuscular or subcutaneous injection, including injection using a biological ballistic gun ("gene gun"), as discussed above.

Preferably, injection of a polynucleotide encoding an HCV fusion polypeptide is used to activate T cells. In addition to the practical advantages of simplicity of construction and modification, injection of the polynucleotides results in the synthesis of a fusion protein in the host. Thus, these immunogens are presented to the host immune system with native post-translational modifications, structure, and conformation. The polynucleotides are preferably injected intramuscularly to a large mammal, such as a human, at a dose of 0.5, 0.75, 1.0, 1.5, 2.0, 2.5, 5 or 10 mg/kg.

A composition of the invention comprising an HCV fusion polypeptide or polynucleotide encoding same is administered in a manner compatible with the particular composition used and in an amount which is effective to activate HCV-specific T cells as measured by, inter alia, a $^{51}$Cr release assay, a lymphoproliferation assay, or by intracellular staining for IFN-γ. The proteins and/or polynucleotides can be administered either to a mammal which is not infected with an HCV or can be administered to an HCV-infected mammal. The particular dosages of the polynucleotides or fusion proteins in a composition will depend on many factors including, but not limited to the species, age, and general condition of the mammal to which the composition is administered, and the mode of administration of the composition. An effective amount of the composition of the invention can be readily determined using only routine experimentation. In vitro and in vivo models described above can be employed to identify appropriate doses. The amount of polynucleotide used in the example described below provides general guidance which can be used to optimize the activation of HCV-specific T cells either in vivo or in vitro. Generally, 0.5, 0.75, 1.0, 1.5, 2.0, 2.5, 5 or 10 mg of an HCV fusion polypeptide or polynucleotide will be administered to a large mammal, such as a baboon, chimpanzee, or human. If desired, co-stimulatory molecules or adjuvants can also be provided before, after, or together with the compositions.

Immune responses of the mammal generated by the delivery of a composition of the invention, including activation of HCV-specific T cells, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

III. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

EXAMPLE 1

Cloning of Polynucleotides Encoding HCV Fusion Polypeptides

Synthetic nucleic acid sequences encoding, in an amino-terminal to carboxy-terminal direction, the carboxy terminus of NS2 from amino acid 1018 to 1026, amino acids 1027 to 1657 of NS3, amino acids 1658 to 1972 of NS4, amino acids 1973 to 2990 or 3011 of NS5 and optionally amino acids 1 to 121 of core, wherein the serine at position 1165 of the NS3 sequence is replaced with an alanine, amino acid 9 of the core sequence if present is arginine and amino acid 11 of the core sequence is threonine, and optionally containing an E2 sequence from amino acid 384 to amino acid 715, were constructed following general methods and those outlined below. The various constructs are represented schematically in FIG. 11 with amino acid numberings relative to the HCV-1 sequence. The nucleic acid sequences were cloned into plasmid vectors, and fusion polypeptides were expressed from host cells transformed with the plasmid vectors containing the fusion-polypeptide-encoding DNA insert, by utilizing standard recombinant cloning techniques and in particular those methods described previously in US2006-0088819A1, WO01/38360 and WO2004/005473.

A detailed example is given below for construction of one embodiment. Similar approaches were used to construct plasmid vectors containing the other nucleic acid sequences described above.

Cloning of Polynucleotides Encoding e2 ns3$_m$ns5tr.c121

Figure 7:
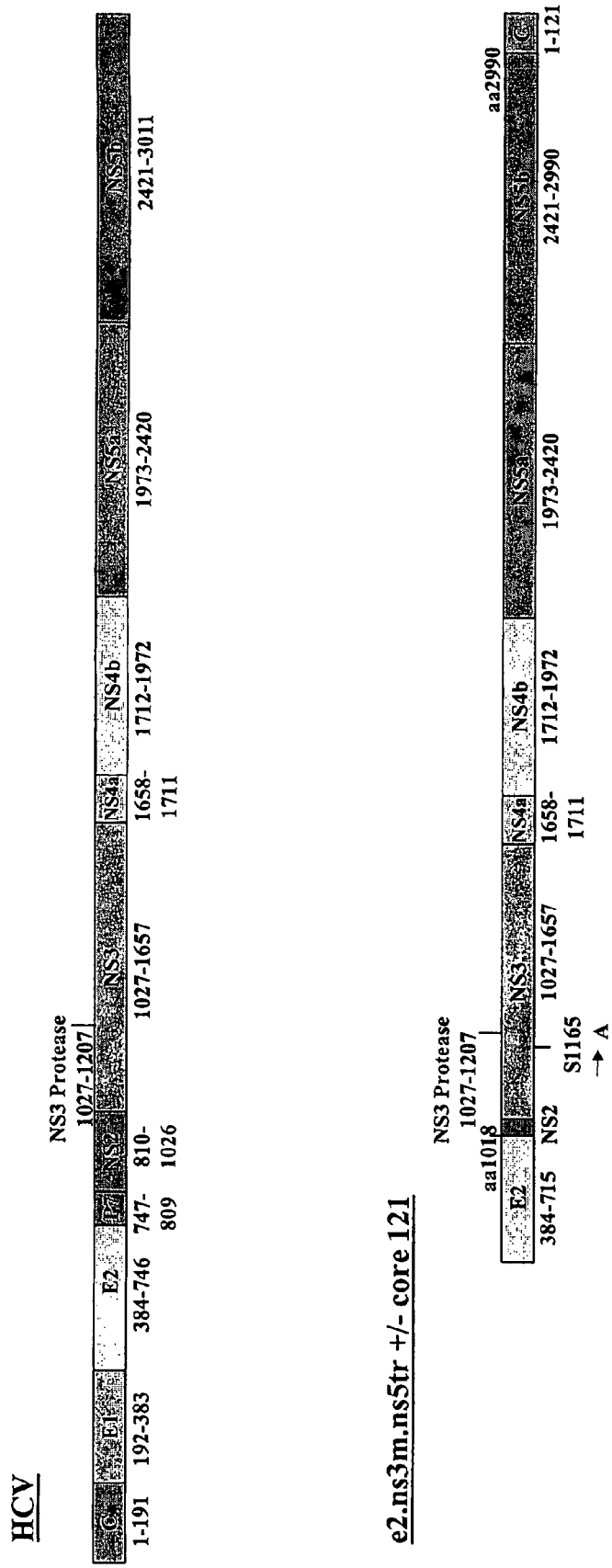
FIG. 7 depicts the genetic organization of an exemplary fusion polypeptide of the present invention.

A synthetic HCV1a nucleic acid was constructed to encode an HCV fusion polypeptide consisting of, in an amino-terminal to carboxy-terminal direction, a methionine, amino acids 384-715 of E2, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is arginine and amino acid 11 of the core sequence is threonine. The fusion protein encoded by this nucleic acid sequence is represented schematically in FIG. 7 with amino acid numberings relative to the HCV-1 sequence, and it is designated herein as "e2 ns3$_m$ns5tr.c121", "e2.ns3m-ns5tr.core121", or "E2NS3*NS4NS5tr.core121" or "E2NS2NS3*NS4NS5tr.core121".

Figure 6A:
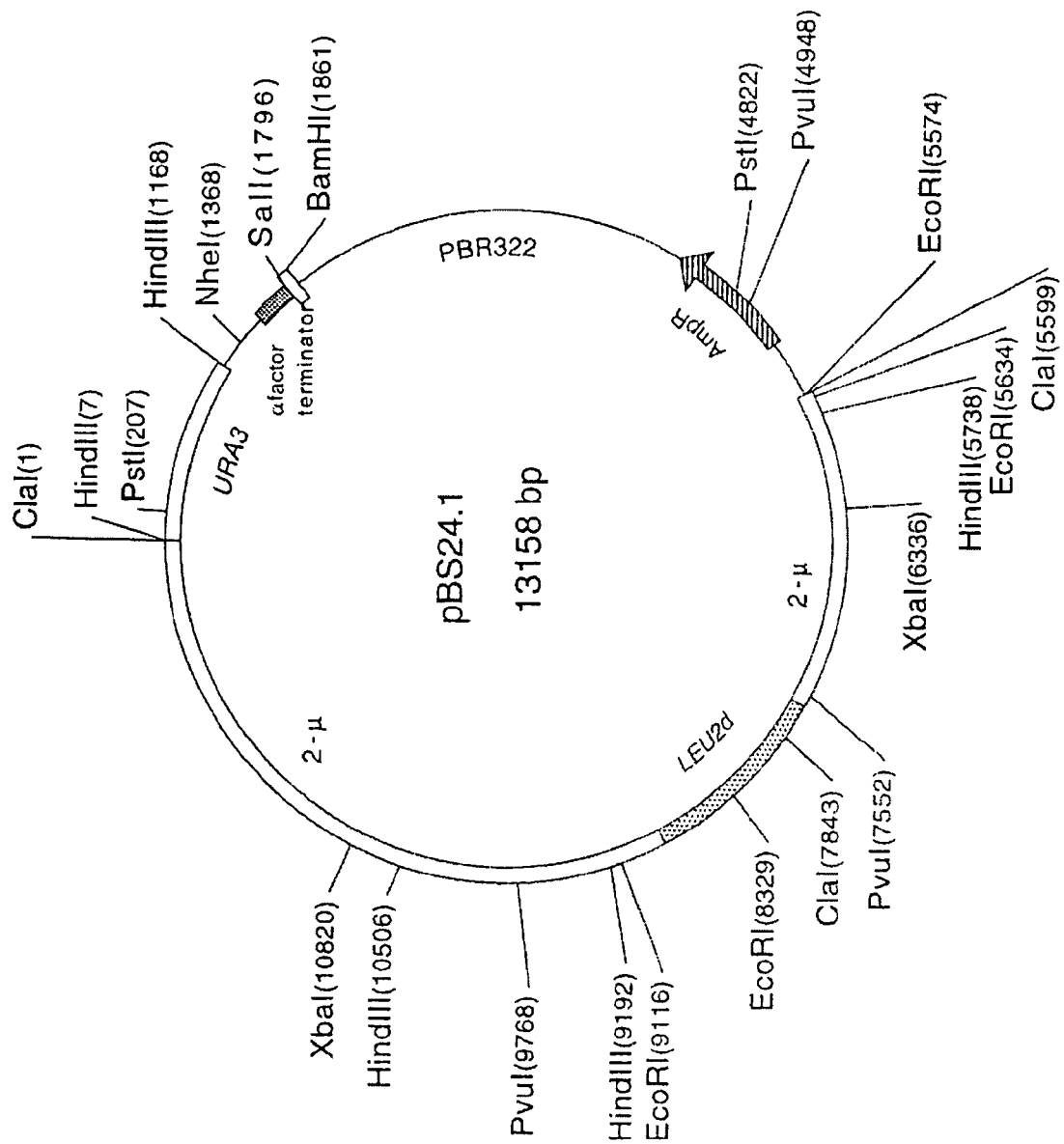
Figure 6C:
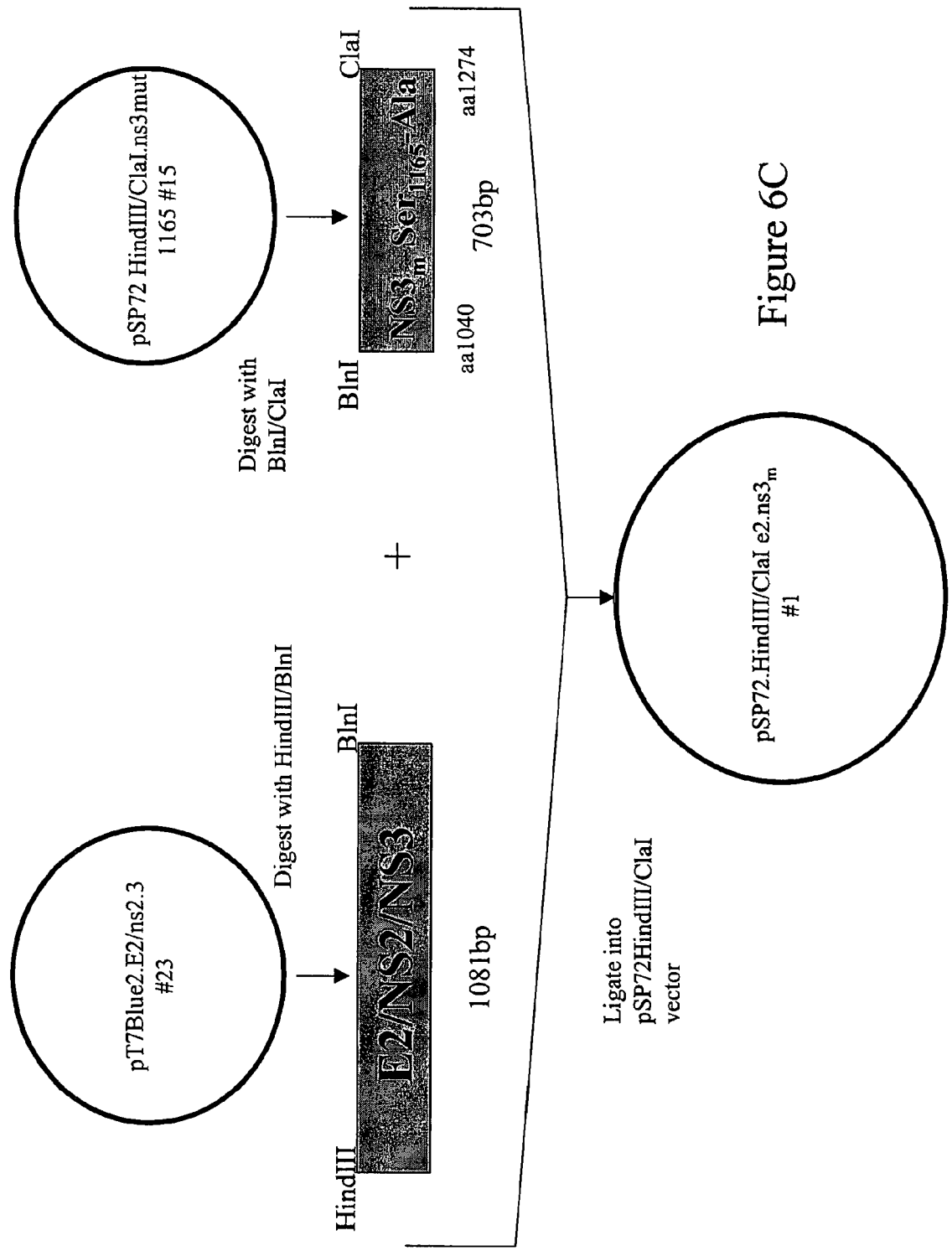
Figure 6D:
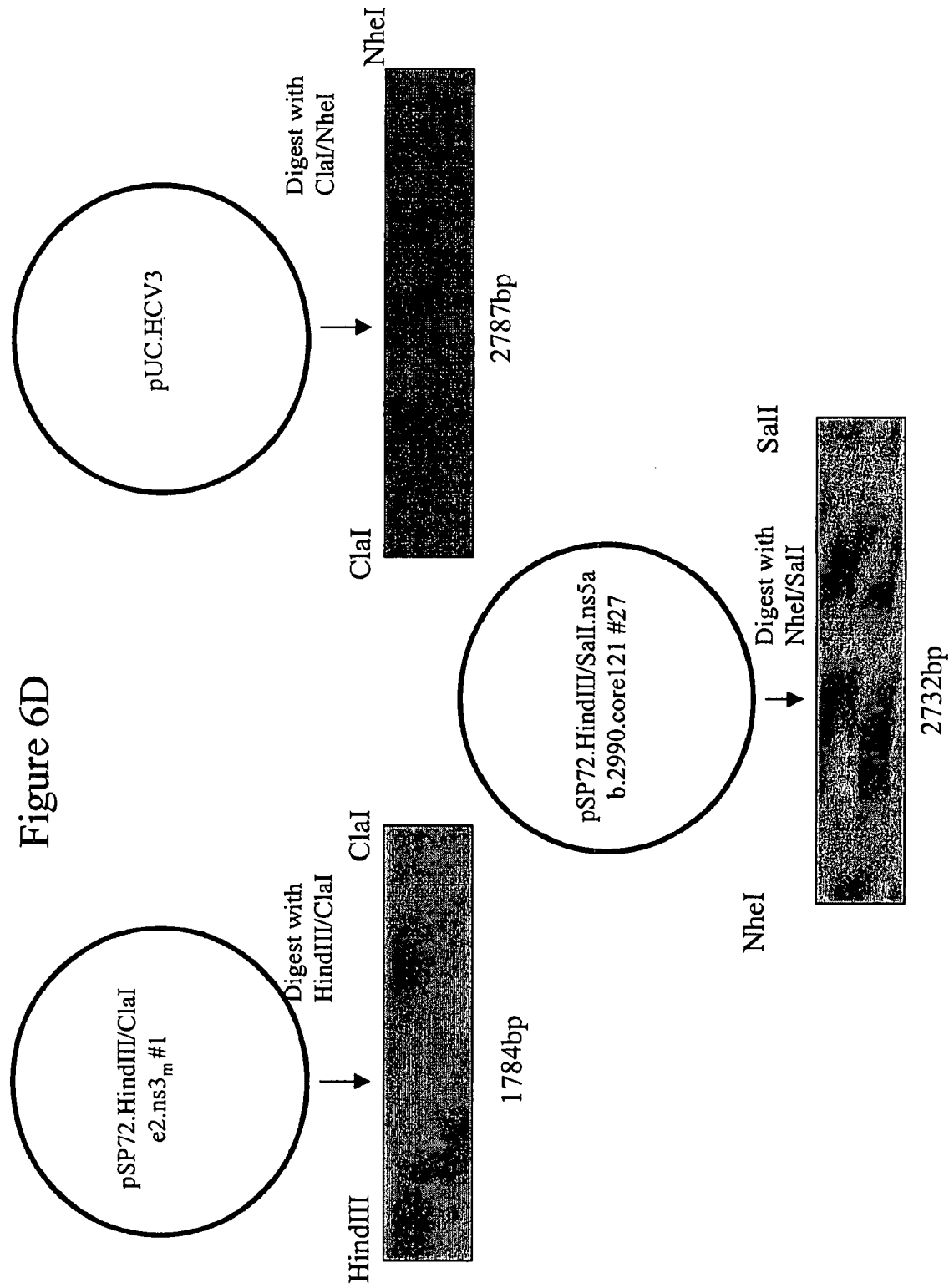
Figure 6E:
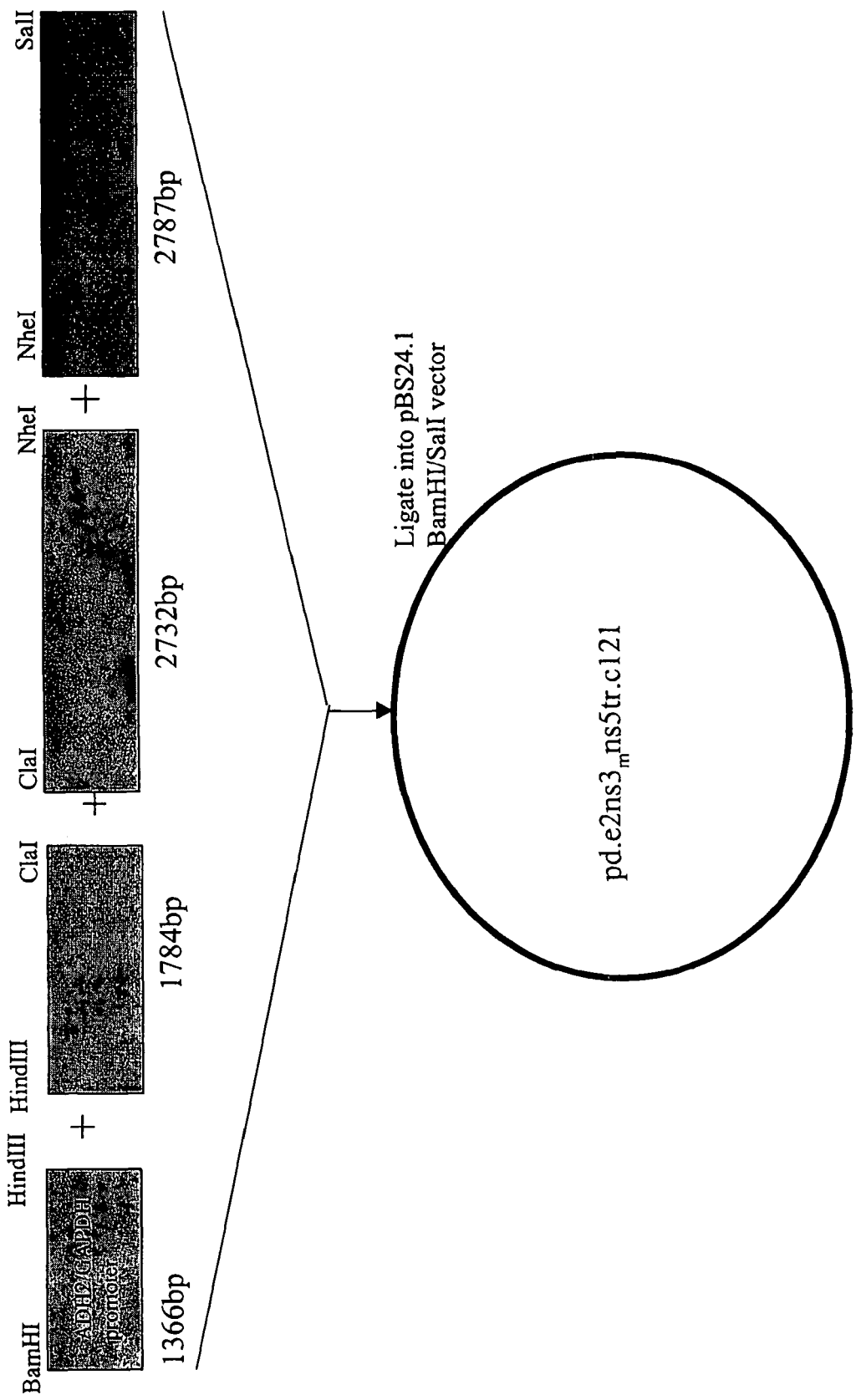
Figure 6F:
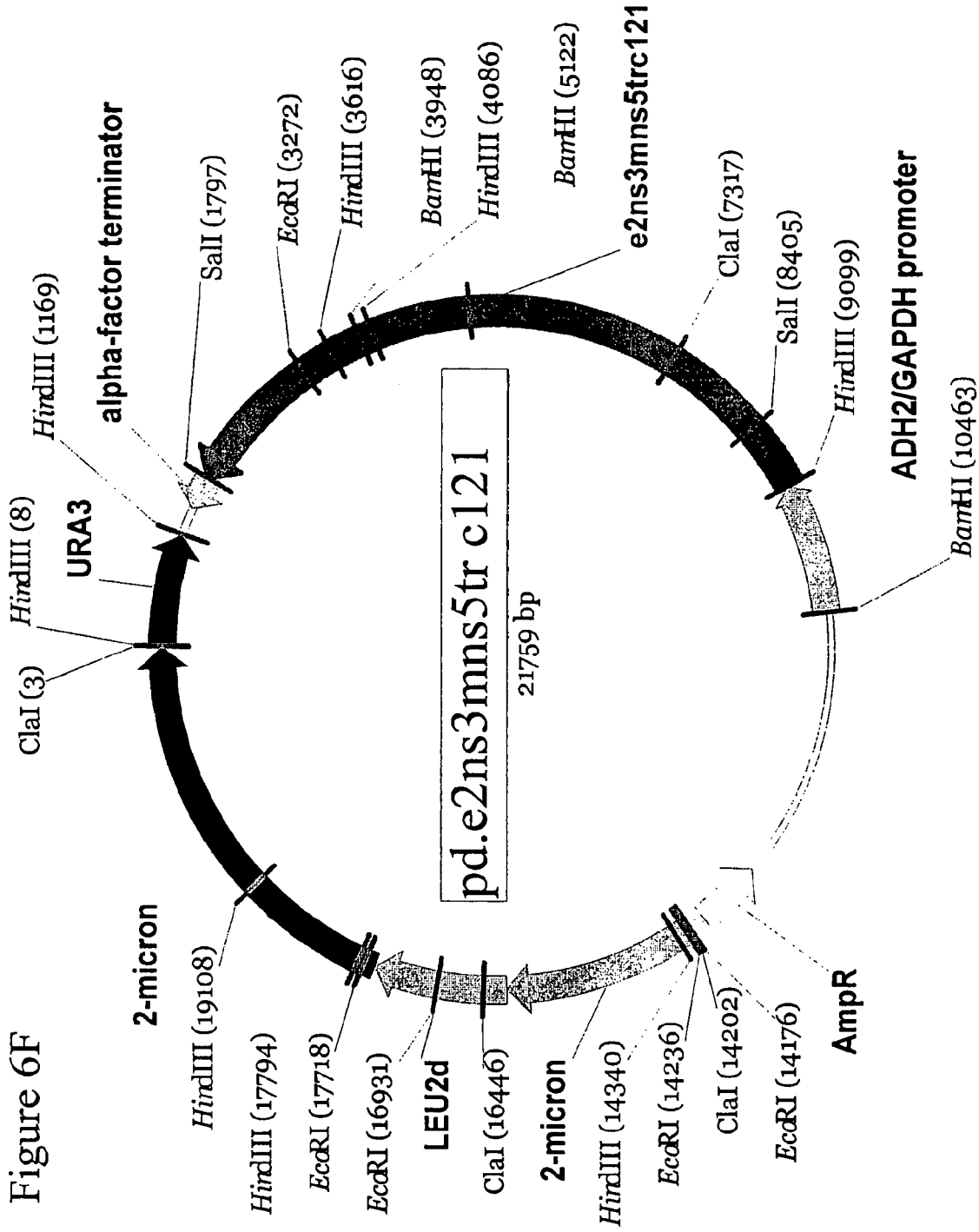

The e2 ns3$_m$ns5tr.c121 fusion polypeptide was genetically engineered for expression in *Saccharomyces cerevisiae* using the yeast expression vector pBS24.1 (U.S. Pat. No. 6,458,527 section 4.2.4.2 and U.S. Pat. No. 5,635,374, illustrated in FIG. 6a). This vector contains the 2µ sequence for autonomous replication in yeast and the yeast genes leu2d and URA3 as selectable markers. The α-factor terminator, β-lactamase gene and the ColE1 origin of replication, required for plasmid replication in bacteria, are also present in this expression vector.

The following steps were taken to construct the expression cassette for the e2 ns3$_m$ns5tr.c121 polyprotein (illustrated in FIGS. 6a-6f):

First, to assemble the N-terminus region, a HindIII/AclI fragment of 819 bp was gel isolated from pGEM7.d.E2 (HindIII/XhoI) subclone #3. The 5' HindIII cloning site is followed by the sequence ACAAAACAAA SEQ ID NO:10, the inititator ATG, and codons for the HCV-1 E2 ectodomain, beginning at aa384 and continuing to an AclI restriction site at aa650. The HindIII/AclI fragment and a 34 bp AclI/CelII kinased synthetic fragment, corresponding to aa651-aa662 of the E2 ectodomain, were ligated into a pT7Blue2 HindIII/CelII vector containing a 228 bp CelII/BlnI fragment which encodes aa662 to aa715 of the HCV-1 E2 ectodomain sequence, followed by codons for aa1018-aa1039 of HCV-1 NS2 and NS3. The ligation mixture was transformed into HB101 competent cells and plated onto Luria-ampicillin agar plates (100 µg/ml). After miniprep DNA analysis, identification of the desired clones and sequence confirmation, pT7Blue2.E2/ns2.3 #23 was digested with HindIII and BlnI to isolate a 1081 bp fragment which encodes E2/NS2/NS3.

Secondly, to introduce the Ser$_{1165}$-Ala mutation in the NS3 domain, a BlnI/ClaI fragment of 703 bp was gel isolated from pSP72 HindIII/ClaI.ns3mut 1165 #15. This 703 bp fragment encodes aa1040-aa1274 of the HCV-1 genome in which Ser$_{1165}$ was mutated to Ala by site-directed mutagenesis.

Third, to facilitate the cloning of the e2.ns3$_m$-ns5core121 expression cassette, the 1081 bp HindIII/BlnI fragment (encoding E2/NS2/NS3) and the 703 bp Bln/ClaI fragment (encoding NS3m Ser1165-Ala) were ligated into the pSP72 HindIII/ClaI vector. The ligation mixture was transformed as above, and after DNA analysis the resultant clone was named pSP72.HindIII/Cla e2.ns3$_m$ #1

Fourth, a 1784 bp HindIII/ClaI fragment, encoding E2/NS2/NS3m, was gel purified from pSP72.HindIII/Cla e2.ns3$_m$ #1 described above. A ClaI/NheI 2787 bp fragment encoding aa1274-aa2202 from NS3-NS5a of HCV-1 was isolated from a full-length HCV-1 clone, pUC.HCV3. A 2732 bp Nhe/SalI fragment was gel isolated from a pSP72.HindIII/SalI.ns5ab.2990.core121 #27 subclone. The Nhe/Sal fragment corresponds to aa2203-2990 of NS5a and NS5b, followed by aa1-121 of the core domain. Within the HCV-1 core sequence, consensus aa were incorporated at position 9 (Arg instead of the Lys of HCV-1 core sequence) and position 11 (Thr instead of the Asn of HCV-1).

Lastly, a 1366 bp BamHI/HindIII ADH2/GAPDH (Alcohol dehydrogenase 2/Glyseraldehyde-3-phosphate dehydrogenase) promoter fragment, described in the U.S. Pat. No. 6,183,985, was ligated with the 1784 bp HindIII/ClaI fragment, the 2787 bp Cla/NheI fragment, and the 2732 bp NheI/SalI fragment into the pBS24.1 BamHI/SalI yeast expression vector, thereby creating plasmid pd.e2 ns3$_m$ns5tr.c121 (see FIG. 6f).

Figure 11:
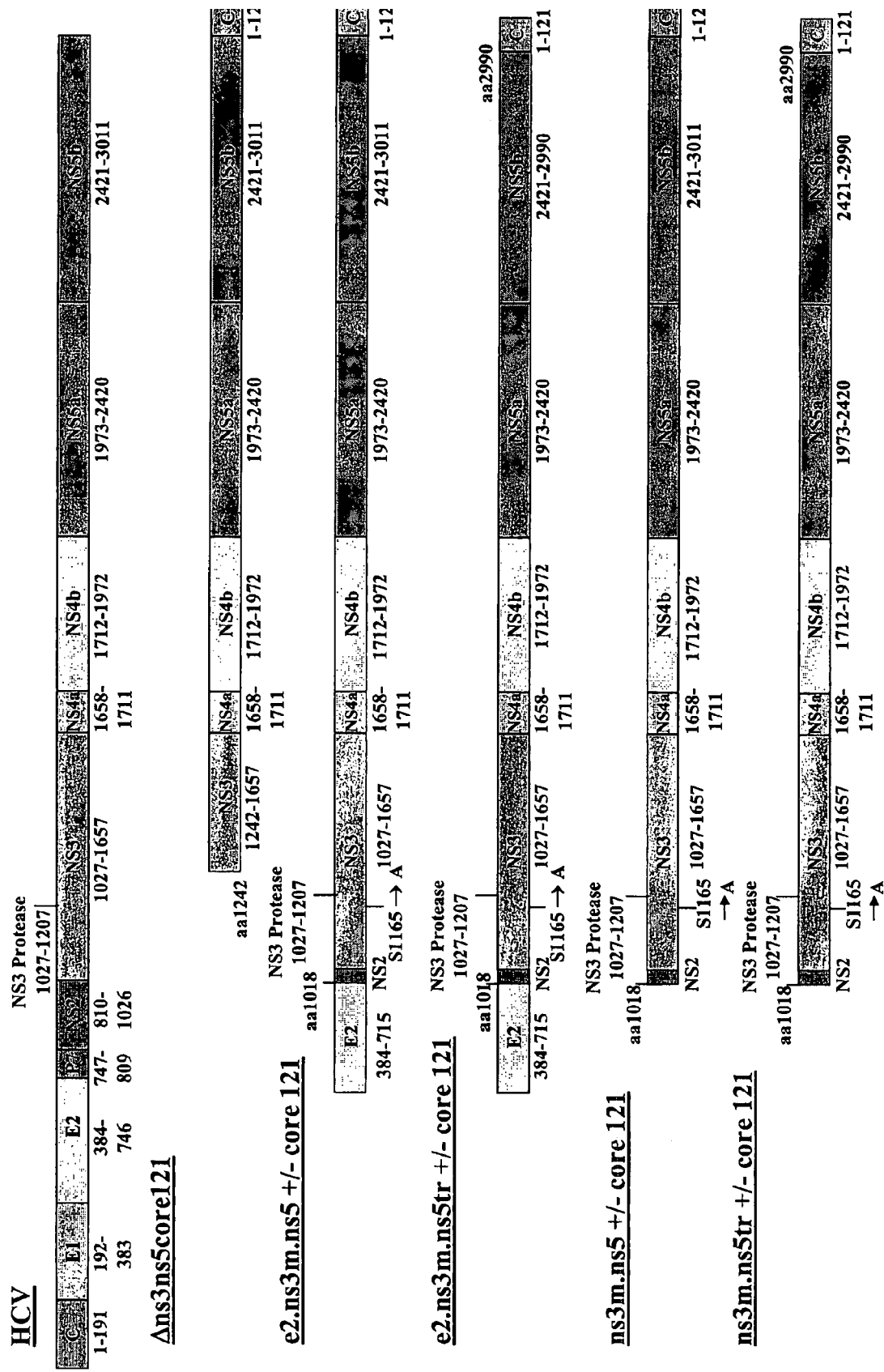
FIG. 11 depicts the genetic organization of exemplary HCV fusion polypeptides of the present invention.

Using similar approaches, other polynucleotides were constructed to encode other fusion polypeptides as shown in FIG. 11 and inserted into the expression plasmid vector pBS24.1. These other fusion proteins are:

Δns3 ns5core121 or ΔNS3-NS5.core121 (aa1242-aa1657 of NS3, aa1658-aa1972 of NS4, aa1973-aa2990 of NS5 and aa1-aa121 of core);

ns3m.ns5–core or NS3m-NS5 (aa1018-aa1026 of NS2, aa1027-aa1657 of NS3, aa1658-aa1972 of NS4 and aa1973-aa3011 of NS5);

ns3m.ns5tr–core or NS3m-NS5tr (aa1018-aa1026 of NS2, aa1027-aa1657 of NS3, aa1658-aa1972 of NS4 and aa1973-aa2990 of NS5);

ns3m.ns5+core121 or NS3m-NS5.core121 (aa1018-aa1026 of NS2, aa1027-aa1657 of NS3, aa1658-aa1972 of NS4, aa1973-aa3011 of NS5 and aa1-aa121 of core);

ns3m.ns5tr+core or NS3m-NS5tr.core121 (aa1018-aa1026 of NS2, aa1027-aa1657 of NS3, aa1658-aa1972 of NS4, aa1973-aa2990 of NS5 and aa1-aa121 of core);

e2.ns3m.ns5–core or E2.NS3m-NS5 (methionine, aa384-aa715 of E2, aa1018-aa1026 of NS2, aa1027-aa1657 of NS3, aa1658-aa1972 of NS4 and aa1973-aa3011 of NS5);

e2.ns3m.ns5tr–core or E2.NS3m-NS5tr (methionine, aa384-aa715 of E2, aa1018-aa1026 of NS2, aa1027-aa1657 of NS3, aa1658-aa1972 of NS4 and aa1973-aa2990 of NS5); and e2.ns3m.ns5+core or E2.NS3m-NS5.core121 (methionine, aa384-aa715 of E2, aa1018-aa1026 of NS2, aa1027-aa1657 of NS3, aa1658-aa1972 of NS4, aa1973-aa3011 of NS5 and aa1-aa121 of core).

All of these fusion proteins had Arg as amino acid 9 of the core sequence and Thr as amino acid 11 of the core sequence. All except Δns3 ns5core121 had the Ser1165-Ala mutation in NS3.

Expression and Detection of HCV Fusion Proteins

The expression plasmids with the various constructs described above were transformed into yeast and expressed as demonstrated in FIGS. 10a to 10d.

The fusion proteins were expressed from the yeast expression plasmids using the ADH2/GAPDH promoter. For example, the E2NS2NS3*NS4NS5tr.core121 fusion protein was expressed from plasmid pd.e2 ns3$_m$ns5tr.c121.

*S. cerevisiae* strain AD3* (genotype matα,leu2,trp1,ura3-52,prb-1122,pep4-3,prc1-407, cir°,trp+, :DM15[GAP/ADR], originally derived from strain BJ2168 as described in U.S. Pat. No. 6,458,527 section 4.2.4.4), was transformed with the pd.e2 ns3$_m$ns5tr.c121 yeast expression plasmid or other plasmids as described above. Yeast cells were transformed with the expression plasmids using a lithium acetate protocol. Ura-transformants were streaked for single colonies and patched onto leu⁻/8% glucose plates to increase plasmid copy number. Leu⁻starter cultures were grown for 24-48 hours at 30° C. and then diluted 1:20 in YEPD (yeast extract bactopeptone 2% glucose) media. Cells were grown at either 25° C. or 30° C. for 48 hours and harvested after depletion of glucose in the medium.

For experiments whose results are shown in FIGS. 10a-10d, to test for expression of the HCV fusion polypeptide encoded by plasmid e2 ns3$_m$ns5tr.c121 as well as the other fusion polypeptides as described above, yeast transformants were inoculated into 3 ml of leu⁻/8% glucose media from either freshly grown single colonies, frozen glycerol stocks or days-old liquid cultures. These cultures, referred to as "starter cultures", were grown at 30° C. for 36-48 hrs. Then 1.5 ml of each starter culture was inoculated into 28.5 ml YEPD and grown at 25° C. for 48-50 hours. Equal aliquots of cells (same volumes of packed cells) were lysed with glass beads in lysis buffer (10 mM Tris-Cl pH 7.5, 1 mM EDTA, 10 mM DTT, 1 mM PMSF). Lysed yeast cell samples were centrifuged for 30 min. at 14K rpm, supernatant was discarded and insoluble yeast pellet (IP) was resuspended in 500 μl pH 12 SDS sample buffer+50 mM DTT, placed on a tilt shaker for 1 hr. The resuspended IP samples were sonicated for 8-10 seconds (Virsonic 60, set at 17), and additional 500 μl pH12 SDS sample buffer+50 mM DTT were added to the sonicated samples. The samples were centrifuged for 1 min. in a microfuge to pellet debris. Five microliters of each sample were loaded on SDS Tris-Glycine gels (4-20%) without boiling.

After electrophoresis, gels were either stained with Coomassie blue (shown on the left in each of FIGS. 10a-10d) or blotted to nitrocellulose filter paper and incubated with a rabbit anti-HCV Helicase antibody using the Western Blotting technique (shown on the right in each of FIGS. 10a-10d). The primary antibody, rabbit anti-Helicase #1 antibody (BAbCO, Berkeley Antibody Company, Richmond, Calif.) was used at a dilution of 1:10,000. The blots were then detected with a goat anti-rabbit IgG (H+L) HRP-conjugate at a 1:1000 dilution and developed with HRP color development reagent.

Figure 10A:
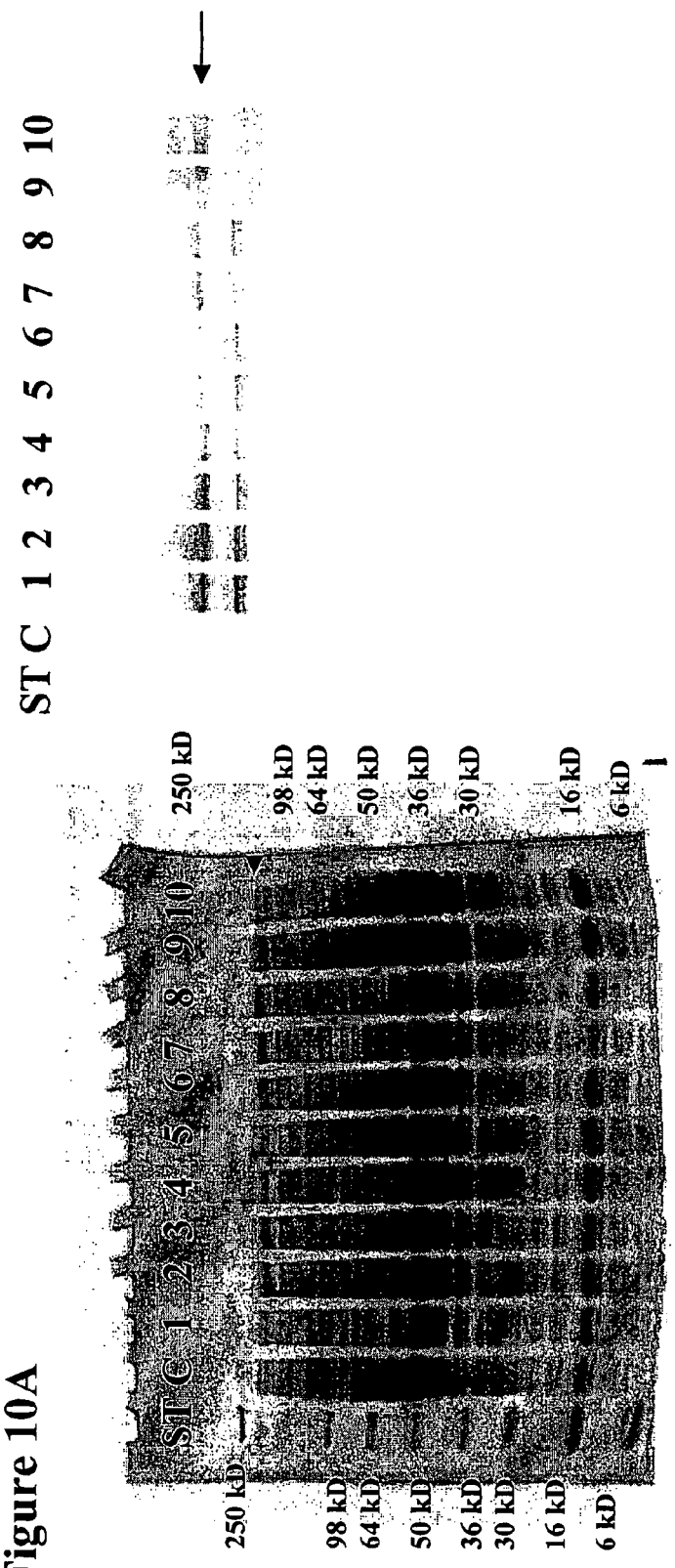
FIGS. 10A to 10D show the results of expression of exemplary HCV fusion polypeptides of the invention in yeast cells.

FIG. 10A is a comparison of the expression levels of the HCV fusion polypeptides that do not have the E2 ectodomain of aa384-715 at the amino terminus. The starter cultures for all the samples shown in this figure were inoculated from the freshly grown single colonies. All samples represent the insoluble pellet (IP), resuspended in 1 ml pH12 SB+DTT for 1 hr and sonicated for ~8 seconds. The samples shown in FIG. 10A are:
 Lane ST, molecular weight standard;
 Lane C, pAB24 plasmid vector control;
 Lane 1, ns3m-ns5 (219.3 kD), colony A;
 Lane 2, ns3m-ns5 (219.3 kD), colony B;
 Lane 3, ns3m-ns5tr (217.0 kD), colony A;
 Lane 4, ns3m-ns5tr (217.0 kD), colony B;
 Lane 5, ns3m-ns5.core121 (233.6 kD), colony A;
 Lane 6, ns3m-ns5.core121 (233.6 kD), colony B;
 Lane 7, ns3m-ns5tr.core121 (230.3 kD), colony A;
 Lane 8, ns3m-ns5tr.core121 (230.3 kD), colony B;
 Lane 9, Δns3-ns5.core121 (208.0 kD), colony A;
 Lane 10, Δns3-ns5.core121 (208.0 kD), colony B.

Figure 10B:
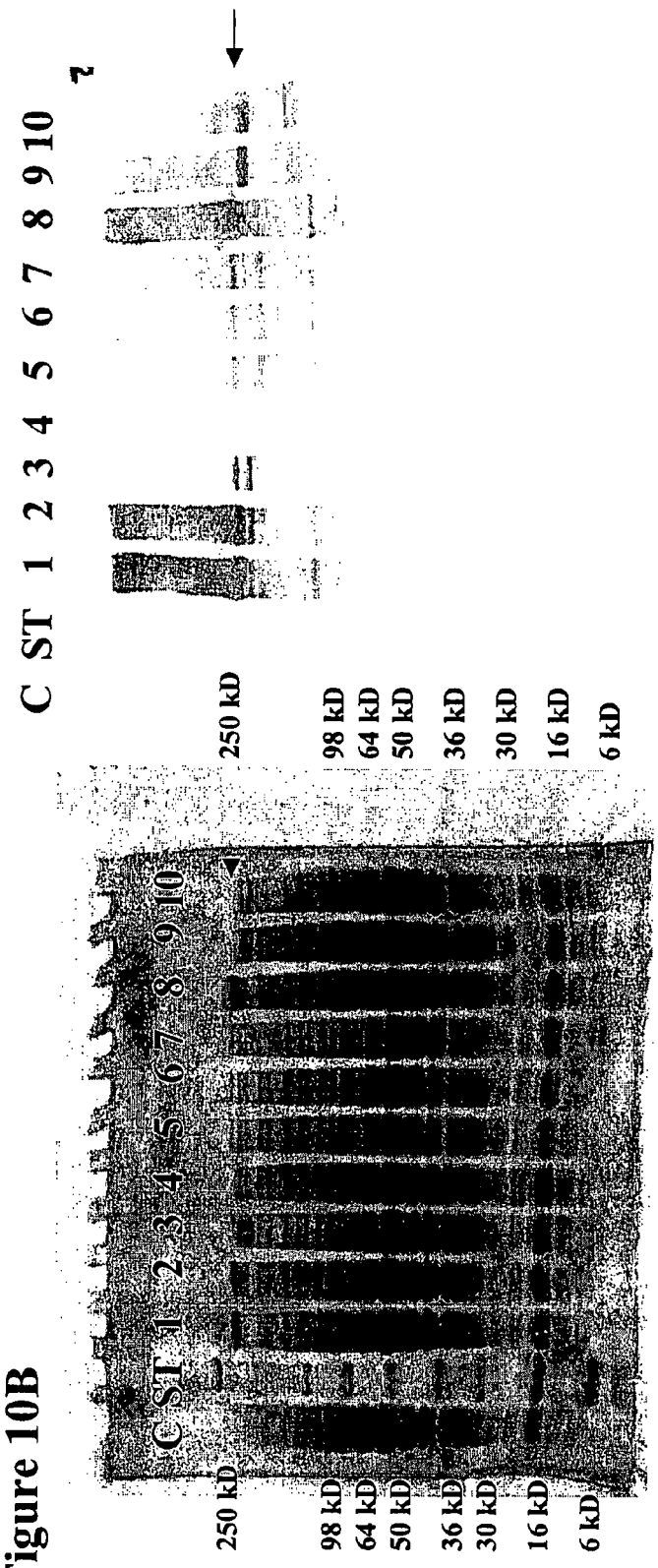

FIG. 10B is a comparison of the expression levels of the fusion polypeptides that have the E2 ectodomain of aa384-715 at the amino terminus with each other and with the Δns3-ns5.core121 polypeptide which serves as a control. The starter cultures for all the samples shown in this figure were inoculated from the freshly grown single colonies. All samples represent the insoluble pellet (IP), resuspended in 1 ml pH12 SB+DTT for 1 hr and sonicated for ~8 seconds. The samples shown in FIG. 10B are:
 Lane C, pAB24 plasmid vector control;
 Lane ST, molecular weight standard;
 Lane 1, e2.ns3m-ns5 (256.0 kD), colony A;
 Lane 2, e2.ns3m-ns5 (256.0 kD), colony B;
 Lane 3, e2.ns3m-ns5tr (253.6 kD), colony A;
 Lane 4, e2.ns3m-ns5tr (253.6 kD), colony B;
 Lane 5, e2.ns3m-ns5.core121 (269.2 kD), colony A;
 Lane 6, e2.ns3m-ns5.core121 (269.2 kD), colony B;
 Lane 7, e2.ns3m-ns5tr.core121 (266.3 kD), colony A;
 Lane 8, e2.ns3m-ns5tr.core121 (266.3 kD), colony B;
 Lane 9, Δns3-ns5.core121 (208.0 kD), colony A;
 Lane 10, Δns3-ns5.core121 (208.0 kD), colony B.

Figure 10C:
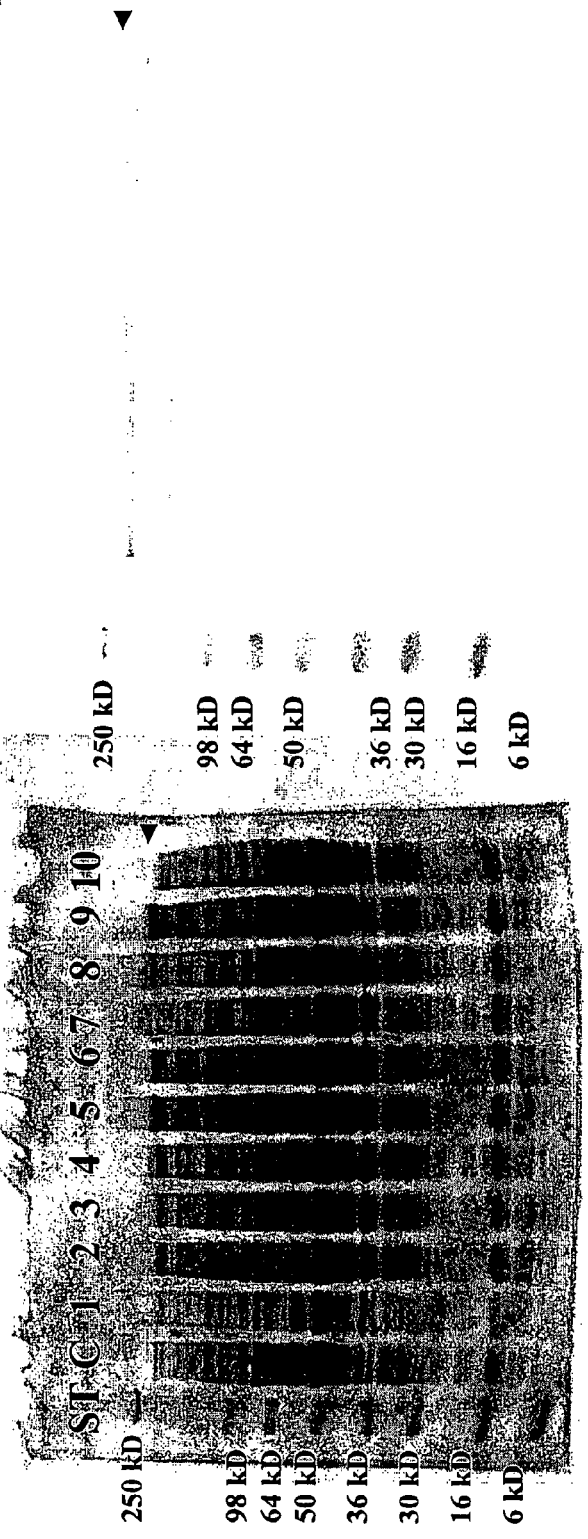
Figure 10D:
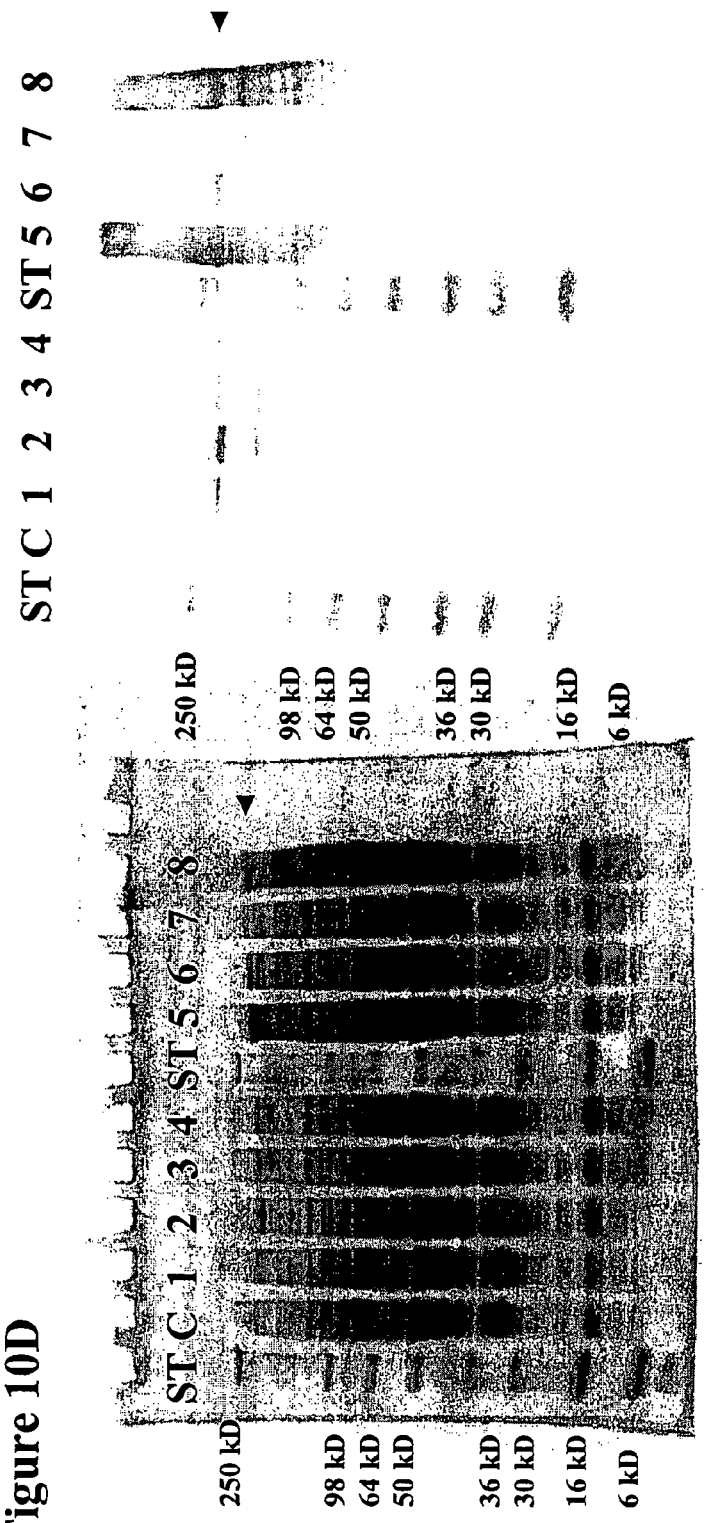

FIG. 10C is a comparison of expression and detection of various fusion polypeptides with inocula from frozen glycerol stocks except pAB24 which was inoculated from a freshly grown colony. FIG. 10D is a comparison of the same fusion proteins with inocula from days-old liquid cultures instead of frozen stocks or single colonies. These were performed to confirm that future expression and detection levels of the desired fusion polypeptides can be maintained through multiple generational growths from both frozen stocks, previously prepared liquid cultures and fresh single colonies.

The samples shown in FIG. 10C are:
 Lane ST, molecular weight standard;
 Lane C, pAB24 plasmid vector control;
 Lane 1, ns3m-ns5 (219.3 kD), frozen stock A;
 Lane 2, ns3m-ns5 (219.3 kD), frozen stock B;
 Lane 3, ns3m-ns5tr.core121 (230.3 kD), frozen stock A;
 Lane 4, ns3m-ns5tr.core121 (230.3 kD), frozen stock B;
 Lane 5, e2.ns3m-ns5 (256.0 kD), frozen stock A;
 Lane 6, e2.ns3m-ns5 (256.0 kD), frozen stock B;
 Lane 7, e2.ns3m-ns5tr.core121 (266.3 kD), frozen stock A;
 Lane 8, e2.ns3m-ns5tr.core121 (266.3 kD), frozen stock B;
 Lane 9, e2.ns3m-ns5tr.core121 (266.3 kD), frozen stock C;
 Lane 10, Δns3-ns5.core121 (208.0 kD), colony.

The samples shown in FIG. 10D are:
 Lane ST, molecular weight standard;
 Lane C, pAB24 plasmid vector control;
 Lane 1, ns3m-ns5 (219.3 kD), liquid culture A;
 Lane 2, ns3m-ns5 (219.3 kD), liquid culture B;
 Lane 3, ns3m-ns5tr.core121 (230.3 kD), liquid culture A;
 Lane 4, ns3m-ns5tr.core121 (230.3 kD), liquid culture B;
 Lane 5, e2.ns3m-ns5 (256.0 kD), liquid culture A;
 Lane 6, e2.ns3m-ns5 (256.0 kD), liquid culture B;
 Lane 7, e2.ns3m-ns5tr.core121 (266.3 kD), liquid culture A;
 Lane 8, e2.ns3m-ns5tr.core121 (266.3 kD), liquid culture B;

Using Δns3-ns5.core121 as the control for the amount of expression level detected by Western Analysis, the amounts of fusion polypeptides detected in FIGS. 10a and 10b were estimated by visual inspection, and the relative amounts are summarized in Table 2 below.

TABLE 2

The summary of HCV fusion polypeptide expression levels detected by Western Analysis, compared to the Δns3-ns5.core121 fusion polyprotein control.

| Fusion Protein | Expression Levels vs. Control (Western Analysis) |
|---|---|
| Δns3-ns5.core121 control | 1X |
| ns3m-ns5 | 1/3X* |

TABLE 2-continued

The summary of HCV fusion polypeptide expression levels detected by Western Analysis, compared to the Ans3-ns5.core121 fusion polyprotein control.

| Fusion Protein | Expression Levels vs. Control (Western Analysis) |
|---|---|
| ns3m-ns5tr | 1/4X* |
| ns3m-ns5.core121 | 1/5X* |
| ns3m-ns5tr.core121 | 1/3X* |
| e2.ns3m-ns5 | 2X |
| e2.ns3m-ns5tr | 1/4X |
| e2.ns3m-ns5.core121 | 1/4X |
| e2.ns3m-ns5tr.core121 | 2X |

*Degradation amounts and patterns consistent throughout all samples in Western Analysis The results shown in FIGS. 10A, 10B and Table 2 indicate that e2.ns3m-ns5 and e2.ns3m-ns5tr core121 were expressed at particularly high levels, especially when compared to ns3m-ns5 and ns3m-ns5tr core121 which do not have the E2 ectodomain of aa384-715 at the amino terminus.

Production of the HCV Fusion Polypeptide-ISCOM Formulations

The E2NS2NS3*NS4NS5tcore121 fusion protein, or e2.ns3m-ns5tr.core121, produced as described above was used to produce HCV fusion-ISCOMs as follows. The fusion-ISCOM formulations were prepared by mixing the fusion protein with a preformed ISCOMATRIX (empty ISCOMs) utilizing ionic interactions to maximize association between the fusion protein and the adjuvant. ISCOMATRIX is prepared essentially as described in Coulter et al. (1998) *Vaccine* 16:1243. Further methods for production of HCV fusion polypeptides plus ISCOMs are described herein. The fusion-ISCOM formulations are also referred to herein as "IMX/poly" or "IMX-poly". In one embodiment, CpG was added to the formulation, and the complete formulation was named "IMX/poly/CpG".

EXAMPLE 2

Ability of Fusion Polypeptide Vaccine Formulations to Prime T-cell Responses

Immunization

Figure 8:
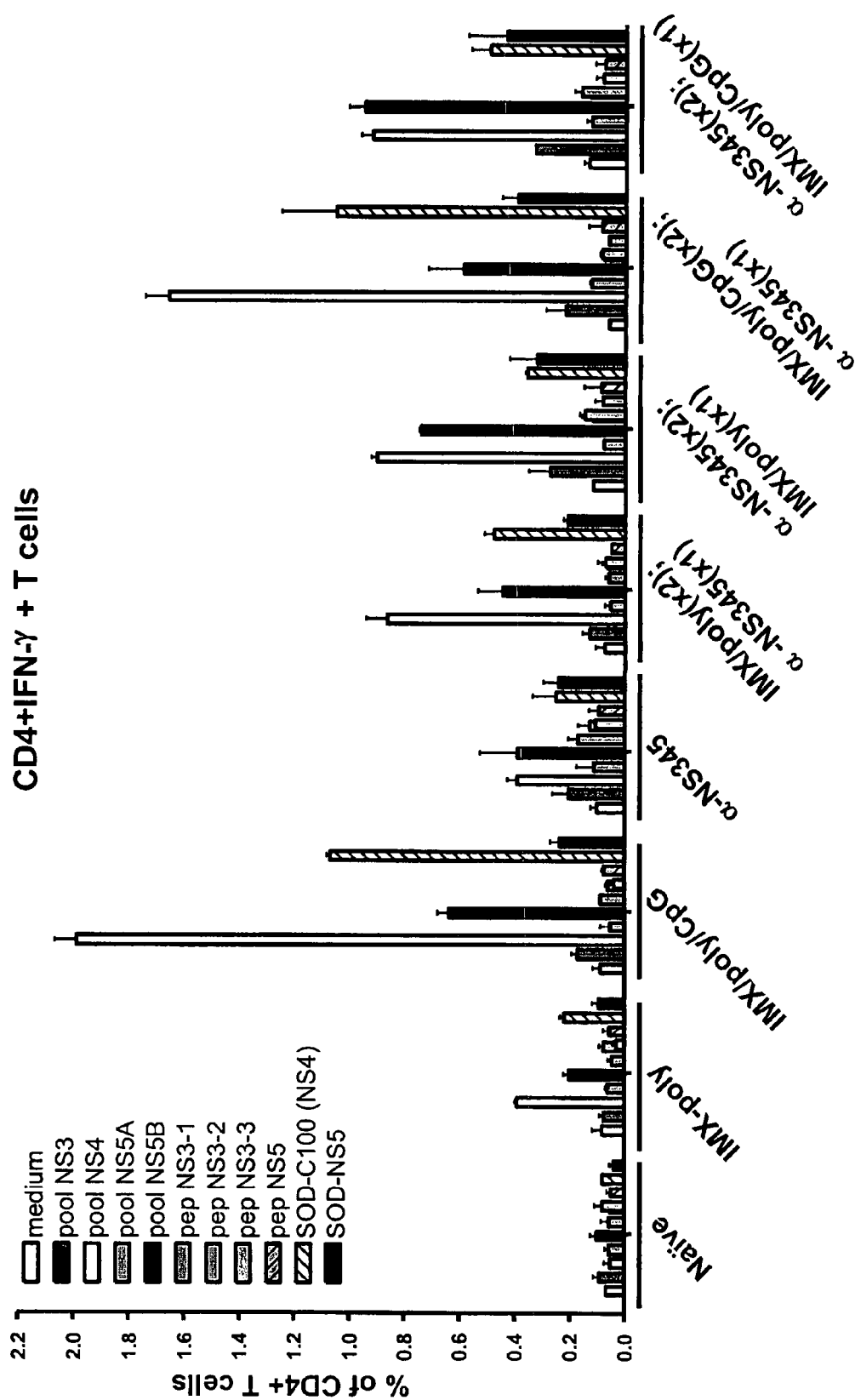
FIG. 8 is a graphical representation of T cells generated in mice in response to immunization with an exemplary HCV fusion polypeptide of the invention.
Figure 9:
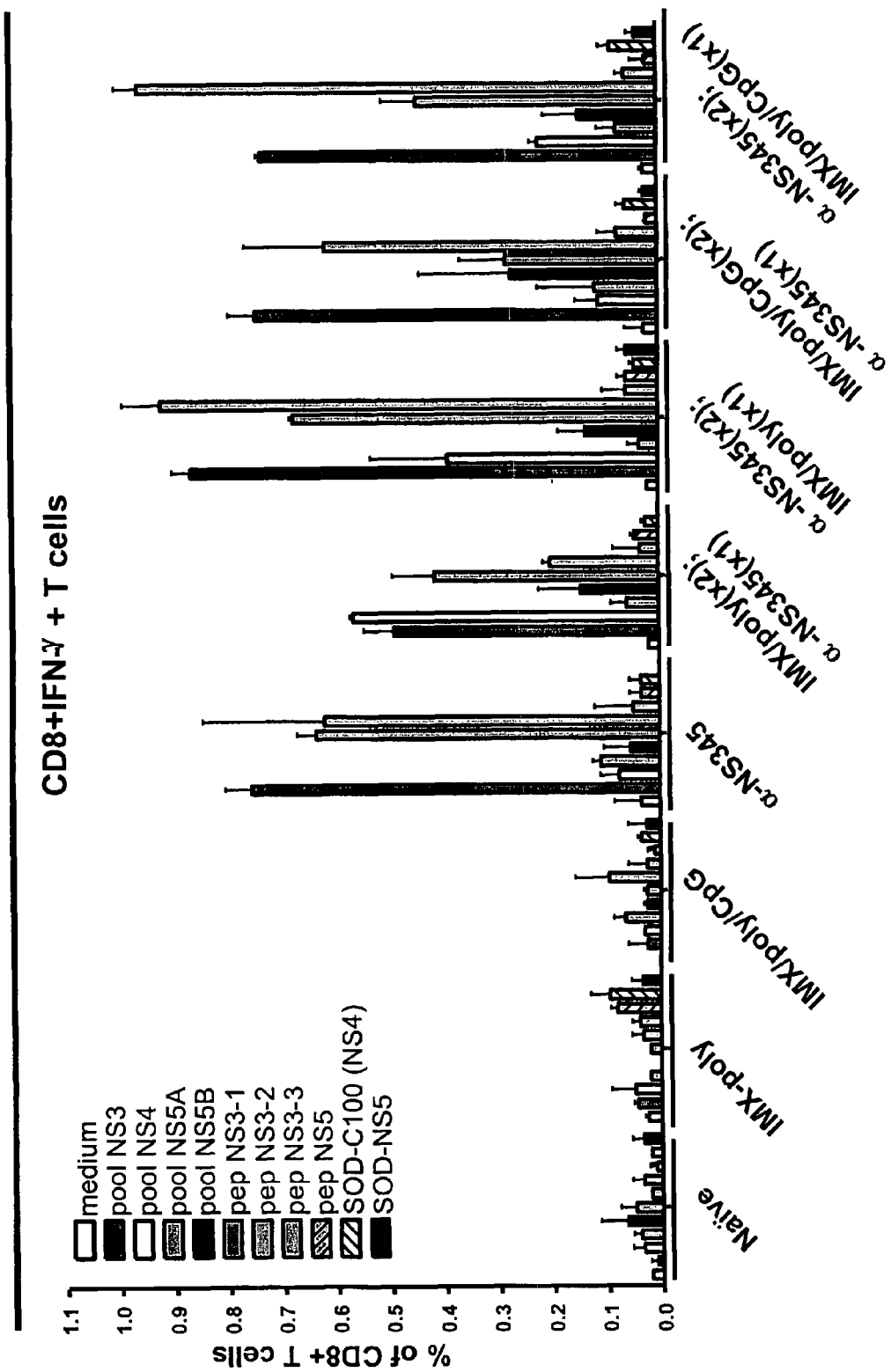
FIG. 9 is a graphical representation of T cells generated in mice in response to immunization with an exemplary HCV fusion polypeptide of the invention.

The following studies were conducted to determine the ability of E2NS3*NS4NS5tcore121/ISCOMS, or IMX/poly, with or without CpG, to prime HCV-specific immune responses, especially T cell responses. In addition, primary immunizations with IMX/poly followed by boosts with alphavirus replicons encoding wildtype NS345 ("α-NS345"), or vice versa (priming with α-NS345 and boosting with fusion-ISCOM formulations), were tested for their effects on HCV-specific T cell responses. The results are shown in FIG. 8 (CD4+ T cell responses) and FIG. 9 (CD8+ T cell responses).

10 female BALB/c mice per group were injected intramuscularly (IM) in the tibialis anterior muscle in a total volume of 100 μl (i.e. 50 μl per thigh) with the indicated vaccine formulations (FIGS. 8 and 9) at weeks 0, 3, and 6, and the sera were collected at weeks 2, 5, and 8. For the prime-boost studies, the mice were primed at week 0 and 3, and boosted at week 6. For non-structural protein (NS345), 5E6 replication particles of VEE/SIN-NS345 and 50 μg of polyprotein were mixed with 5 μg of IMX (Pearse, M. J., and D. Drane. 2005. Adv Drug Deliv Rev 57:465-74; Pearse, M. J., and D. Drane. 2004. Vaccine 22:2391-5; Polakos, et al. 2001. J Immunol 166:3589-98) with or without 10 μg of CpG for injection. The mice were sacrificed at week 8 for detecting T cell responses in spleen and antibody responses in serum.

Intracellular Staining (ICS)

Spleen cells (1E6) were stimulated with 10 μg/ml of the peptides or proteins indicated in Table 3 for 6 hours at 37° C. in the presence of anti-CD28 antibody (1 μg/ml) (BD Biosciences, San Jose, Calif.) and Brefeldin A (BD Biosciences, San Jose, Calif.), and then stained with antibodies against CD4 (anti-CD4 allophycocyanin conjugate, clone SK3, Becton Dickinson, San Jose, Calif.) and CD8 (anti-CD8α PerCP conjugate, clone SK1, Becton Dickinson), permeabilized with Cytofix/Cytoperm (Pharmingen), and IFN-γ (clone 4S.B3, phycoerythrin conjugate, Pharmingen). Stained cells were analyzed with a FACSCalibur™ flow cytometer (Becton Dickinson). The mean frequencies of cytokine-positive cells were calculated for each pair of duplicates. The antigen-specific frequency was determined by comparing unstimulated mean frequency (no peptide) with the stimulated mean frequency (with HCV peptides, Table 3), and $p<0.05$ is considered statistically significant by t-test.

TABLE 3

Peptides or proteins used to stimulate T cells.

| Name | Peptide or protein information | Reference |
|---|---|---|
| NS3 pool | 20 mer overlapping peptides covering NS3 | |
| NS4 pool | 20 mer overlapping peptides covering NS4 | |
| NS5A pool | 20 mer overlapping peptides covering NS5A | |
| NS5B pool | 20 mer overlapping peptides covering NS5B | |
| NS3-1 pep | LVALGINAVAYYRGL | (6) |
| NS3-2 pep | TTVRLRAYMNTPGLP | (6) |
| NS3-3 pep | SSPPVVPQSF | (1, 2) |
| NS5B pep | MSYSWTGALVTPCAAE | (7) |
| SOD-C100 (NS4) | Recombinant NS4 protein purified from yeast (HCV 1a a.a. 1569-1931) | (3, 4) |
| SOD-NS5 | Recombinant NS5A/B protein purified from yeast (HCV 1a a. a. 2054-2995) | (5) |

References for Example 2:
1. Arribillaga, L., et al 2002. Vaccine 21: 202-10.
2. Arribillaga, L., et al 2005. Vaccine 23: 3493-9.
3. Kuo, G., et al. 1989. Science 244: 362-4.
4. Minutello, M. A., et al. 1993.. J Exp Med 178: 17-25.
5. Saracco, G., et al. 1994. Liver 14: 65-70.
6. Simon, B. E., et al. 2003. Infect Immun 71: 6372-80.
7. Uno-Furuta, S., et al.. 2003. Vaccine 21: 3149-56.

The results shown in FIG. 8 indicate that IMX-poly without CpG was able to induce HCV-specific CD4+ T cell responses as compared to the negative control. Addition of CpG to IMX-poly increased CD4+ T cell responses further. Priming and boosting with IMX-poly and α-NS345 in various orders with or without CpG also induced significant CD4+ T cell responses.

EXAMPLE 3

Alphaviruses Expressing Corresponding NS epitopes

Alphavirus replicon particles, for example, SINCR (DC+) and SINCR (LP) are prepared as described in Polo et al., *Proc. Natl. Acad. Sci. USA* (1999) 96:4598-4603. The alphavirus replicons can contain all or part or include additional HCV epitopes when compared to the amino acids of the immunogenic HCV fusion polypeptide compositions described herein. The α-NS345 replicons used in Example 2 contained complete sequences of NS3, 4 and 5 (amino acids 1027 to 1657 of NS3, amino acids 1658 to 1972 of NS4, amino acids 1973 to 3011 of NS5), and there was no mutation in NS3. Such alphavirus particles can be used in combination with the HCV fusion polypeptides of the invention as part of a prime boost immunization strategy, as shown in Example 2.

EXAMPLE 4

Production of Modified E2NS2NS3*NS4NS5t and E2NS2NS3*NS4NS5tCore Polynucleotides and Polypeptides E2 in the following examples represents a C-terminally truncated E2 molecule that includes amino acids 384-715, numbered relative to the full-length HCV-1 polyprotein. The E2 nucleic acid in one embodiment was fused to a nucleic acid encoding amino acids 1018 to 1026 of the NS2 protein, which is fused to a nucleic acid encoding amino acids 1027 to 3011 or 2990 of the polyprotein, fused to a nucleic acid encoding the core 121 amino acids of the polyprotein.

These two versions of HCV fusion polypeptides are found in FIG. 11 as "e2.ns3m.ns5−/−core 121" (the full length version of NS5b) and "e2.ns3m.ns5tr−/−core 121" (truncated NS5b) modified NS3 polypeptide. The constructs comprising E2 amino acids sequences shown include core 1 to 121 as described herein.

The portion of the nucleic acid encoding amino acids 1027 to 2990 of the polyprotein encodes a modified NS3 protein (1027-1657), NS4aNS4b (1658-1972) and NS5aNS5b (1973-2090), wherein the NS5b protein is truncated.

The nucleic acid encoding amino acids 1027 to 3011 of the polyprotein encodes a modified NS3 protein (1027-1657), NS4aNS4b (1658-1972) and NS5aNS5b (1973-3011)" wherein the NS5b is full length.

The modified NS3 portions of the HCV fusion polypeptides comprise a Ser1165 to Alanine mutation that results in loss of protease activity.

Additional fusion proteins shown in FIG. 11 contain the last nine amino acids of NS2 fused to (1) the nucleic acid encoding amino acids 1027 to 3011 of the polyprotein encodes a modified NS3 protein (1027-1657), NS4aNS4b (1658-1972) and NS5aNS5b (1973-3011), wherein the NS5b is full length ("ns3m.ns5+/−core 121"), or (2) the nucleic acid encoding amino acids 1027 to 2990 of the polyprotein encodes a modified NS3 protein (1027-1657), NS4aNS4b (1658-1972) and NS5aNS5b (1973-2090), wherein the NS5b protein is truncated ("ns3m.ns5tr+/−core 121").

Addition of the last nine amino acids of NS2 to the fusion proteins described herein provides a naturally occurring methionine upstream of the NS3 gene portion and downstream of the E2 portion of the polyprotein, thus minimizing changes in epitopes from the naturally occurring HCV polyprotein.

In one embodiment, the invention provides modified HCV fusion polypeptides that allow for improved protein expression in yeast.

Since the N-terminus of the HCV-1 NS3 domain (aa1027-aa1657) encodes a trypsin-like serine protease, the natural $Ser_{1165}$ of the protease catalytic triad is mutated to Ala to prevent autoproteolysis of the HCV e2 ns3$_m$ns5tr.c121 fusion polypeptide.

Thus, nucleic acids encoding and HCV fusion polypeptides and polynucleotides encoding the polypeptides are disclosed. Although preferred embodiments of the subject invention have been described in some detail, it is understood that obvious variations can be made without departing from the spirit and the scope of the invention as defined by the claims.

---

SEQUENCE LISTING

```
<160> NUMBER OF SEQ ID NOS: 14

<210> SEQ ID NO 1
<211> LENGTH: 9
<212> TYPE: PRT
<213> ORGANISM: Artificial
<220> FEATURE:
<223> OTHER INFORMATION: synthetic epitope recognized by a T cell
      receptor

<400> SEQUENCE: 1

His Glu Tyr Pro Val Gly Ser Gln Leu
1               5

<210> SEQ ID NO 2
<211> LENGTH: 15
<212> TYPE: PRT
<213> ORGANISM: Artificial
<220> FEATURE:
<223> OTHER INFORMATION: synthetic epitope recognized by a T cell
      receptor

<400> SEQUENCE: 2
```

```
Ala Glu Leu Ile Glu Ala Asn Leu Leu Trp Arg Gln Glu Met Gly
1               5                  10                 15

<210> SEQ ID NO 3
<211> LENGTH: 546
<212> TYPE: DNA
<213> ORGANISM: Hepatitis C virus
<220> FEATURE:
<221> NAME/KEY: CDS
<222> LOCATION: (1)..(546)

<400> SEQUENCE: 3 atg gcg ccc atc acg gcg tac gcc cag cag aca agg ggc ctc cta ggg      48
Met Ala Pro Ile Thr Ala Tyr Ala Gln Gln Thr Arg Gly Leu Leu Gly
1               5                  10                 15 tgc ata atc acc agc cta act ggc cgg gac aaa aac caa gtg gag ggt      96
Cys Ile Ile Thr Ser Leu Thr Gly Arg Asp Lys Asn Gln Val Glu Gly
            20                  25                  30 gag gtc cag att gtg tca act gct gcc caa acc ttc ctg gca acg tgc     144
Glu Val Gln Ile Val Ser Thr Ala Ala Gln Thr Phe Leu Ala Thr Cys
        35                  40                  45 atc aat ggg gtg tgc tgg act gtc tac cac ggg gcc gga acg agg acc     192
Ile Asn Gly Val Cys Trp Thr Val Tyr His Gly Ala Gly Thr Arg Thr
    50                  55                  60 atc gcg tca ccc aag ggt cct gtc atc cag atg tat acc aat gta gac     240
Ile Ala Ser Pro Lys Gly Pro Val Ile Gln Met Tyr Thr Asn Val Asp
65                  70                  75                  80 caa gac ctt gtg ggc tgg ccc gct ccg caa ggt agc cga tca ttg aca     288
Gln Asp Leu Val Gly Trp Pro Ala Pro Gln Gly Ser Arg Ser Leu Thr
                85                  90                  95 ccc tgc act tgc ggc tcc tcg gac ctt tac ctg gtc acg agg cac gcc     336
Pro Cys Thr Cys Gly Ser Ser Asp Leu Tyr Leu Val Thr Arg His Ala
            100                 105                 110 gat gtc att ccc gtg cgc cgg cgg ggt gat agc agg ggc agc ctg ctg     384
Asp Val Ile Pro Val Arg Arg Arg Gly Asp Ser Arg Gly Ser Leu Leu
        115                 120                 125 tcg ccc cgg ccc att tcc tac ttg aaa ggc tcc tcg ggg ggt ccg ctg     432
Ser Pro Arg Pro Ile Ser Tyr Leu Lys Gly Ser Ser Gly Gly Pro Leu
    130                 135                 140 ttg tgc ccc gcg ggg cac gcc gtg ggc ata ttt agg gcc gcg gtg tgc     480
Leu Cys Pro Ala Gly His Ala Val Gly Ile Phe Arg Ala Ala Val Cys
145                 150                 155                 160 acc cgt gga gtg gct aag gcg gtg gac ttt atc cct gtg gag aac cta     528
Thr Arg Gly Val Ala Lys Ala Val Asp Phe Ile Pro Val Glu Asn Leu
                165                 170                 175 gag aca acc atg agg tcc                                              546
Glu Thr Thr Met Arg Ser
            180

<210> SEQ ID NO 4
<211> LENGTH: 182
<212> TYPE: PRT
<213> ORGANISM: Hepatitis C virus

<400> SEQUENCE: 4

Met Ala Pro Ile Thr Ala Tyr Ala Gln Gln Thr Arg Gly Leu Leu Gly
1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
```

```
                   50                  55                  60
Ile Ala Ser Pro Lys Gly Pro Val Ile Gln Met Tyr Thr Asn Val Asp
 65                  70                  75                  80

```
                   -continued
      145             150             155             160
gac gaa ctc gcc gca aag ctg gtc gca ttg ggc atc aat gcc gtg gcc    528
Asp Glu Leu Ala Ala Lys Leu Val Ala Leu Gly Ile Asn Ala Val Ala
                165             170             175 tac tac cgc ggt ctt gac gtg tcc gtc atc ccg acc agc ggc gat gtt    576
Tyr Tyr Arg Gly Leu Asp Val Ser Val Ile Pro Thr Ser Gly Asp Val
            180             185             190 gtc gtc gtg gca acc gat gcc ctc atg acc ggc tat acc ggc gac ttc    624
Val Val Val Ala Thr Asp Ala Leu Met Thr Gly Tyr Thr Gly Asp Phe
        195             200             205 gac tcg gtg ata gac tgc aat acg tgt gtc acc cag aca gtc gat ttc    672
Asp Ser Val Ile Asp Cys Asn Thr Cys Val Thr Gln Thr Val Asp Phe
    210             215             220 agc ctt gac cct acc ttc acc att gag aca atc acg ctc ccc caa gat    720
Ser Leu Asp Pro Thr Phe Thr Ile Glu Thr Ile Thr Leu Pro Gln Asp
225             230             235             240 gct gtc tcc cgc act caa cgt cgg agg act ggc agg ggg aag cca         768
Ala Val Ser Arg Thr Gln Arg Arg Gly Arg Thr Gly Arg Gly Lys Pro
                245             250             255 ggc atc tac aga ttt gtg gca ccg ggg gag cgc ccc tcc ggc atg ttc    816
Gly Ile Tyr Arg Phe Val Ala Pro Gly Glu Arg Pro Ser Gly Met Phe
            260             265             270 gac tcg tcc gtc ctc tgt gag tgc tat gac gca ggc tgt gct tgg tat    864
Asp Ser Ser Val Leu Cys Glu Cys Tyr Asp Ala Gly Cys Ala Trp Tyr
        275             280             285 gag ctc acg ccc gcc gag act aca gtt agg cta cga gcg tac atg aac    912
Glu Leu Thr Pro Ala Glu Thr Thr Val Arg Leu Arg Ala Tyr Met Asn
    290             295             300 acc ccg ggg ctt ccc gtg tgc cag gac cat ctt gaa ttt tgg gag ggc    960
Thr Pro Gly Leu Pro Val Cys Gln Asp His Leu Glu Phe Trp Glu Gly
305             310             315             320 gtc ttt aca ggc ctc act cat ata gat gcc cac ttt cta tcc cag aca   1008
Val Phe Thr Gly Leu Thr His Ile Asp Ala His Phe Leu Ser Gln Thr
                325             330             335 aag cag agt ggg gag aac ctt cct tac ctg gta gcg tac caa gcc acc   1056
Lys Gln Ser Gly Glu Asn Leu Pro Tyr Leu Val Ala Tyr Gln Ala Thr
            340             345             350 gtg tgc gct agg gct caa gcc cct ccc cca tcg tgg gac cag atg tgg   1104
Val Cys Ala Arg Ala Gln Ala Pro Pro Pro Ser Trp Asp Gln Met Trp
        355             360             365 aag tgt ttg att cgc ctc aag ccc acc ctc cat ggg cca aca ccc ctg   1152
Lys Cys Leu Ile Arg Leu Lys Pro Thr Leu His Gly Pro Thr Pro Leu
    370             375             380 cta tac aga ctg ggc gct gtt cag aat gaa atc acc ctg acg cac cca   1200
Leu Tyr Arg Leu Gly Ala Val Gln Asn Glu Ile Thr Leu Thr His Pro
385             390             395             400 gtc acc aaa tac atc atg aca tgc atg tcg gcc gac ctg gag gtc gtc   1248
Val Thr Lys Tyr Ile Met Thr Cys Met Ser Ala Asp Leu Glu Val Val
                405             410             415 acg agc acc tgg gtg ctc gtt ggc ggc gtc ctg gct gct ttg gcc gcg   1296
Thr Ser Thr Trp Val Leu Val Gly Gly Val Leu Ala Ala Leu Ala Ala
            420             425             430 tat tgc ctg tca aca ggc tgc gtg gtc ata gtg ggc agg gtc gtc ttg   1344
Tyr Cys Leu Ser Thr Gly Cys Val Val Ile Val Gly Arg Val Val Leu
        435             440             445 tcc ggg aag ccg gca atc ata cct gac agg gaa gtc ctc tac cga gag   1392
Ser Gly Lys Pro Ala Ile Ile Pro Asp Arg Glu Val Leu Tyr Arg Glu
    450             455             460 ttc gat gag atg gaa gag tgc tct cag cac tta ccg tac atc gag caa   1440
Phe Asp Glu Met Glu Glu Cys Ser Gln His Leu Pro Tyr Ile Glu Gln
```

-continued

```
                465                 470                 475                 480
ggg atg atg ctc gcc gag cag ttc aag cag aag gcc ctc ggc ctc ctg         1488
Gly Met Met Leu Ala Glu Gln Phe Lys Gln Lys Ala Leu Gly Leu Leu
                    485                 490                 495 cag acc gcg tcc cgt cag gca gag gtt atc gcc cct gct gtc cag acc         1536
Gln Thr Ala Ser Arg Gln Ala Glu Val Ile Ala Pro Ala Val Gln Thr
        500                 505                 510 aac tgg caa aaa ctc gag acc ttc tgg gcg aag cat atg tgg aac ttc         1584
Asn Trp Gln Lys Leu Glu Thr Phe Trp Ala Lys His Met Trp Asn Phe
    515                 520                 525 atc agt ggg ata caa tac ttg gcg ggc ttg tca acg ctg cct ggt aac         1632
Ile Ser Gly Ile Gln Tyr Leu Ala Gly Leu Ser Thr Leu Pro Gly Asn
530                 535                 540 ccc gcc att gct tca ttg atg gct ttt aca gct gct gtc acc agc cca         1680
Pro Ala Ile Ala Ser Leu Met Ala Phe Thr Ala Ala Val Thr Ser Pro
545                 550                 555                 560 cta acc act agc caa acc ctc ctc ttc aac ata ttg ggg ggg tgg gtg         1728
Leu Thr Thr Ser Gln Thr Leu Leu Phe Asn Ile Leu Gly Gly Trp Val
                    565                 570                 575 gct gcc cag ctc gcc gcc ccc ggt gcc gct act gcc ttt gtg ggc gct         1776
Ala Ala Gln Leu Ala Ala Pro Gly Ala Ala Thr Ala Phe Val Gly Ala
        580                 585                 590 ggc tta gct ggc gcc gcc atc ggc agt gtt gga ctg ggg aag gtc ctc         1824
Gly Leu Ala Gly Ala Ala Ile Gly Ser Val Gly Leu Gly Lys Val Leu
    595                 600                 605 ata gac atc ctt gca ggg tat ggc gcg ggc gtg gcg gga gct ctt gtg         1872
Ile Asp Ile Leu Ala Gly Tyr Gly Ala Gly Val Ala Gly Ala Leu Val
610                 615                 620 gca ttc aag atc atg agc ggt gag gtc ccc tcc acg gag gac ctg gtc         1920
Ala Phe Lys Ile Met Ser Gly Glu Val Pro Ser Thr Glu Asp Leu Val
625                 630                 635                 640 aat cta ctg ccc gcc atc ctc tcg ccc gga gcc ctc gta gtc ggc gtg         1968
Asn Leu Leu Pro Ala Ile Leu Ser Pro Gly Ala Leu Val Val Gly Val
                    645                 650                 655 gtc tgt gca gca ata ctg cgc cgg cac gtt ggc ccg ggc gag ggg gca         2016
Val Cys Ala Ala Ile Leu Arg Arg His Val Gly Pro Gly Glu Gly Ala
        660                 665                 670 gtg cag tgg atg aac cgg ctg ata gcc ttc gcc tcc cgg ggg aac cat         2064
Val Gln Trp Met Asn Arg Leu Ile Ala Phe Ala Ser Arg Gly Asn His
    675                 680                 685 gtt tcc ccc acg cac tac gtg ccg gag agc gat gca gct gcc cgc gtc         2112
Val Ser Pro Thr His Tyr Val Pro Glu Ser Asp Ala Ala Ala Arg Val
690                 695                 700 act gcc ata ctc agc agc ctc act gta acc cag ctc ctg agg cga ctg         2160
Thr Ala Ile Leu Ser Ser Leu Thr Val Thr Gln Leu Leu Arg Arg Leu
705                 710                 715                 720 cac cag tgg ata agc tcg gag tgt acc act cca tgc tcc ggt tcc tgg         2208
His Gln Trp Ile Ser Ser Glu Cys Thr Thr Pro Cys Ser Gly Ser Trp
                    725                 730                 735 cta agg gac atc tgg gac tgg ata tgc gag gtg ttg agc gac ttt aag         2256
Leu Arg Asp Ile Trp Asp Trp Ile Cys Glu Val Leu Ser Asp Phe Lys
        740                 745                 750 acc tgg cta aaa gct aag ctc atg cca cag ctg cct ggg atc ccc ttt         2304
Thr Trp Leu Lys Ala Lys Leu Met Pro Gln Leu Pro Gly Ile Pro Phe
    755                 760                 765 gtg tcc tgc cag cgc ggg tat aag ggg gtc tgg cga ggg gac ggc atc         2352
Val Ser Cys Gln Arg Gly Tyr Lys Gly Val Trp Arg Gly Asp Gly Ile
770                 775                 780 atg cac act cgc tgc cac tgt gga gct gag atc act gga cat gtc aaa         2400
Met His Thr Arg Cys His Cys Gly Ala Glu Ile Thr Gly His Val Lys
```

-continued

| | | |
|---|---|---|
| aac ggg acg atg agg atc gtc ggt cct agg acc tgc agg aac atg tgg<br>Asn Gly Thr Met Arg Ile Val Gly Pro Arg Thr Cys Arg Asn Met Trp<br>                  805                          810                      815 | 2448 |
| agt ggg acc ttc ccc att aat gcc tac acc acg ggc ccc tgt acc ccc<br>Ser Gly Thr Phe Pro Ile Asn Ala Tyr Thr Thr Gly Pro Cys Thr Pro<br>          820                      825                    830 | 2496 |
| ctt cct gcg ccg aac tac acg ttc gcg cta tgg agg gtg tct gca gag<br>Leu Pro Ala Pro Asn Tyr Thr Phe Ala Leu Trp Arg Val Ser Ala Glu<br>               835                      840                  845 | 2544 |
| gaa tac gtg gag ata agg cag gtg ggg gac ttc cac tac gtg acg ggt<br>Glu Tyr Val Glu Ile Arg Gln Val Gly Asp Phe His Tyr Val Thr Gly<br>850                        855                      860 | 2592 |
| atg act act gac aat ctt aaa tgc ccg tgc cag gtc cca tcg ccc gaa<br>Met Thr Thr Asp Asn Leu Lys Cys Pro Cys Gln Val Pro Ser Pro Glu<br>865                        870                      875                  880 | 2640 |
| ttt ttc aca gaa ttg gac ggg gtg cgc cta cat agg ttt gcg ccc ccc<br>Phe Phe Thr Glu Leu Asp Gly Val Arg Leu His Arg Phe Ala Pro Pro<br>                      885                      890                  895 | 2688 |
| tgc aag ccc ttg ctg cgg gag gag gta tca ttc aga gta gga ctc cac<br>Cys Lys Pro Leu Leu Arg Glu Glu Val Ser Phe Arg Val Gly Leu His<br>          900                      905                      910 | 2736 |
| gaa tac ccg gta ggg tcg caa tta cct tgc gag ccc gaa ccg gac gtg<br>Glu Tyr Pro Val Gly Ser Gln Leu Pro Cys Glu Pro Glu Pro Asp Val<br>               915                      920                  925 | 2784 |
| gcc gtg ttg acg tcc atg ctc act gat ccc tcc cat ata aca gca gag<br>Ala Val Leu Thr Ser Met Leu Thr Asp Pro Ser His Ile Thr Ala Glu<br>          930                      935                      940 | 2832 |
| gcg gcc ggg cga agg ttg gcg agg gga tca ccc ccc tct gtg gcc agc<br>Ala Ala Gly Arg Arg Leu Ala Arg Gly Ser Pro Pro Ser Val Ala Ser<br>945                        950                      955                  960 | 2880 |
| tcc tcg gct agc cag cta tcc gct cca tct ctc aag gca act tgc acc<br>Ser Ser Ala Ser Gln Leu Ser Ala Pro Ser Leu Lys Ala Thr Cys Thr<br>               965                      970                  975 | 2928 |
| gct aac cat gac tcc cct gat gct gag ctc ata gag gcc aac ctc cta<br>Ala Asn His Asp Ser Pro Asp Ala Glu Leu Ile Glu Ala Asn Leu Leu<br>               980                      985                  990 | 2976 |
| tgg agg cag gag atg ggc ggc aac atc acc agg gtt gag tca gaa aac<br>Trp Arg Gln Glu Met Gly Gly Asn Ile Thr Arg Val Glu Ser Glu Asn<br>          995                      1000                  1005 | 3024 |
| aaa gtg gtg att ctg gac tcc ttc gat ccg ctt gtg gcg gag gag<br>Lys Val Val Ile Leu Asp Ser Phe Asp Pro Leu Val Ala Glu Glu<br>          1010                      1015                  1020 | 3069 |
| gac gag cgg gag atc tcc gta ccc gca gaa atc ctg cgg aag tct<br>Asp Glu Arg Glu Ile Ser Val Pro Ala Glu Ile Leu Arg Lys Ser<br>          1025                      1030                  1035 | 3114 |
| cgg aga ttc gcc cag gcc ctg ccc gtt tgg gcg cgg ccg gac tat<br>Arg Arg Phe Ala Gln Ala Leu Pro Val Trp Ala Arg Pro Asp Tyr<br>          1040                      1045                  1050 | 3159 |
| aac ccc ccg cta gtg gag acg tgg aaa aag ccc gac tac gaa cca<br>Asn Pro Pro Leu Val Glu Thr Trp Lys Lys Pro Asp Tyr Glu Pro<br>          1055                      1060                  1065 | 3204 |
| cct gtg gtc cat ggc tgc ccg ctt cca cct cca aag tcc cct cct<br>Pro Val Val His Gly Cys Pro Leu Pro Pro Pro Lys Ser Pro Pro<br>          1070                      1075                  1080 | 3249 |
| gtg cct ccg cct cgg aag aag cgg acg gtg gtc ctc act gaa tca<br>Val Pro Pro Pro Arg Lys Lys Arg Thr Val Val Leu Thr Glu Ser<br>          1085                      1090                  1095 | 3294 |
| acc cta tct act gcc ttg gcc gag ctc gcc acc aga agc ttt ggc<br>Thr Leu Ser Thr Ala Leu Ala Glu Leu Ala Thr Arg Ser Phe Gly | 3339 |

|  |  |  |  |  |  |  |  |  |  |  |  |  |  |  |
|---|---|---|---|---|---|---|---|---|---|---|---|---|---|---|
| 1100 | | | | | 1105 | | | | | 1110 | | | | |
| agc | tcc | tca | act | tcc | ggc | att | acg | ggc | gac | aat | acg | aca | aca | tcc | 3384 |
| Ser | Ser | Ser | Thr | Ser | Gly | Ile | Thr | Gly | Asp | Asn | Thr | Thr | Thr | Ser |
| 1115 | | | | | 1120 | | | | | 1125 | | | | |
| tct | gag | ccc | gcc | cct | tct | ggc | tgc | ccc | ccc | gac | tcc | gac | gct | gag | 3429 |
| Ser | Glu | Pro | Ala | Pro | Ser | Gly | Cys | Pro | Pro | Asp | Ser | Asp | Ala | Glu |
| 1130 | | | | | 1135 | | | | | 1140 | | | | |
| tcc | tat | tcc | tcc | atg | ccc | ccc | ctg | gag | ggg | gag | cct | ggg | gat | ccg | 3474 |
| Ser | Tyr | Ser | Ser | Met | Pro | Pro | Leu | Glu | Gly | Glu | Pro | Gly | Asp | Pro |
| 1145 | | | | | 1150 | | | | | 1155 | | | | |
| gat | ctt | agc | gac | ggg | tca | tgg | tca | acg | gtc | agt | agt | gag | gcc | aac | 3519 |
| Asp | Leu | Ser | Asp | Gly | Ser | Trp | Ser | Thr | Val | Ser | Ser | Glu | Ala | Asn |
| 1160 | | | | | 1165 | | | | | 1170 | | | | |
| gcg | gag | gat | gtc | gtg | tgc | tgc | tca | atg | tct | tac | tct | tgg | aca | ggc | 3564 |
| Ala | Glu | Asp | Val | Val | Cys | Cys | Ser | Met | Ser | Tyr | Ser | Trp | Thr | Gly |
| 1175 | | | | | 1180 | | | | | 1185 | | | | |
| gca | ctc | gtc | acc | ccg | tgc | gcc | gcg | gaa | gaa | cag | aaa | ctg | ccc | atc | 3609 |
| Ala | Leu | Val | Thr | Pro | Cys | Ala | Ala | Glu | Glu | Gln | Lys | Leu | Pro | Ile |
| 1190 | | | | | 1195 | | | | | 1200 | | | | |
| aat | gca | cta | agc | aac | tcg | ttg | cta | cgt | cac | cac | aat | ttg | gtg | tat | 3654 |
| Asn | Ala | Leu | Ser | Asn | Ser | Leu | Leu | Arg | His | His | Asn | Leu | Val | Tyr |
| 1205 | | | | | 1210 | | | | | 1215 | | | | |
| tcc | acc | acc | tca | cgc | agt | gct | tgc | caa | agg | cag | aag | aaa | gtc | aca | 3699 |
| Ser | Thr | Thr | Ser | Arg | Ser | Ala | Cys | Gln | Arg | Gln | Lys | Lys | Val | Thr |
| 1220 | | | | | 1225 | | | | | 1230 | | | | |
| ttt | gac | aga | ctg | caa | gtt | ctg | gac | agc | cat | tac | cag | gac | gta | ctc | 3744 |
| Phe | Asp | Arg | Leu | Gln | Val | Leu | Asp | Ser | His | Tyr | Gln | Asp | Val | Leu |
| 1235 | | | | | 1240 | | | | | 1245 | | | | |
| aag | gag | gtt | aaa | gca | gcg | gcg | tca | aaa | gtg | aag | gct | aac | ttg | cta | 3789 |
| Lys | Glu | Val | Lys | Ala | Ala | Ala | Ser | Lys | Val | Lys | Ala | Asn | Leu | Leu |
| 1250 | | | | | 1255 | | | | | 1260 | | | | |
| tcc | gta | gag | gaa | gct | tgc | agc | ctg | acg | ccc | cca | cac | tca | gcc | aaa | 3834 |
| Ser | Val | Glu | Glu | Ala | Cys | Ser | Leu | Thr | Pro | Pro | His | Ser | Ala | Lys |
| 1265 | | | | | 1270 | | | | | 1275 | | | | |
| tcc | aag | ttt | ggt | tat | ggg | gca | aaa | gac | gtc | cgt | tgc | cat | gcc | aga | 3879 |
| Ser | Lys | Phe | Gly | Tyr | Gly | Ala | Lys | Asp | Val | Arg | Cys | His | Ala | Arg |
| 1280 | | | | | 1285 | | | | | 1290 | | | | |
| aag | gcc | gta | acc | cac | atc | aac | tcc | gtg | tgg | aaa | gac | ctt | ctg | gaa | 3924 |
| Lys | Ala | Val | Thr | His | Ile | Asn | Ser | Val | Trp | Lys | Asp | Leu | Leu | Glu |
| 1295 | | | | | 1300 | | | | | 1305 | | | | |
| gac | aat | gta | aca | cca | ata | gac | act | acc | atc | atg | gct | aag | aac | gag | 3969 |
| Asp | Asn | Val | Thr | Pro | Ile | Asp | Thr | Thr | Ile | Met | Ala | Lys | Asn | Glu |
| 1310 | | | | | 1315 | | | | | 1320 | | | | |
| gtt | ttc | tgc | gtt | cag | cct | gag | aag | ggg | ggt | cgt | aag | cca | gct | cgt | 4014 |
| Val | Phe | Cys | Val | Gln | Pro | Glu | Lys | Gly | Gly | Arg | Lys | Pro | Ala | Arg |
| 1325 | | | | | 1330 | | | | | 1335 | | | | |
| ctc | atc | gtg | ttc | ccc | gat | ctg | ggc | gtg | cgc | gtg | tgc | gaa | aag | atg | 4059 |
| Leu | Ile | Val | Phe | Pro | Asp | Leu | Gly | Val | Arg | Val | Cys | Glu | Lys | Met |
| 1340 | | | | | 1345 | | | | | 1350 | | | | |
| gct | ttg | tac | gac | gtg | gtt | aca | aag | ctc | ccc | ttg | gcc | gtg | atg | gga | 4104 |
| Ala | Leu | Tyr | Asp | Val | Val | Thr | Lys | Leu | Pro | Leu | Ala | Val | Met | Gly |
| 1355 | | | | | 1360 | | | | | 1365 | | | | |
| agc | tcc | tac | gga | ttc | caa | tac | tca | cca | gga | cag | cgg | gtt | gaa | ttc | 4149 |
| Ser | Ser | Tyr | Gly | Phe | Gln | Tyr | Ser | Pro | Gly | Gln | Arg | Val | Glu | Phe |
| 1370 | | | | | 1375 | | | | | 1380 | | | | |
| ctc | gtg | caa | gcg | tgg | aag | tcc | aag | aaa | acc | cca | atg | ggg | ttc | tcg | 4194 |
| Leu | Val | Gln | Ala | Trp | Lys | Ser | Lys | Lys | Thr | Pro | Met | Gly | Phe | Ser |
| 1385 | | | | | 1390 | | | | | 1395 | | | | |
| tat | gat | acc | cgc | tgc | ttt | gac | tcc | aca | gtc | act | gag | agc | gac | atc | 4239 |
| Tyr | Asp | Thr | Arg | Cys | Phe | Asp | Ser | Thr | Val | Thr | Glu | Ser | Asp | Ile |

```
                      1400                1405                1410 cgt acg gag gag gca atc tac caa tgt tgt gac ctc gac ccc caa                4284
Arg Thr Glu Glu Ala Ile Tyr Gln Cys Cys Asp Leu Asp Pro Gln
1415                1420                1425 gcc cgc gtg gcc atc aag tcc ctc acc gag agg ctt tat gtt ggg                4329
Ala Arg Val Ala Ile Lys Ser Leu Thr Glu Arg Leu Tyr Val Gly
1430                1435                1440 ggc cct ctt acc aat tca agg ggg gag aac tgc ggc tat cgc agg                4374
Gly Pro Leu Thr Asn Ser Arg Gly Glu Asn Cys Gly Tyr Arg Arg
1445                1450                1455 tgc cgc gcg agc ggc gta ctg aca act agc tgt ggt aac acc ctc                4419
Cys Arg Ala Ser Gly Val Leu Thr Thr Ser Cys Gly Asn Thr Leu
1460                1465                1470 act tgc tac atc aag gcc cgg gca gcc tgt cga gcc gca ggg ctc                4464
Thr Cys Tyr Ile Lys Ala Arg Ala Ala Cys Arg Ala Ala Gly Leu
1475                1480                1485 cag gac tgc acc atg ctc gtg tgt ggc gac gac tta gtc gtt atc                4509
Gln Asp Cys Thr Met Leu Val Cys Gly Asp Asp Leu Val Val Ile
1490                1495                1500 tgt gaa agc gcg ggg gtc cag gag gac gcg gcg agc ctg aga gcc                4554
Cys Glu Ser Ala Gly Val Gln Glu Asp Ala Ala Ser Leu Arg Ala
1505                1510                1515 ttc acg gag gct atg acc agg tac tcc gcc ccc cct ggg gac ccc                4599
Phe Thr Glu Ala Met Thr Arg Tyr Ser Ala Pro Pro Gly Asp Pro
1520                1525                1530 cca caa cca gaa tac gac ttg gag ctc ata aca tca tgc tcc tcc                4644
Pro Gln Pro Glu Tyr Asp Leu Glu Leu Ile Thr Ser Cys Ser Ser
1535                1540                1545 aac gtg tca gtc gcc cac gac ggc gct gga aag agg gtc tac tac                4689
Asn Val Ser Val Ala His Asp Gly Ala Gly Lys Arg Val Tyr Tyr
1550                1555                1560 ctc acc cgt gac cct aca acc ccc ctc gcg aga gct gcg tgg gag                4734
Leu Thr Arg Asp Pro Thr Thr Pro Leu Ala Arg Ala Ala Trp Glu
1565                1570                1575 aca gca aga cac act cca gtc aat tcc tgg cta ggc aac ata atc                4779
Thr Ala Arg His Thr Pro Val Asn Ser Trp Leu Gly Asn Ile Ile
1580                1585                1590 atg ttt gcc ccc aca ctg tgg gcg agg atg ata ctg atg acc cat                4824
Met Phe Ala Pro Thr Leu Trp Ala Arg Met Ile Leu Met Thr His
1595                1600                1605 ttc ttt agc gtc ctt ata gcc agg gac cag ctt gaa cag gcc ctc                4869
Phe Phe Ser Val Leu Ile Ala Arg Asp Gln Leu Glu Gln Ala Leu
1610                1615                1620 gat tgc gag atc tac ggg gcc tgc tac tcc ata gaa cca ctg gat                4914
Asp Cys Glu Ile Tyr Gly Ala Cys Tyr Ser Ile Glu Pro Leu Asp
1625                1630                1635 cta cct cca atc att caa aga ctc cat ggc ctc agc gca ttt tca                4959
Leu Pro Pro Ile Ile Gln Arg Leu His Gly Leu Ser Ala Phe Ser
1640                1645                1650 ctc cac agt tac tct cca ggt gaa atc aat agg gtg gcc gca tgc                5004
Leu His Ser Tyr Ser Pro Gly Glu Ile Asn Arg Val Ala Ala Cys
1655                1660                1665 ctc aga aaa ctt ggg gta ccg ccc ttg cga gct tgg aga cac cgg                5049
Leu Arg Lys Leu Gly Val Pro Pro Leu Arg Ala Trp Arg His Arg
1670                1675                1680 gcc cgg agc gtc cgc gct agg ctt ctg gcc aga gga ggc agg gct                5094
Ala Arg Ser Val Arg Ala Arg Leu Leu Ala Arg Gly Gly Arg Ala
1685                1690                1695 gcc ata tgt ggc aag tac ctc ttc aac tgg gca gta aga aca aag                5139
Ala Ile Cys Gly Lys Tyr Leu Phe Asn Trp Ala Val Arg Thr Lys
```

```
                                                                    1700                    1705                    1710
ctc aaa ctc act cca ata gcg gcc gct ggc cag ctg gac ttg tcc                                                              5184
Leu Lys Leu Thr Pro Ile Ala Ala Ala Gly Gln Leu Asp Leu Ser
    1715                    1720                    1725 ggc tgg ttc acg gct ggc tac agc ggg gga gac att tat cac agc                                                              5229
Gly Trp Phe Thr Ala Gly Tyr Ser Gly Gly Asp Ile Tyr His Ser
1730                    1735                    1740 gtg tct cat gcc cgg ccc cgc tgg atc tgg ttt tgc cta ctc ctg                                                              5274
Val Ser His Ala Arg Pro Arg Trp Ile Trp Phe Cys Leu Leu Leu
    1745                    1750                    1755 ctt gct gca ggg gta ggc atc tac ctc ctc ccc aac cga atg agc                                                              5319
Leu Ala Ala Gly Val Gly Ile Tyr Leu Leu Pro Asn Arg Met Ser
    1760                    1765                    1770 acg aat cct aaa cct caa aga aag acc aaa cgt aac acc aac cgg                                                              5364
Thr Asn Pro Lys Pro Gln Arg Lys Thr Lys Arg Asn Thr Asn Arg
    1775                    1780                    1785 cgg ccg cag gac gtc aag ttc ccg ggt ggc ggt cag atc gtt ggt                                                              5409
Arg Pro Gln Asp Val Lys Phe Pro Gly Gly Gly Gln Ile Val Gly
    1790                    1795                    1800 gga gtt tac ttg ttg ccg cgc agg ggc cct aga ttg ggt gtg cgc                                                              5454
Gly Val Tyr Leu Leu Pro Arg Arg Gly Pro Arg Leu Gly Val Arg
1805                    1810                    1815 gcg acg aga aag act tcc gag cgg tcg caa cct cga ggt aga cgt                                                              5499
Ala Thr Arg Lys Thr Ser Glu Arg Ser Gln Pro Arg Gly Arg Arg
    1820                    1825                    1830 cag cct atc ccc aag gct cgt cgg ccc gag ggc agg acc tgg gct                                                              5544
Gln Pro Ile Pro Lys Ala Arg Arg Pro Glu Gly Arg Thr Trp Ala
    1835                    1840                    1845 cag ccc ggg tac cct tgg ccc ctc tat ggc aat gag ggc tgc ggg                                                              5589
Gln Pro Gly Tyr Pro Trp Pro Leu Tyr Gly Asn Glu Gly Cys Gly
    1850                    1855                    1860 tgg gcg gga tgg ctc ctg tct ccc cgt ggc tct cgg cct agc tgg                                                              5634
Trp Ala Gly Trp Leu Leu Ser Pro Arg Gly Ser Arg Pro Ser Trp
1865                    1870                    1875 ggc ccc aca gac ccc cgg cgt agg tcg cgc aat ttg ggt aag                                                                  5676
Gly Pro Thr Asp Pro Arg Arg Arg Ser Arg Asn Leu Gly Lys
    1880                    1885                    1890

<210> SEQ ID NO 6
<211> LENGTH: 1892
<212> TYPE: PRT
<213> ORGANISM: Artificial
<220> FEATURE:
<223> OTHER INFORMATION: Synthetic Construct

<400> SEQUENCE: 6

Met Ala Ala Tyr Ala Ala Gln Gly Tyr Lys Val Leu Val Leu Asn Pro
1               5                   10                  15

Ser Val Ala Ala Thr Leu Gly Phe Gly Ala Tyr Met Ser Lys Ala His
            20                  25                  30

Gly Ile Asp Pro Asn Ile Arg Thr Gly Val Arg Thr Ile Thr Thr Gly
        35                  40                  45

Ser Pro Ile Thr Tyr Ser Thr Tyr Gly Lys Phe Leu Ala Asp Gly Gly
    50                  55                  60

Cys Ser Gly Gly Ala Tyr Asp Ile Ile Ile Cys Asp Glu Cys His Ser
65                  70                  75                  80

Thr Asp Ala Thr Ser Ile Leu Gly Ile Gly Thr Val Leu Asp Gln Ala
                85                  90                  95

Glu Thr Ala Gly Ala Arg Leu Val Val Leu Ala Thr Ala Thr Pro Pro
            100                 105                 110
```

```
Gly Ser Val Thr Val Pro His Pro Asn Ile Glu Glu Val Ala Leu Ser
            115                 120                 125

Thr Thr Gly Glu Ile Pro Phe Tyr Gly Lys Ala Ile Pro Leu Glu Val
        130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
    275                 280                 285

Glu Leu Thr Pro Ala Glu Thr Thr Val Arg Leu Arg Ala Tyr Met Asn
290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
            325                 330                 335

Lys Gln Ser Gly Glu Asn Leu Pro Tyr Leu Val Ala Tyr Gln Ala Thr
        340                 345                 350

Val Cys Ala Arg Ala Gln Ala Pro Pro Pro Ser Trp Asp Gln Met Trp
    355                 360                 365

Lys Cys Leu Ile Arg Leu Lys Pro Thr Leu His Gly Pro Thr Pro Leu
370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
            405                 410                 415

Thr Ser Thr Trp Val Leu Val Gly Gly Val Leu Ala Ala Leu Ala Ala
        420                 425                 430

Tyr Cys Leu Ser Thr Gly Cys Val Val Ile Val Gly Arg Val Val Leu
    435                 440                 445

Ser Gly Lys Pro Ala Ile Ile Pro Asp Arg Glu Val Leu Tyr Arg Glu
450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
            485                 490                 495

Gln Thr Ala Ser Arg Gln Ala Glu Val Ile Ala Pro Ala Val Gln Thr
        500                 505                 510

Asn Trp Gln Lys Leu Glu Thr Phe Trp Ala Lys His Met Trp Asn Phe
    515                 520                 525

Ile Ser Gly Ile Gln Tyr Leu Ala Gly Leu Ser Thr Leu Pro Gly Asn
```

```
                530                 535                 540
Pro Ala Ile Ala Ser Leu Met Ala Phe Thr Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
                580                 585                 590

Gly Leu Ala Gly Ala Ala Ile Gly Ser Val Gly Leu Gly Lys Val Leu
                595                 600                 605

Ile Asp Ile Leu Ala Gly Tyr Gly Ala Gly Val Ala Gly Ala Leu Val
610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
                660                 665                 670

Val Gln Trp Met Asn Arg Leu Ile Ala Phe Ala Ser Arg Gly Asn His
                675                 680                 685

Val Ser Pro Thr His Tyr Val Pro Glu Ser Asp Ala Ala Arg Val
690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
                740                 745                 750

Thr Trp Leu Lys Ala Lys Leu Met Pro Gln Leu Pro Gly Ile Pro Phe
                755                 760                 765

Val Ser Cys Gln Arg Gly Tyr Lys Gly Val Trp Arg Gly Asp Gly Ile
                770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
                820                 825                 830

Leu Pro Ala Pro Asn Tyr Thr Phe Ala Leu Trp Arg Val Ser Ala Glu
                835                 840                 845

Glu Tyr Val Glu Ile Arg Gln Val Gly Asp Phe His Tyr Val Thr Gly
                850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
                900                 905                 910

Glu Tyr Pro Val Gly Ser Gln Leu Pro Cys Glu Pro Glu Pro Asp Val
                915                 920                 925

Ala Val Leu Thr Ser Met Leu Thr Asp Pro Ser His Ile Thr Ala Glu
                930                 935                 940

Ala Ala Gly Arg Arg Leu Ala Arg Gly Ser Pro Pro Ser Val Ala Ser
945                 950                 955                 960
```

-continued

```
Ser Ser Ala Ser Gln Leu Ser Ala Pro Ser Leu Lys Ala Thr Cys Thr
            965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu
        1010                1015                1020

Asp Glu Arg Glu Ile Ser Val Pro Ala Glu Ile Leu Arg Lys Ser
        1025                1030                1035

Arg Arg Phe Ala Gln Ala Leu Pro Val Trp Ala Arg Pro Asp Tyr
        1040                1045                1050

Asn Pro Pro Leu Val Glu Thr Trp Lys Lys Pro Asp Tyr Glu Pro
        1055                1060                1065

Pro Val Val His Gly Cys Pro Leu Pro Pro Lys Ser Pro Pro
        1070                1075                1080

Val Pro Pro Arg Lys Lys Arg Thr Val Val Leu Thr Glu Ser
        1085                1090                1095

Thr Leu Ser Thr Ala Leu Ala Glu Leu Ala Thr Arg Ser Phe Gly
        1100                1105                1110

Ser Ser Ser Thr Ser Gly Ile Thr Gly Asp Asn Thr Thr Thr Ser
        1115                1120                1125

Ser Glu Pro Ala Pro Ser Gly Cys Pro Pro Asp Ser Asp Ala Glu
        1130                1135                1140

Ser Tyr Ser Ser Met Pro Pro Leu Glu Gly Glu Pro Gly Asp Pro
        1145                1150                1155

Asp Leu Ser Asp Gly Ser Trp Ser Thr Val Ser Ser Glu Ala Asn
        1160                1165                1170

Ala Glu Asp Val Val Cys Cys Ser Met Ser Tyr Ser Trp Thr Gly
        1175                1180                1185

Ala Leu Val Thr Pro Cys Ala Ala Glu Glu Gln Lys Leu Pro Ile
        1190                1195                1200

Asn Ala Leu Ser Asn Ser Leu Leu Arg His His Asn Leu Val Tyr
        1205                1210                1215

Ser Thr Thr Ser Arg Ser Ala Cys Gln Arg Gln Lys Lys Val Thr
        1220                1225                1230

Phe Asp Arg Leu Gln Val Leu Asp Ser His Tyr Gln Asp Val Leu
        1235                1240                1245

Lys Glu Val Lys Ala Ala Ala Ser Lys Val Lys Ala Asn Leu Leu
        1250                1255                1260

Ser Val Glu Glu Ala Cys Ser Leu Thr Pro Pro His Ser Ala Lys
        1265                1270                1275

Ser Lys Phe Gly Tyr Gly Ala Lys Asp Val Arg Cys His Ala Arg
        1280                1285                1290

Lys Ala Val Thr His Ile Asn Ser Val Trp Lys Asp Leu Leu Glu
        1295                1300                1305

Asp Asn Val Thr Pro Ile Asp Thr Thr Ile Met Ala Lys Asn Glu
        1310                1315                1320

Val Phe Cys Val Gln Pro Glu Lys Gly Gly Arg Lys Pro Ala Arg
        1325                1330                1335

Leu Ile Val Phe Pro Asp Leu Gly Val Arg Val Cys Glu Lys Met
        1340                1345                1350

Ala Leu Tyr Asp Val Val Thr Lys Leu Pro Leu Ala Val Met Gly
        1355                1360                1365
```

```
Ser Ser Tyr Gly Phe Gln Tyr Ser Pro Gly Gln Arg Val Glu Phe
    1370                1375                1380

Leu Val Gln Ala Trp Lys Ser Lys Lys Thr Pro Met Gly Phe Ser
    1385                1390                1395

Tyr Asp Thr Arg Cys Phe Asp Ser Thr Val Thr Glu Ser Asp Ile
    1400                1405                1410

Arg Thr Glu Glu Ala Ile Tyr Gln Cys Cys Asp Leu Asp Pro Gln
    1415                1420                1425

Ala Arg Val Ala Ile Lys Ser Leu Thr Glu Arg Leu Tyr Val Gly
    1430                1435                1440

Gly Pro Leu Thr Asn Ser Arg Gly Glu Asn Cys Gly Tyr Arg Arg
    1445                1450                1455

Cys Arg Ala Ser Gly Val Leu Thr Thr Ser Cys Gly Asn Thr Leu
    1460                1465                1470

Thr Cys Tyr Ile Lys Ala Arg Ala Ala Cys Arg Ala Ala Gly Leu
    1475                1480                1485

Gln Asp Cys Thr Met Leu Val Cys Gly Asp Asp Leu Val Val Ile
    1490                1495                1500

Cys Glu Ser Ala Gly Val Gln Glu Asp Ala Ala Ser Leu Arg Ala
    1505                1510                1515

Phe Thr Glu Ala Met Thr Arg Tyr Ser Ala Pro Pro Gly Asp Pro
    1520                1525                1530

Pro Gln Pro Glu Tyr Asp Leu Glu Leu Ile Thr Ser Cys Ser Ser
    1535                1540                1545

Asn Val Ser Val Ala His Asp Gly Ala Gly Lys Arg Val Tyr Tyr
    1550                1555                1560

Leu Thr Arg Asp Pro Thr Thr Pro Leu Ala Arg Ala Ala Trp Glu
    1565                1570                1575

Thr Ala Arg His Thr Pro Val Asn Ser Trp Leu Gly Asn Ile Ile
    1580                1585                1590

Met Phe Ala Pro Thr Leu Trp Ala Arg Met Ile Leu Met Thr His
    1595                1600                1605

Phe Phe Ser Val Leu Ile Ala Arg Asp Gln Leu Glu Gln Ala Leu
    1610                1615                1620

Asp Cys Glu Ile Tyr Gly Ala Cys Tyr Ser Ile Glu Pro Leu Asp
    1625                1630                1635

Leu Pro Pro Ile Ile Gln Arg Leu His Gly Leu Ser Ala Phe Ser
    1640                1645                1650

Leu His Ser Tyr Ser Pro Gly Glu Ile Asn Arg Val Ala Ala Cys
    1655                1660                1665

Leu Arg Lys Leu Gly Val Pro Pro Leu Arg Ala Trp Arg His Arg
    1670                1675                1680

Ala Arg Ser Val Arg Ala Leu Leu Ala Arg Gly Gly Arg Ala
    1685                1690                1695

Ala Ile Cys Gly Lys Tyr Leu Phe Asn Trp Ala Val Arg Thr Lys
    1700                1705                1710

Leu Lys Leu Thr Pro Ile Ala Ala Ala Gly Gln Leu Asp Leu Ser
    1715                1720                1725

Gly Trp Phe Thr Ala Gly Tyr Ser Gly Gly Asp Ile Tyr His Ser
    1730                1735                1740

Val Ser His Ala Arg Pro Arg Trp Ile Trp Phe Cys Leu Leu Leu
    1745                1750                1755

Leu Ala Ala Gly Val Gly Ile Tyr Leu Leu Pro Asn Arg Met Ser
```

```
         1760                1765                1770
Thr Asn Pro Lys Pro Gln Arg Lys Thr Lys Arg Asn Thr Asn Arg
   1775                1780                1785

Arg Pro Gln Asp Val Lys Phe Pro Gly Gly Gly Gln Ile Val Gly
   1790                1795                1800

Gly Val Tyr Leu Leu Pro Arg Arg Gly Pro Arg Leu Gly Val Arg
   1805                1810                1815

Ala Thr Arg Lys Thr Ser Glu Arg Ser Gln Pro Arg Gly Arg Arg
   1820                1825                1830

Gln Pro Ile Pro Lys Ala Arg Arg Pro Glu Gly Arg Thr Trp Ala
   1835                1840                1845

Gln Pro Gly Tyr Pro Trp Pro Leu Tyr Gly Asn Glu Gly Cys Gly
   1850                1855                1860

Trp Ala Gly Trp Leu Leu Ser Pro Arg Gly Ser Arg Pro Ser Trp
   1865                1870                1875

Gly Pro Thr Asp Pro Arg Arg Arg Ser Arg Asn Leu Gly Lys
   1880                1885                1890

<210> SEQ ID NO 7
<211> LENGTH: 3417
<212> TYPE: DNA
<213> ORGANISM: Artificial
<220> FEATURE:
<223> OTHER INFORMATION: synthetic DNA sequence of a representative
      fusion protein that includes a C-terminally truncated NS5
      polypeptide with the C-terminus of the NS5 polypeptide fused to a
      core polypeptide

<400> SEQUENCE: 7
tccggttcct ggctaaggga catctgggac tggatatgcg aggtgttgag cgactttaag      60
acctggctaa aagctaagct catgccacag ctgcctggga tccccttgtg tcctgccag     120 cgcgggtata aggggtctg gcgaggggac ggcatcatgc acactcgctg ccactgtgga     180
gctgagatca ctggacatgt caaaaacggg acgatgagga tcgtcggtcc taggacctgc     240
aggaacatgt ggagtgggac cttccccatt aatgcctaca ccacgggccc ctgtacccc      300 cttcctgcgc cgaactacac gttcgcgcta tgagggtgt ctgcagagga atacgtggag     360
ataaggcagg tggggactt ccactacgtg acgggtatga ctactgacaa tcttaaatgc     420
ccgtgccagg tcccatcgcc cgaattttc acagaattgg acggggtgcg cctacatagg     480
tttgcgcccc cctgcaagcc cttgctgcgg gaggaggtat cattcagagt aggactccac     540
gaatacccgg tagggtcgca attccttgc gagcccgaac cggacgtggc cgtgttgacg     600
tccatgctca ctgatcccctc ccatataaca gcagaggcgg ccgggcgaag gttggcgagg     660
ggatcacccc cctctgtggc cagctcctcg gctagccagc tatccgctcc atctctcaag     720
gcaacttgca ccgctaacca tgactcccct gatgctgagc tcatagaggc caacctccta     780
tggaggcagg agatgggcgg caacatcacc agggttgagt cagaaaacaa agtggtgatt     840
ctggactcct tcgatccgct tgtggcggag gaggacgagc gggagatctc cgtacccgca     900
gaaatcctgc ggaagtctcg gagattcgcc caggccctgc ccgtttgggc gcggccggac     960 tataacccc cgctagtgga gacgtggaaa aagcccgact acgaaccacc tgtggtccat    1020 ggctgccgc ttccacctcc aaagtcccct ctgtgcctc cgcctcggaa gaagcggacg    1080
gtggtcctca ctgaatcaac cctatctact gccttggccg agctcgccac cagaagcttt    1140
ggcagctcct caacttccgg cattacgggc gacaatacga acatcctc tgagcccgcc    1200 ccttctggct gccccccga ctccgacgct gagtcctatt cctccatgcc ccccctggag    1260
```

```
ggggagcctg gggatccgga tcttagcgac gggtcatggt caacggtcag tagtgaggcc    1320
aacgcggagg atgtcgtgtg ctgctcaatg tcttactctt ggacaggcgc actcgtcacc    1380
ccgtgcgccg cggaagaaca gaaactgccc atcaatgcac taagcaactc gttgctacgt    1440
caccacaatt tggtgtattc caccacctca cgcagtgctt gccaaaggca gaagaaagtc    1500
acatttgaca gactgcaagt tctggacagc cattaccagg acgtactcaa ggaggttaaa    1560
gcagcggcgt caaaagtgaa ggctaacttg ctatccgtag aggaagcttg cagcctgacg    1620
cccccacact cagccaaatc caagtttggt tatggggcaa agacgtccg ttgccatgcc     1680 agaaaggccg taacccacat caactccgtg tggaaagacc ttctggaaga caatgtaaca    1740
ccaatagaca ctaccatcat ggctaagaac gaggttttct gcgttcagcc tgagaagggg    1800
ggtcgtaagc cagctcgtct catcgtgttc cccgatctgg gcgtgcgcgt gtgcgaaaag    1860
atggctttgt acgacgtggt tacaaagctc cccttggccg tgatgggaag ctcctacgga    1920
ttccaatact caccaggaca gcgggttgaa ttcctcgtgc aagcgtggaa gtccaagaaa    1980
accccaatgg ggttctcgta tgatacccgc tgctttgact ccacagtcac tgagagcgac    2040
atccgtacgg aggaggcaat ctaccaatgt tgtgacctcg accccaagc cgcgtggcc     2100 atcaagtccc tcaccgagag ctttatgtt gggggccctc ttaccaattc aaggggggag    2160
aactgcggct atcgcaggtg ccgcgcgagc ggcgtactga caactagctg tggtaacacc    2220
ctcacttgct acatcaaggc ccgggcagcc tgtcgagccg cagggctcca ggactgcacc    2280
atgctcgtgt gtggcgacga cttagtcgtt atctgtgaaa gcgcggggt ccaggaggac     2340 gcggcgagcc tgagagcctt cacggaggct atgaccaggt actccgcccc cctggggac    2400 cccccacaac cagaatacga cttggagctc ataacatcat gctcctccaa cgtgtcagtc    2460
gcccacgacg gcgctggaaa gagggtctac tacctcaccc gtgaccctac aaccccctc    2520 gcgagagctg cgtgggagac agcaagacac actccagtca attcctggct aggcaacata    2580
atcatgtttg cccccacact gtgggcgagg atgatactga tgacccattt ctttagcgtc    2640
cttatagcca gggaccagct tgaacaggcc ctcgattgcg agatctacgg ggcctgctac    2700
tccatagaac cactggatct acctccaatc attcaaagac tccatggcct cagcgcattt    2760
tcactccaca gttactctcc aggtgaaatc aatagggtgg ccgcatgcct cagaaaactt    2820
ggggtaccgc ccttgcgagc ttggagacac cgggcccgga gcgtccgcgc taggcttctg    2880
gccagaggag gcagggctgc catatgtggc aagtacctct tcaactgggc agtaagaaca    2940
aagctcaaac tcactccaat agcggccgct ggccagctgg acttgtccgg ctggttcacg    3000
gctggctaca gcggggagag catttatcac agcgtgtctc atgcccggcc ccgcatgagc    3060
acgaatccta aacctcaaag aaagaccaaa cgtaacacca accggcggcc gcaggacgtc    3120
aagttcccgg gtggcggtca gatcgttggt ggagtttact tgttccgcg caggggccct    3180 agattgggtg tgcgcgcgac gagaaagact tccgagcggt cgcaacctcg aggtagacgt    3240
cagcctatcc ccaaggctcg tcggcccgag gcaggacct gggctcagcc cgggtaccct     3300
tggcccctct atggcaatga gggctgcggg tgggcgggat ggctcctgtc tccccgtggc    3360
tctcggccta gctggggccc cacagacccc cggcgtaggt cgcgcaattt gggtaag       3417
```

<210> SEQ ID NO 8
<211> LENGTH: 1139
<212> TYPE: PRT
<213> ORGANISM: Artificial
<220> FEATURE:
<223> OTHER INFORMATION: synthetic amino acid sequence of a representative fusion protein that includes a C-terminally
truncated NS5 polypeptide with the C-terminus of the NS5
polypeptide fused to a core polypeptide

<400> SEQUENCE: 8

```
Ser Gly Ser Trp Leu Arg Asp Ile Trp Asp Trp Ile Cys Glu Val Leu
1               5                   10                  15

Ser Asp Phe Lys Thr Trp Leu Lys Ala Lys Leu Met Pro Gln Leu Pro
            20                  25                  30

Gly Ile Pro Phe Val Ser Cys Gln Arg Gly Tyr Lys Gly Val Trp Arg
        35                  40                  45

Gly Asp Gly Ile Met His Thr Arg Cys His Cys Gly Ala Glu Ile Thr
    50                  55                  60

Gly His Val Lys Asn Gly Thr Met Arg Ile Val Gly Pro Arg Thr Cys
65                  70                  75                  80

Arg Asn Met Trp Ser Gly Thr Phe Pro Ile Asn Ala Tyr Thr Thr Gly
                85                  90                  95

Pro Cys Thr Pro Leu Pro Ala Pro Asn Tyr Thr Phe Ala Leu Trp Arg
            100                 105                 110

Val Ser Ala Glu Glu Tyr Val Glu Ile Arg Gln Val Gly Asp Phe His
        115                 120                 125

Tyr Val Thr Gly Met Thr Thr Asp Asn Leu Lys Cys Pro Cys Gln Val
    130                 135                 140

Pro Ser Pro Glu Phe Phe Thr Glu Leu Asp Gly Val Arg Leu His Arg
145                 150                 155                 160

Phe Ala Pro Pro Cys Lys Pro Leu Leu Arg Glu Glu Val Ser Phe Arg
                165                 170                 175

Val Gly Leu His Glu Tyr Pro Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Ala Ala Gly Arg Arg Leu Ala Arg Gly Ser Pro Pro
    210                 215                 220

Ser Val Ala Ser Ser Ala Ser Gln Leu Ser Ala Pro Ser Leu Lys
225                 230                 235                 240

Ala Thr Cys Thr Ala Asn His Asp Ser Pro Asp Ala Glu Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Asp Pro Leu Val
        275                 280                 285

Ala Glu Glu Asp Glu Arg Glu Ile Ser Val Pro Ala Glu Ile Leu Arg
    290                 295                 300

Lys Ser Arg Arg Phe Ala Gln Ala Leu Pro Val Trp Ala Arg Pro Asp
305                 310                 315                 320

Tyr Asn Pro Pro Leu Val Glu Thr Trp Lys Lys Pro Asp Tyr Glu Pro
                325                 330                 335

Pro Val Val His Gly Cys Pro Leu Pro Pro Lys Ser Pro Pro Val
            340                 345                 350

Pro Pro Pro Arg Lys Lys Arg Thr Val Val Leu Thr Glu Ser Thr Leu
        355                 360                 365

Ser Thr Ala Leu Ala Glu Leu Ala Thr Arg Ser Phe Gly Ser Ser Ser
    370                 375                 380

Thr Ser Gly Ile Thr Gly Asp Asn Thr Thr Ser Ser Glu Pro Ala
385                 390                 395                 400
```

```
Pro Ser Gly Cys Pro Pro Asp Ser Asp Ala Glu Ser Tyr Ser Ser Met
            405                 410                 415

Pro Pro Leu Glu Gly Glu Pro Gly Asp Pro Asp Leu Ser Asp Gly Ser
            420                 425                 430

Trp Ser Thr Val Ser Ser Glu Ala Asn Ala Glu Asp Val Val Cys Cys
            435                 440                 445

Ser Met Ser Tyr Ser Trp Thr Gly Ala Leu Val Thr Pro Cys Ala Ala
    450                 455                 460

Glu Glu Gln Lys Leu Pro Ile Asn Ala Leu Ser Asn Ser Leu Leu Arg
465                 470                 475                 480

His His Asn Leu Val Tyr Ser Thr Thr Ser Arg Ser Ala Cys Gln Arg
                485                 490                 495

Gln Lys Lys Val Thr Phe Asp Arg Leu Gln Val Leu Asp Ser His Tyr
            500                 505                 510

Gln Asp Val Leu Lys Glu Val Lys Ala Ala Ser Lys Val Lys Ala
            515                 520                 525

Asn Leu Leu Ser Val Glu Glu Ala Cys Ser Leu Thr Pro Pro His Ser
    530                 535                 540

Ala Lys Ser Lys Phe Gly Tyr Gly Ala Lys Asp Val Arg Cys His Ala
545                 550                 555                 560

Arg Lys Ala Val Thr His Ile Asn Ser Val Trp Lys Asp Leu Leu Glu
                565                 570                 575

Asp Asn Val Thr Pro Ile Asp Thr Thr Ile Met Ala Lys Asn Glu Val
            580                 585                 590

Phe Cys Val Gln Pro Glu Lys Gly Gly Arg Lys Pro Ala Arg Leu Ile
            595                 600                 605

Val Phe Pro Asp Leu Gly Val Arg Val Cys Glu Lys Met Ala Leu Tyr
    610                 615                 620

Asp Val Val Thr Lys Leu Pro Leu Ala Val Met Gly Ser Ser Tyr Gly
625                 630                 635                 640

Phe Gln Tyr Ser Pro Gly Gln Arg Val Glu Phe Leu Val Gln Ala Trp
                645                 650                 655

Lys Ser Lys Lys Thr Pro Met Gly Phe Ser Tyr Asp Thr Arg Cys Phe
            660                 665                 670

Asp Ser Thr Val Thr Glu Ser Asp Ile Arg Thr Glu Glu Ala Ile Tyr
            675                 680                 685

Gln Cys Cys Asp Leu Asp Pro Gln Ala Arg Val Ala Ile Lys Ser Leu
    690                 695                 700

Thr Glu Arg Leu Tyr Val Gly Gly Pro Leu Thr Asn Ser Arg Gly Glu
705                 710                 715                 720

Asn Cys Gly Tyr Arg Arg Cys Arg Ala Ser Gly Val Leu Thr Thr Ser
                725                 730                 735

Cys Gly Asn Thr Leu Thr Cys Tyr Ile Lys Ala Arg Ala Ala Cys Arg
            740                 745                 750

Ala Ala Gly Leu Gln Asp Cys Thr Met Leu Val Cys Gly Asp Asp Leu
            755                 760                 765

Val Val Ile Cys Glu Ser Ala Gly Val Gln Glu Asp Ala Ala Ser Leu
    770                 775                 780

Arg Ala Phe Thr Glu Ala Met Thr Arg Tyr Ser Ala Pro Pro Gly Asp
785                 790                 795                 800

Pro Pro Gln Pro Glu Tyr Asp Leu Glu Leu Ile Thr Ser Cys Ser Ser
                805                 810                 815

Asn Val Ser Val Ala His Asp Gly Ala Gly Lys Arg Val Tyr Tyr Leu
```

```
                        820                 825                 830
Thr Arg Asp Pro Thr Thr Pro Leu Ala Arg Ala Ala Trp Glu Thr Ala
            835                 840                 845

Arg His Thr Pro Val Asn Ser Trp Leu Gly Asn Ile Ile Met Phe Ala
    850                 855                 860

Pro Thr Leu Trp Ala Arg Met Ile Leu Met Thr His Phe Phe Ser Val
865                 870                 875                 880

Leu Ile Ala Arg Asp Gln Leu Glu Gln Ala Leu Asp Cys Glu Ile Tyr
                885                 890                 895

Gly Ala Cys Tyr Ser Ile Glu Pro Leu Asp Leu Pro Pro Ile Ile Gln
            900                 905                 910

Arg Leu His Gly Leu Ser Ala Phe Ser Leu His Ser Tyr Ser Pro Gly
        915                 920                 925

Glu Ile Asn Arg Val Ala Ala Cys Leu Arg Lys Leu Gly Val Pro Pro
    930                 935                 940

Leu Arg Ala Trp Arg His Arg Ala Arg Ser Val Arg Ala Arg Leu Leu
945                 950                 955                 960

Ala Arg Gly Gly Arg Ala Ala Ile Cys Gly Lys Tyr Leu Phe Asn Trp
                965                 970                 975

Ala Val Arg Thr Lys Leu Lys Leu Thr Pro Ile Ala Ala Gly Gln
            980                 985                 990

Leu Asp Leu Ser Gly Trp Phe Thr Ala Gly Tyr Ser Gly Gly Asp Ile
        995                 1000                1005

Tyr His Ser Val Ser His Ala Arg Pro Arg Met Ser Thr Asn Pro
    1010                1015                1020

Lys Pro Gln Arg Lys Thr Lys Arg Asn Thr Asn Arg Arg Pro Gln
    1025                1030                1035

Asp Val Lys Phe Pro Gly Gly Gly Gln Ile Val Gly Gly Val Tyr
    1040                1045                1050

Leu Leu Pro Arg Arg Gly Pro Arg Leu Gly Val Arg Ala Thr Arg
    1055                1060                1065

Lys Thr Ser Glu Arg Ser Gln Pro Arg Gly Arg Arg Gln Pro Ile
    1070                1075                1080

Pro Lys Ala Arg Arg Pro Glu Gly Arg Thr Trp Ala Gln Pro Gly
    1085                1090                1095

Tyr Pro Trp Pro Leu Tyr Gly Asn Glu Cys Gly Trp Ala Gly
    1100                1105                1110

Trp Leu Leu Ser Pro Arg Gly Ser Arg Pro Ser Trp Gly Pro Thr
    1115                1120                1125

Asp Pro Arg Arg Arg Ser Arg Asn Leu Gly Lys
    1130                1135

<210> SEQ ID NO 9
<211> LENGTH: 21
<212> TYPE: PRT
<213> ORGANISM: Artificial
<220> FEATURE:
<223> OTHER INFORMATION: Hepatitis C virus type 1 E2 consensus sequence

<400> SEQUENCE: 9

Gly Ser Ala Ala Arg Thr Thr Ser Gly Phe Val Ser Leu Phe Ala Pro
1               5                   10                  15

Gly Ala Lys Gln Asn
            20

```
<211> LENGTH: 10
<212> TYPE: DNA
<213> ORGANISM: Artificial
<220> FEATURE:
<223> OTHER INFORMATION: vector sequence

<400> SEQUENCE: 10
acaaaacaaa                                                           10

<210> SEQ ID NO 11
<211> LENGTH: 15
<212> TYPE: PRT
<213> ORGANISM: Artificial
<220> FEATURE:
<223> OTHER INFORMATION: synthetic hepatitis C virus NS3-1 peptide

<400> SEQUENCE: 11

Leu Val Ala Leu Gly Ile Asn Ala Val Ala Tyr Tyr Arg Gly Leu
1               5                   10                  15

<210> SEQ ID NO 12
<211> LENGTH: 15
<212> TYPE: PRT
<213> ORGANISM: Artificial
<220> FEATURE:
<223> OTHER INFORMATION: synthetic hepatitis C virus NS3-2 peptide

<400> SEQUENCE: 12

Thr Thr Val Arg Leu Arg Ala Tyr Met Asn Thr Pro Gly Leu Pro
1               5                   10                  15

<210> SEQ ID NO 13
<211> LENGTH: 10
<212> TYPE: PRT
<213> ORGANISM: Artificial
<220> FEATURE:
<223> OTHER INFORMATION: synthetic hepatitis C virus NS3-3 peptide

<400> SEQUENCE: 13

Ser Ser Pro Pro Val Val Pro Gln Ser Phe
1               5                   10

<210> SEQ ID NO 14
<211> LENGTH: 16
<212> TYPE: PRT
<213> ORGANISM: Artificial
<220> FEATURE:
<223> OTHER INFORMATION: synthetic hepatitis C virus NS5B peptide

<400> SEQUENCE: 14

Met Ser Tyr Ser Trp Thr Gly Ala Leu Val Thr Pro Cys Ala Ala Glu
1               5                   10                  15
```

What is claimed is:

1. A polynucleotide comprising a coding sequence encoding an HCV fusion polypeptide consisting of a polypeptide selected from the group of polypeptides consisting of:

(1) in an amino terminal to carboxy terminal direction, numbered relative to HCV-1, a methionine, amino acids 384 to 715 of E2, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is arginine and amino acid 11 of the core sequence is threonine;

(2) in an amino terminal to carboxy terminal direction, numbered relative to HCV-1, a methionine, amino acids 384 to 715 of E2, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a arginine and amino acid 11 of the core sequence is threonine;

(3) in an amino terminal to carboxy terminal direction, numbered relative to HCV-1, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a arginine and amino acid 11 of the core sequence is threonine; and (4) in an amino terminal to carboxy terminal direction, numbered relative to HCV-1, amino acids 1018 to 1026 of NS2, amino acids 1027 to 1657 of NS3, amino acids 1658 to 1972 of NS4, amino acids 1973 to 3011 of NS5 and amino acids 1 to 121 of core, wherein the serine at position 1165 of the NS3 sequence is replaced with an alanine, amino acid 9 of the core sequence is a arginine and amino acid 11 of the core sequence is threonine.

2. An isolated nucleic acid encoding (a) the polynucleotide according to claim 1; and (b) a promoter operably linked at the 5' terminus of the polynucleotide, whereby the coding sequence can be transcribed and translated in a host cell.

3. A host cell transformed with the nucleic acid of claim 2.

4. A method for producing an HCV fusion polypeptide, said method comprising culturing a population of host cells according to claim 3 under conditions for producing said polypeptide.

5. The isolated nucleic acid of claim 2, wherein the promoter is an ADH2/GAPDH (Alcohol dehydrogenase 2/Glyceraldehyde-3-phosphate dehydrogenase) promoter.

6. A yeast host cell transformed with the nucleic acid of claim 5.

7. A method for producing an HCV fusion polypeptide, said method comprising culturing a population of host cells according to claim 6 under conditions for producing said polypeptide.

* * * * *